(12) United States Patent
Zaver et al.

(10) Patent No.: US 10,898,198 B2
(45) Date of Patent: Jan. 26, 2021

(54) APPARATUS FOR DELIVERING AN IMPLANT WITHOUT BIAS TO A LEFT ATRIAL APPENDAGE

(71) Applicant: ATRITECH, INC., Plymouth, MN (US)

(72) Inventors: Steve Zaver, Plymouth, MN (US); Kevin Anderson, Brooklyn Center, MN (US); Kevin Cowden, Maple Grove, MN (US); Chris Quinn, Minneapolis, MN (US); Brian Watschke, Eden Prairie, MN (US)

(73) Assignee: Atritech, Inc., Plymouth, MN (US)

( * ) Notice: Subject to any disclaimer, the term of this patent is extended or adjusted under 35 U.S.C. 154(b) by 293 days.

(21) Appl. No.: 15/822,080

(22) Filed: Nov. 24, 2017

(65) Prior Publication Data

US 2018/0070950 A1    Mar. 15, 2018

Related U.S. Application Data

(63) Continuation of application No. 14/705,561, filed on May 6, 2015, now Pat. No. 10,076,335, which is a
(Continued)

(51) Int. Cl.
*A61B 17/12* (2006.01)
*A61B 17/00* (2006.01)
(Continued)

(52) U.S. Cl.
CPC .... *A61B 17/12022* (2013.01); *A61B 17/0057* (2013.01); *A61B 17/12122* (2013.01);
(Continued)

(58) Field of Classification Search
CPC .. A61B 2017/12054; A61B 2017/1205; A61B 2017/12059; A61B 2017/12063;
(Continued)

(56) References Cited

U.S. PATENT DOCUMENTS 3,402,710 A    9/1968  Maurice
3,540,431 A    11/1970 Mobin-Uddin
(Continued)

FOREIGN PATENT DOCUMENTS

WO    9504132 A1    2/1995
WO    9601591 A1    1/1996
(Continued)

*Primary Examiner* — Tan-Uyen T Ho
*Assistant Examiner* — Chima U Igboko
(74) *Attorney, Agent, or Firm* — Seager, Tufte & Wickhem LLP

(57) ABSTRACT

An implant delivery system, comprising: an implantable device comprising a plurality of supports extending between a proximal end and a distal end, the supports being moveable between a collapsed configuration and an expanded configuration, a proximal guide tube at the proximal end of the supports extending toward the distal end, and a distal guide tube at the distal end of the supports extending toward the proximal end, wherein the proximal and distal guide tubes are telescoping and become further engaged as the supports move from the collapsed to the expanded configuration.

20 Claims, 28 Drawing Sheets

Related U.S. Application Data continuation of application No. 14/079,193, filed on Nov. 13, 2013, now abandoned, which is a continuation of application No. 13/436,700, filed on Mar. 30, 2012, now abandoned, which is a continuation of application No. 11/607,253, filed on Dec. 1, 2006, now abandoned.

(60) Provisional application No. 60/741,111, filed on Dec. 1, 2005.

(51) Int. Cl.
*A61F 2/01* (2006.01)
*A61B 17/22* (2006.01)
*A61B 17/04* (2006.01)

(52) U.S. Cl.
CPC ......... *A61B 17/12172* (2013.01); *A61F 2/01* (2013.01); *A61B 2017/00477* (2013.01); *A61B 2017/00575* (2013.01); *A61B 2017/00579* (2013.01); *A61B 2017/00592* (2013.01); *A61B 2017/00597* (2013.01); *A61B 2017/00619* (2013.01); *A61B 2017/00623* (2013.01); *A61B 2017/00632* (2013.01); *A61B 2017/00986* (2013.01); *A61B 2017/0412* (2013.01); *A61B 2017/0427* (2013.01); *A61B 2017/0464* (2013.01); *A61B 2017/1205* (2013.01); *A61B 2017/12054* (2013.01); *A61B 2017/12095* (2013.01); *A61B 2017/22038* (2013.01); *A61F 2/011* (2020.05)

(58) Field of Classification Search
CPC ........... A61B 2017/12068; A61B 2017/12072; A61B 2017/12077; A61B 2017/12081; A61B 2017/12086; A61B 2017/1209; A61B 2017/12095; A61B 17/12022; A61B 17/0057; A61B 17/12122; A61B 2017/00575; A61B 2017/00619; A61B 2017/00632; A61B 2017/00623; A61B 2017/00986; A61F 2002/011; A61F 2/01; A61F 2/011
See application file for complete search history.

(56) References Cited

U.S. PATENT DOCUMENTS

| | | |
|---|---|---|
| 3,557,794 A | 1/1971 | Van Patten |
| 3,638,652 A | 2/1972 | Kelley |
| 3,844,302 A | 10/1974 | Klein |
| 3,874,388 A | 4/1975 | King et al. |
| 4,007,743 A | 2/1977 | Blake |
| 4,284,488 A | 8/1981 | Brittain et al. |
| 4,309,776 A | 1/1982 | Berguer |
| 4,341,218 A | 7/1982 | Ü |
| 4,603,693 A | 8/1986 | Conta et al. |
| 4,611,594 A | 9/1986 | Grayhack et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,793,348 A | 12/1988 | Palmaz |
| 4,819,751 A | 4/1989 | Shimada et al. |
| 4,832,055 A | 5/1989 | Palestrant |
| 4,917,089 A | 4/1990 | Sideris |
| 4,921,484 A | 5/1990 | Hillstead |
| 5,041,090 A | 8/1991 | Scheglov et al. |
| 5,042,707 A | 8/1991 | Taheri |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metals |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,375,612 A | 12/1994 | Cottenceau et al. |
| 5,397,355 A | 3/1995 | Marin et al. |
| 5,417,699 A | 5/1995 | Klein et al. |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,490,856 A | 2/1996 | Person et al. |
| 5,522,790 A | 6/1996 | Moll et al. |
| 5,522,834 A | 6/1996 | Fonger et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer et al. |
| 5,584,805 A | 12/1996 | Sutton |
| 5,614,204 A | 3/1997 | Cochrum |
| 5,634,936 A | 6/1997 | Linden et al. |
| 5,634,942 A | 6/1997 | Chevillon et al. |
| 5,643,282 A | 7/1997 | Kieturakis |
| 5,643,292 A | 7/1997 | Hart |
| 5,653,684 A | 8/1997 | Laptewicz et al. |
| 5,669,933 A | 9/1997 | Simon et al. |
| 5,693,067 A | 12/1997 | Purdy |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,894 A | 5/1998 | Engelson |
| 5,766,219 A | 6/1998 | Horton |
| 5,772,578 A | 6/1998 | Heimberger et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,814,064 A | 9/1998 | Daniel et al. |
| 5,830,228 A | 11/1998 | Knapp et al. |
| 5,836,968 A | 11/1998 | Simon et al. |
| 5,843,118 A | 12/1998 | Sepetka et al. |
| 5,849,005 A | 12/1998 | Garrison et al. |
| 5,853,422 A * | 12/1998 | Huebsch ............ A61B 17/0057 606/213 |
| 5,865,791 A | 2/1999 | Whayne et al. |
| 5,879,366 A | 3/1999 | Shaw et al. |
| 5,891,558 A | 4/1999 | Bell et al. |
| 5,904,680 A | 5/1999 | Kordis et al. |
| 5,906,207 A | 5/1999 | Shen |
| 5,906,209 A | 5/1999 | Tortal et al. |
| 5,911,734 A | 6/1999 | Tsugita et al. |
| 5,925,074 A | 7/1999 | Gingras et al. |

(56) References Cited

U.S. PATENT DOCUMENTS

| | | |
|---|---|---|
| 5,925,075 A | 7/1999 | Myers et al. |
| 5,928,260 A | 7/1999 | Chin et al. |
| 5,935,145 A | 8/1999 | Villar et al. |
| 5,935,148 A | 8/1999 | Villar et al. |
| 5,941,896 A | 8/1999 | Kerr |
| 5,951,599 A | 9/1999 | McCrory |
| 5,954,715 A | 9/1999 | Harrington et al. |
| 5,961,545 A | 10/1999 | Lentz et al. |
| 5,993,483 A | 11/1999 | Gianotti |
| 6,004,348 A | 12/1999 | Banas et al. |
| 6,007,557 A | 12/1999 | Ambrisco et al. |
| 6,013,093 A | 1/2000 | Nott et al. |
| 6,024,756 A | 2/2000 | Huebsch et al. |
| 6,053,922 A | 4/2000 | Krause et al. |
| 6,053,933 A | 4/2000 | Balazs et al. |
| 6,056,200 A | 5/2000 | Dvorkis et al. |
| 6,056,770 A | 5/2000 | Epstein et al. |
| 6,063,070 A | 5/2000 | Eder |
| 6,066,157 A | 5/2000 | Barbere |
| 6,076,012 A | 6/2000 | Swanson et al. |
| 6,079,414 A | 6/2000 | Roth |
| 6,080,182 A | 6/2000 | Shaw et al. |
| 6,096,053 A | 8/2000 | Bates et al. |
| 6,110,243 A | 8/2000 | Wnenchak et al. |
| 6,117,159 A | 9/2000 | Kluebsch et al. |
| 6,124,523 A | 9/2000 | Banas et al. |
| 6,132,438 A | 10/2000 | Fleischman et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,165,200 A | 12/2000 | Tsugita et al. |
| 6,171,329 B1 | 1/2001 | Shaw et al. |
| 6,179,859 B1 | 1/2001 | Bates et al. |
| 6,214,029 B1 | 4/2001 | Thill et al. |
| 6,231,561 B1 | 5/2001 | Frazier et al. |
| 6,231,589 B1 | 5/2001 | Wessman et al. |
| 6,234,458 B1 | 5/2001 | Gerhardy |
| 6,251,122 B1 | 6/2001 | Tsukernik |
| 6,258,115 B1 | 7/2001 | Dubrul |
| 6,270,530 B1 | 8/2001 | Eldridge et al. |
| 6,270,902 B1 | 8/2001 | Tedeschi et al. |
| 6,273,876 B1 | 8/2001 | Klima et al. |
| 6,277,138 B1 | 8/2001 | Levinson et al. |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,458,151 B1 | 10/2002 | Saltiel |
| 6,468,291 B2 | 10/2002 | Bates et al. |
| 6,468,301 B1 | 10/2002 | Amplatz et al. |
| 6,511,496 B1 | 1/2003 | Huter et al. |
| 6,514,280 B1 | 2/2003 | Gilson |
| 6,517,573 B1 | 2/2003 | Pollock et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,589,251 B2 | 7/2003 | Yee et al. |
| 6,599,308 B2 | 7/2003 | Amplatz |
| 6,623,508 B2 | 9/2003 | Shaw et al. |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,699,276 B2 | 3/2004 | Sogard et al. |
| 6,709,415 B2 | 3/2004 | Navia et al. |
| 6,716,207 B2 | 4/2004 | Farnholtz |
| 6,726,701 B2 | 4/2004 | Gilson et al. |
| 6,730,108 B2 | 5/2004 | Van Tassel et al. |
| 6,749,583 B2 | 6/2004 | Briscoe et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,866,677 B2 | 3/2005 | Douk et al. |
| 6,921,397 B2 | 7/2005 | Corcoran et al. |
| 6,932,838 B2 | 8/2005 | Schwartz et al. |
| 6,936,058 B2 | 8/2005 | Forde et al. |
| 6,949,113 B2 | 9/2005 | Van Tassel et al. |
| 6,994,092 B2 | 2/2006 | van der Burg et al. |
| 7,011,671 B2 | 3/2006 | Welch |
| 7,044,134 B2 | 5/2006 | Khairkhahan et al. |
| 7,128,073 B1 | 10/2006 | Burg et al. |
| 7,128,752 B2 | 10/2006 | Bales |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,344,545 B2 | 3/2008 | Takemoto et al. |
| 7,500,957 B2 | 3/2009 | Bledsoe |
| 7,550,003 B2 | 6/2009 | Sogard et al. |
| 7,597,704 B2 | 10/2009 | Frazier et al. |
| 7,618,425 B2 | 11/2009 | Yamamoto et al. |
| 7,625,364 B2 | 12/2009 | Corcoran et al. |
| 7,651,513 B2 | 1/2010 | Teoh et al. |
| 7,658,748 B2 | 2/2010 | Marino et al. |
| 7,713,282 B2 | 5/2010 | Frazier et al. |
| 7,735,493 B2 | 6/2010 | van der Burg et al. |
| 7,753,906 B2 | 7/2010 | Esposito |
| 7,780,646 B2 | 8/2010 | Farnholtz |
| 7,799,049 B2 | 9/2010 | Ostrovsky et al. |
| 8,016,869 B2 | 9/2011 | Nikolchev |
| 8,080,032 B2 | 12/2011 | van der Burg et al. |
| 8,162,974 B2 | 4/2012 | Eskuri et al. |
| 8,216,256 B2 | 7/2012 | Raschdort et al. |
| 8,287,563 B2 | 10/2012 | Khairkhahan et al. |
| 8,323,309 B2 | 12/2012 | Khairkhahan et al. |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0177840 A1 | 11/2002 | Farnholtz |
| 2002/0178570 A1 | 12/2002 | Sogard et al. |
| 2003/0017775 A1 | 1/2003 | Sowinski et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181924 A1 | 9/2003 | Yamamoto et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0212432 A1 | 11/2003 | Khairkhahan et al. |
| 2003/0220667 A1 | 11/2003 | van der Burg et al. |
| 2004/0024417 A1 | 2/2004 | Akerfeldt |
| 2004/0034366 A1 | 2/2004 | van der Burg et al. |
| 2004/0044361 A1 | 3/2004 | Frazier et al. |
| 2004/0098031 A1 | 5/2004 | van der Burg et al. |

(56) References Cited

U.S. PATENT DOCUMENTS

| | | |
|---|---|---|
| 2004/0122466 A1 | 6/2004 | Bales |
| 2004/0147941 A1 | 7/2004 | Takemoto et al. |
| 2004/0176741 A1 | 9/2004 | Famholtz |
| 2004/0199175 A1 | 10/2004 | Jaeger et al. |
| 2004/0215230 A1* | 10/2004 | Frazier ............. A61B 17/12122 606/200 |
| 2004/0220585 A1 | 11/2004 | Nikolchev |
| 2004/0220610 A1 | 11/2004 | Kreidler et al. |
| 2005/0038470 A1 | 2/2005 | van der Burg et al. |
| 2005/0043711 A1 | 2/2005 | Corcoran et al. |
| 2005/0177082 A1 | 8/2005 | van der Burg et al. |
| 2005/0177182 A1 | 8/2005 | van der Burg et al. |
| 2005/0192625 A1 | 9/2005 | Akerfeldt |
| 2005/0273135 A1 | 12/2005 | Chanduszko et al. |
| 2006/0116714 A1 | 6/2006 | Sepetka et al. |
| 2006/0122647 A1* | 6/2006 | Callaghan .......... A61B 17/0057 606/213 |
| 2007/0123927 A1 | 5/2007 | Farnan |
| 2007/0135826 A1 | 6/2007 | Zaver et al. |
| 2012/0239077 A1 | 9/2012 | Zaver et al. |
| 2014/0081314 A1 | 3/2014 | Zaver et al. |
| 2015/0230909 A1 | 8/2015 | Zaver et al. |

FOREIGN PATENT DOCUMENTS

| | | |
|---|---|---|
| WO | 9640356 A1 | 12/1996 |
| WO | 9640956 A1 | 12/1996 |
| WO | 9735522 A1 | 10/1997 |
| WO | 9827868 A1 | 7/1998 |
| WO | 9923976 A1 | 5/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |
| WO | 0130266 A1 | 5/2001 |
| WO | 0130267 A1 | 5/2001 |
| WO | 0130268 A1 | 5/2001 |
| WO | 03007825 A1 | 1/2002 |
| WO | 0215793 A2 | 2/2002 |
| WO | 0224106 A2 | 3/2002 |
| WO | 02071977 A2 | 9/2002 |
| WO | 03008030 A2 | 1/2003 |

* cited by examiner

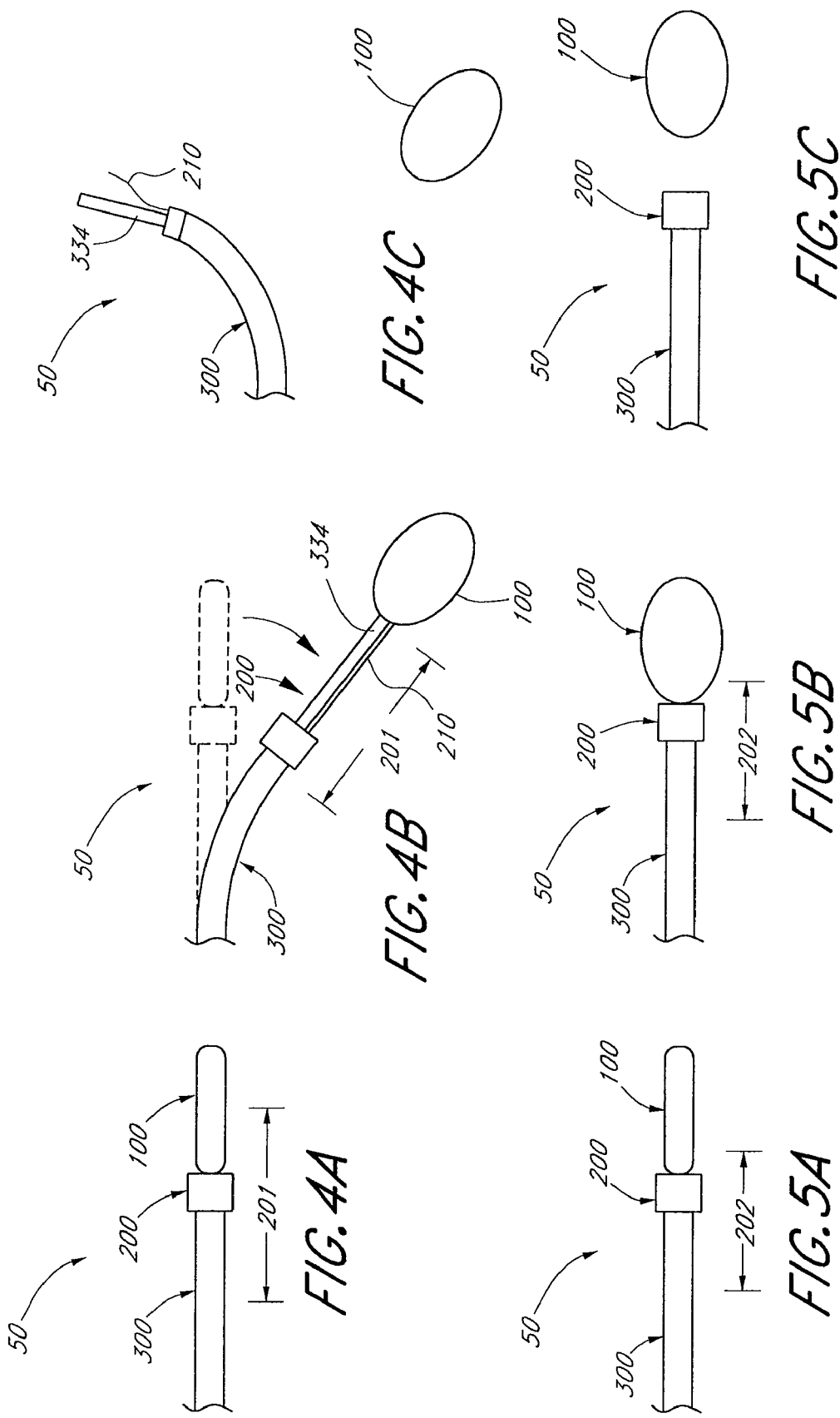

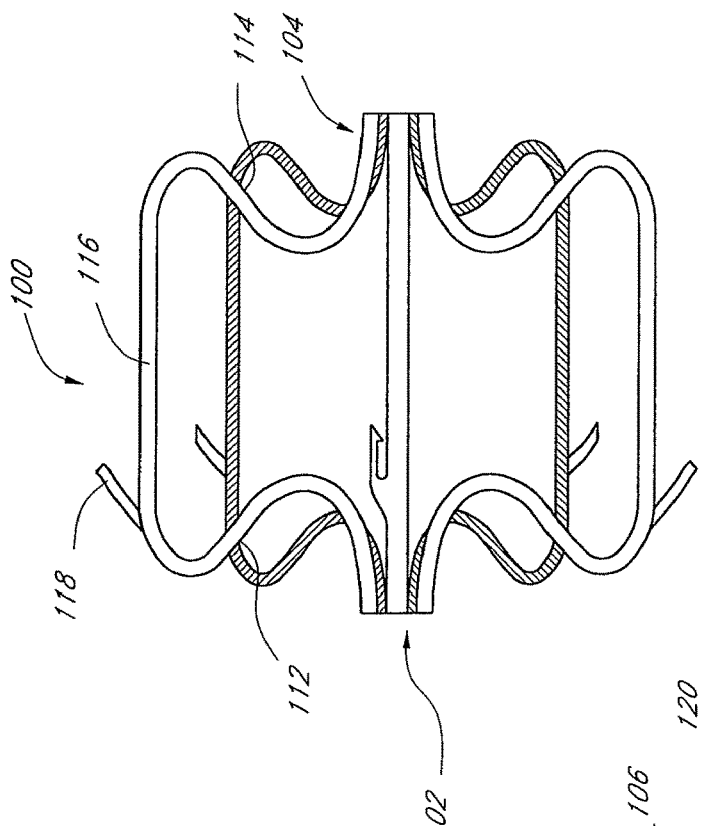
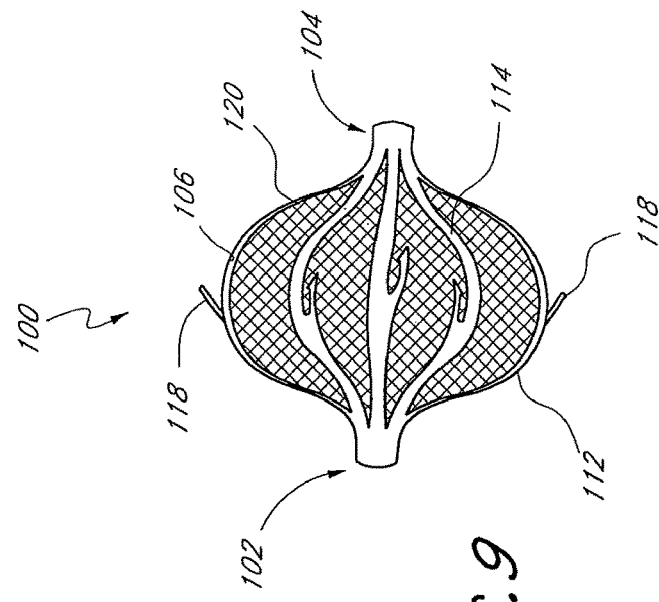
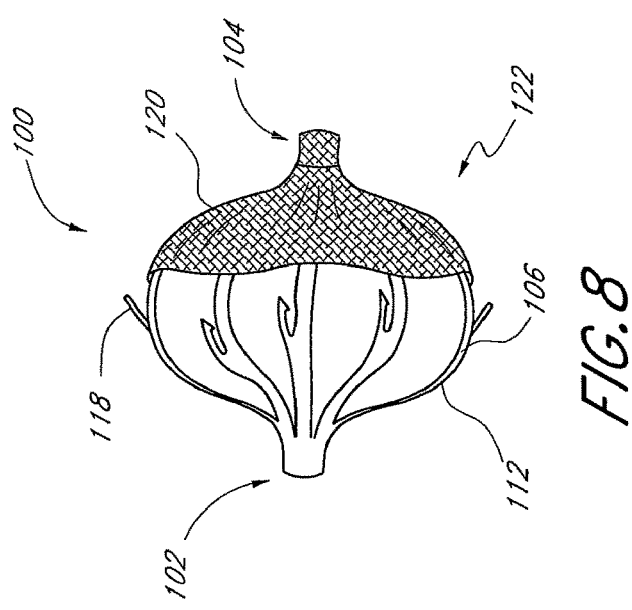
FIG. 10
FIG. 9
FIG. 8

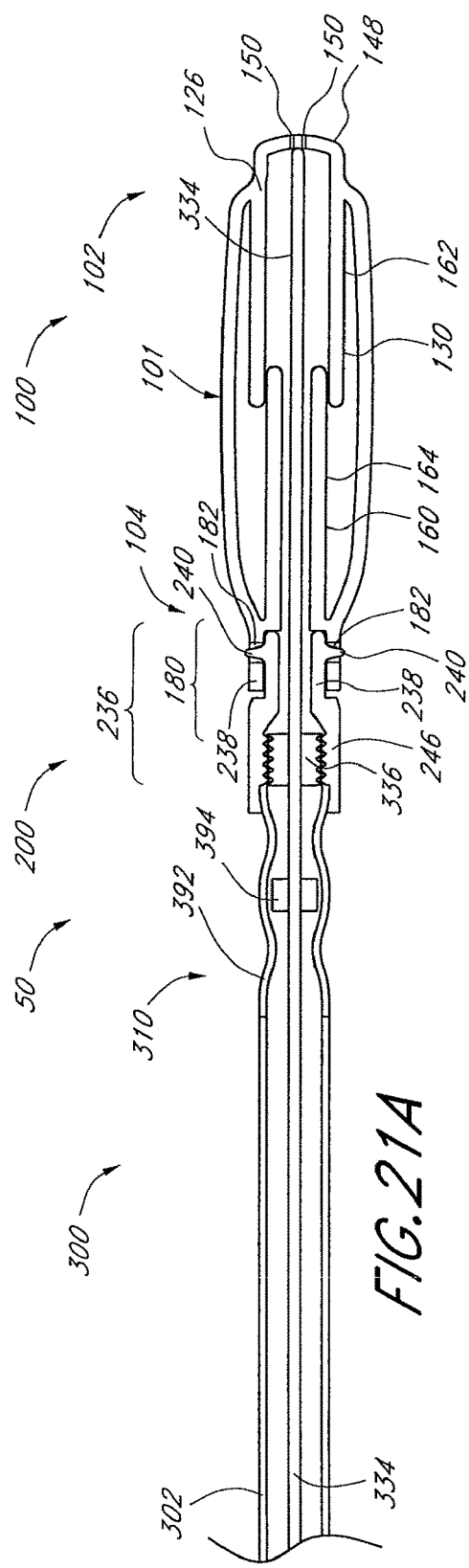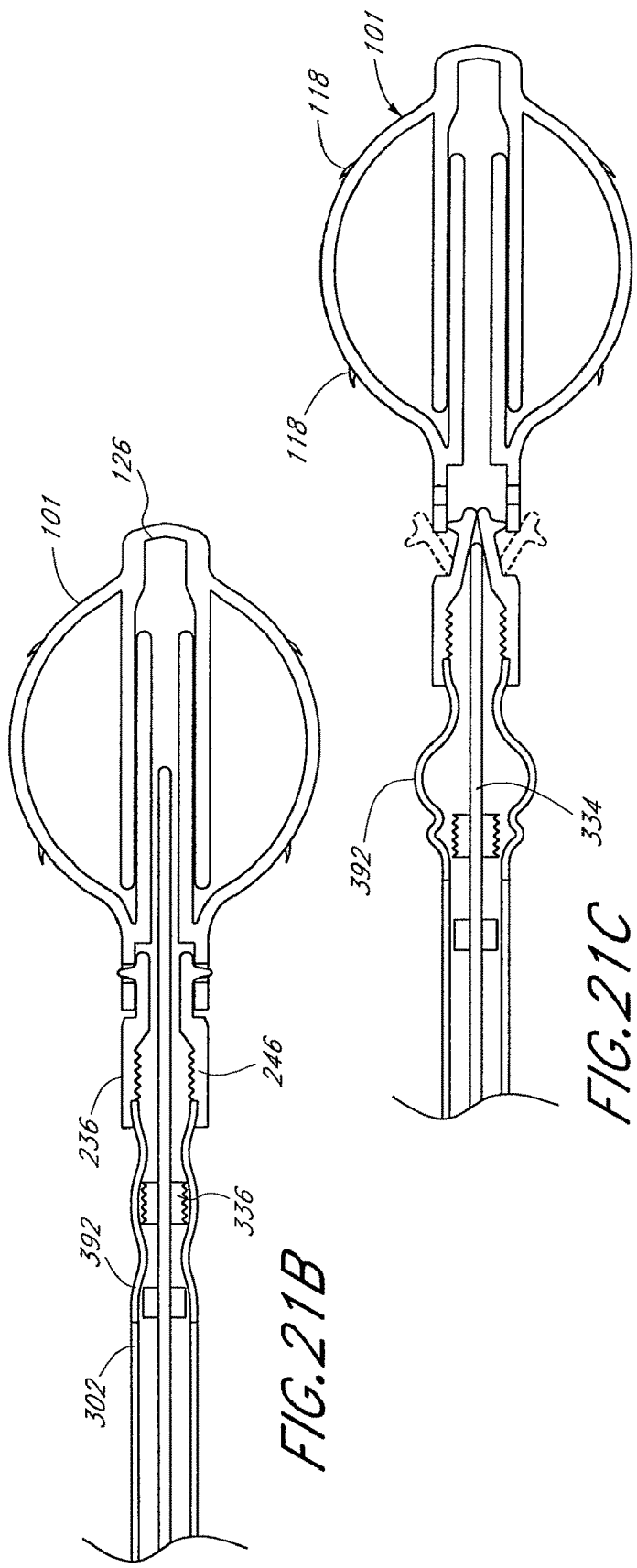
FIG.21A
FIG.21B
FIG.21C

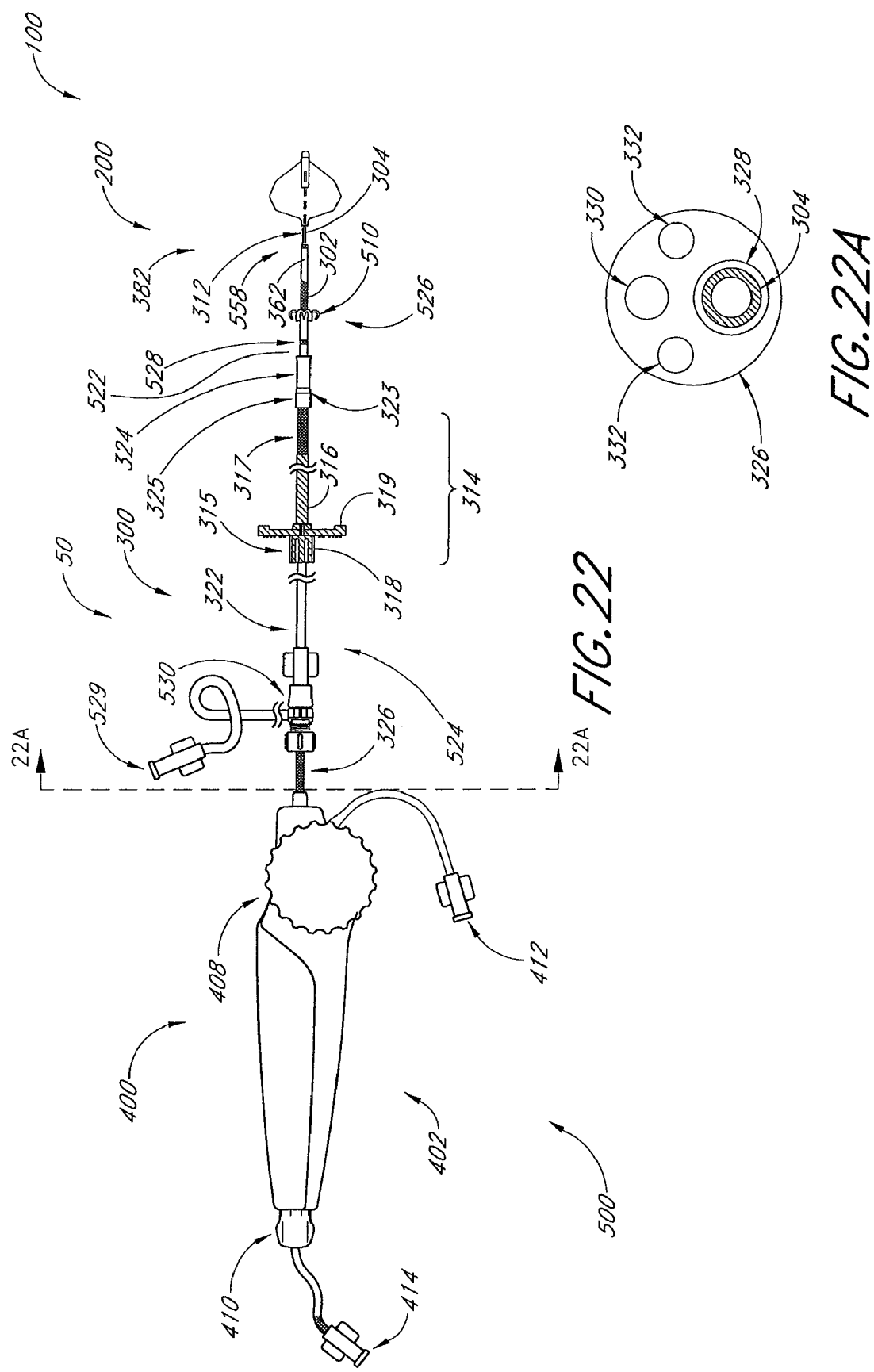

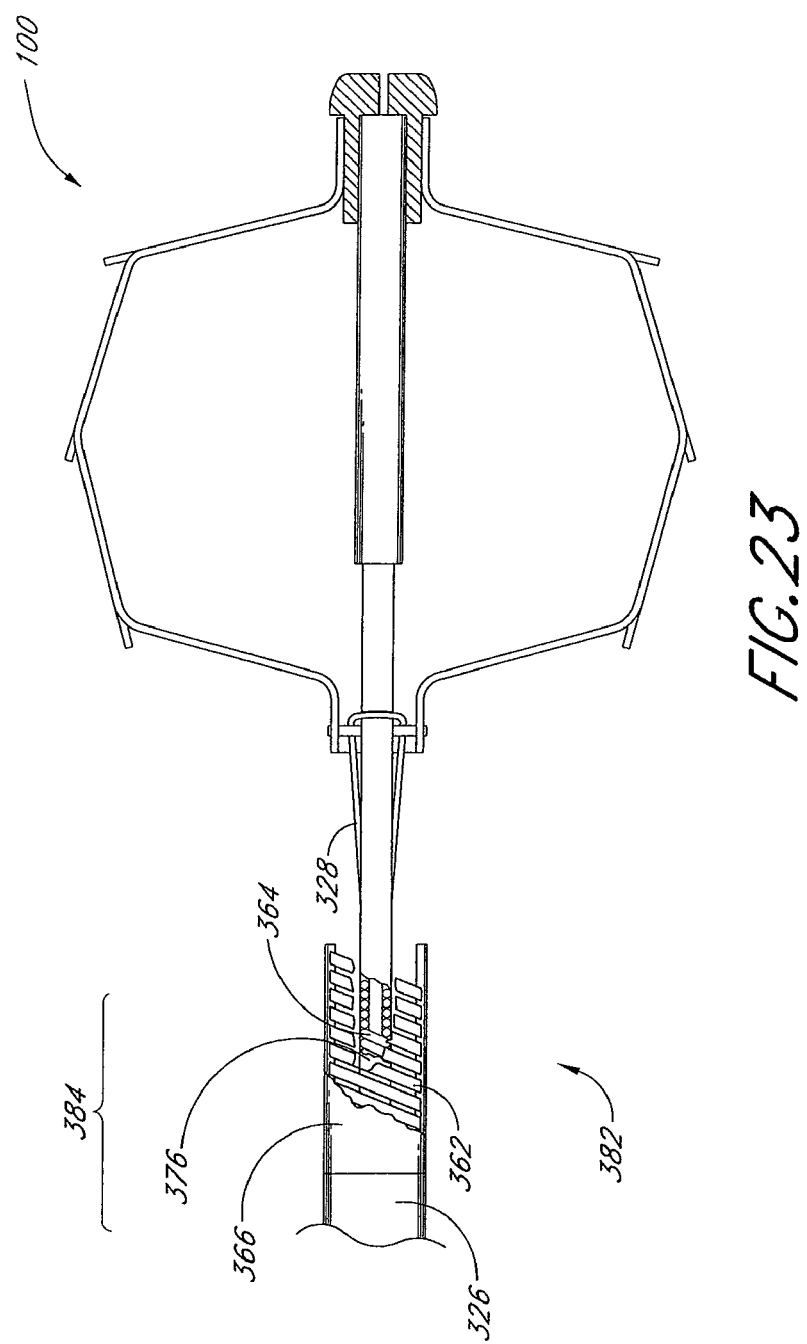

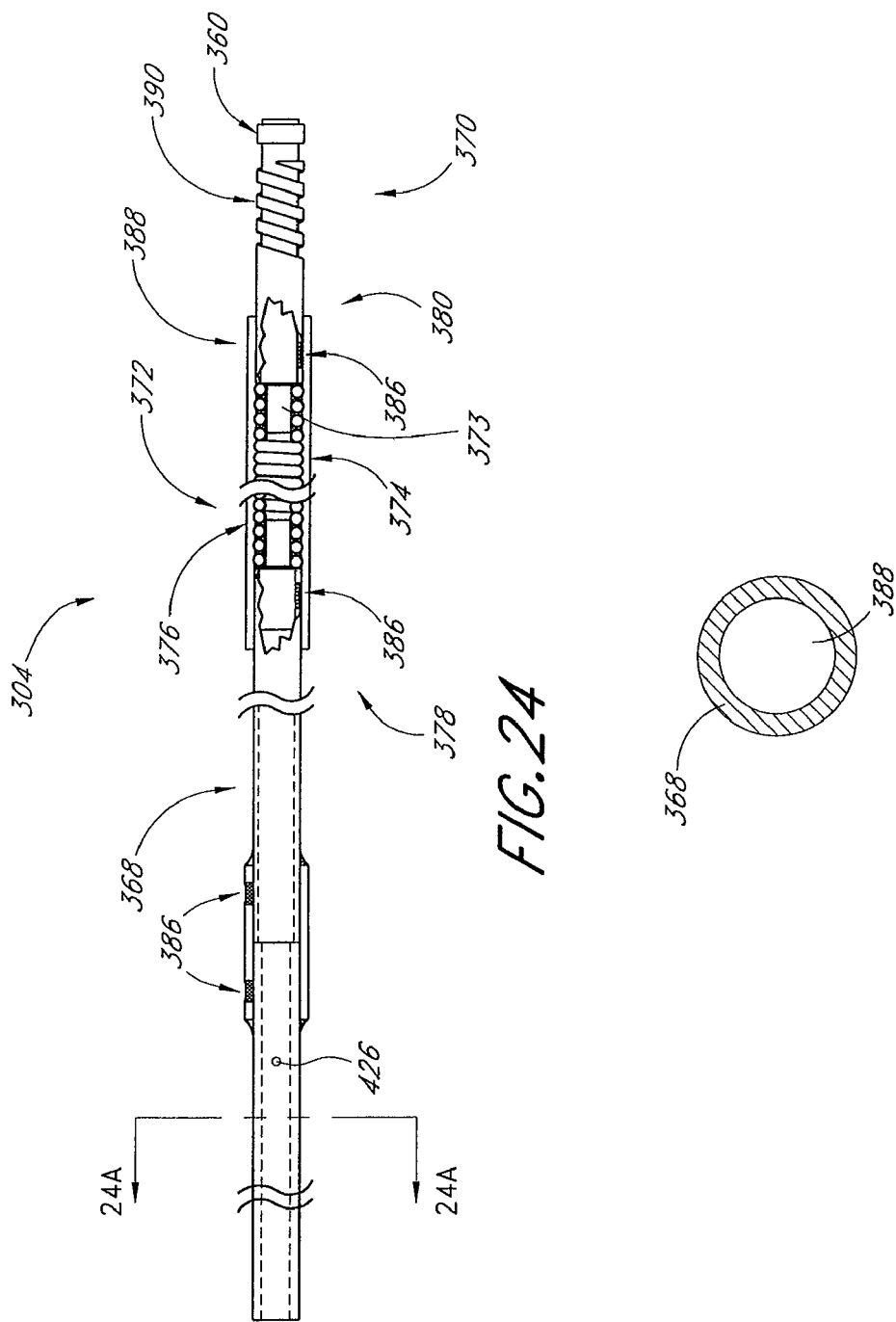

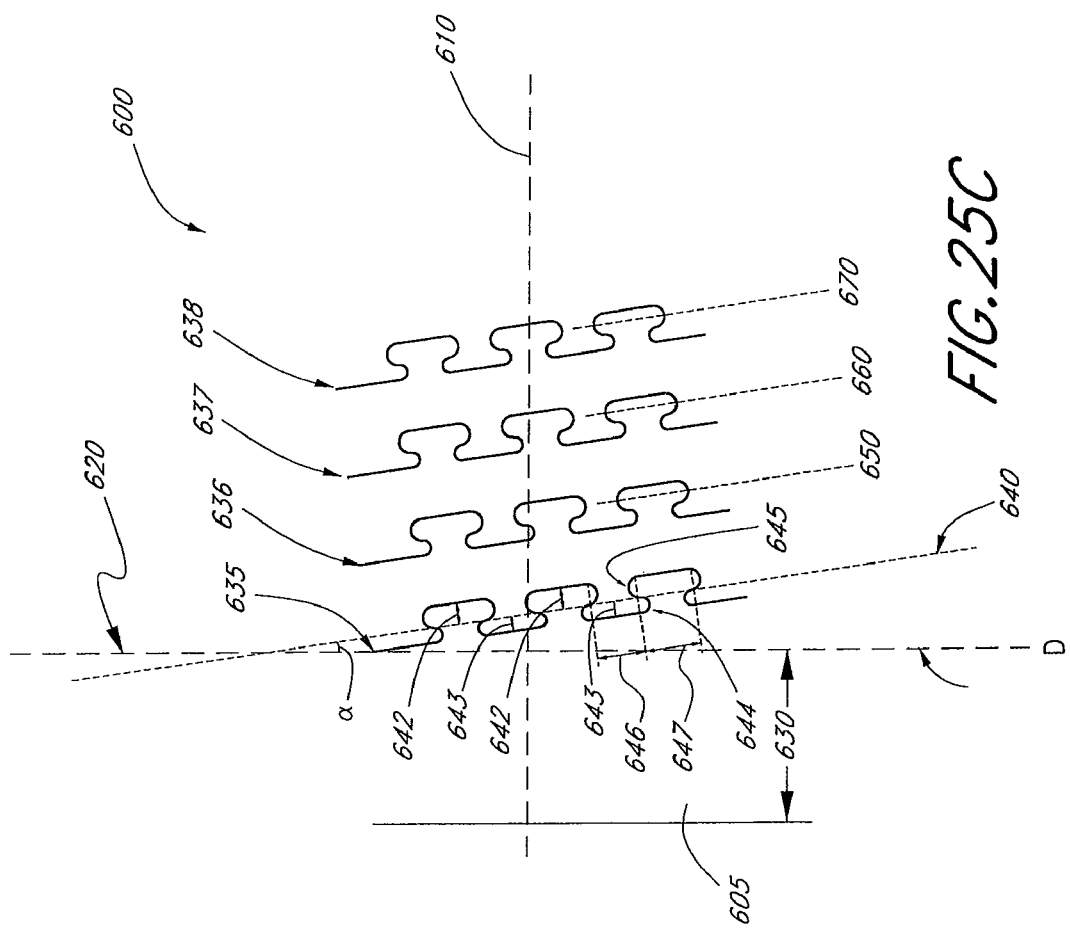
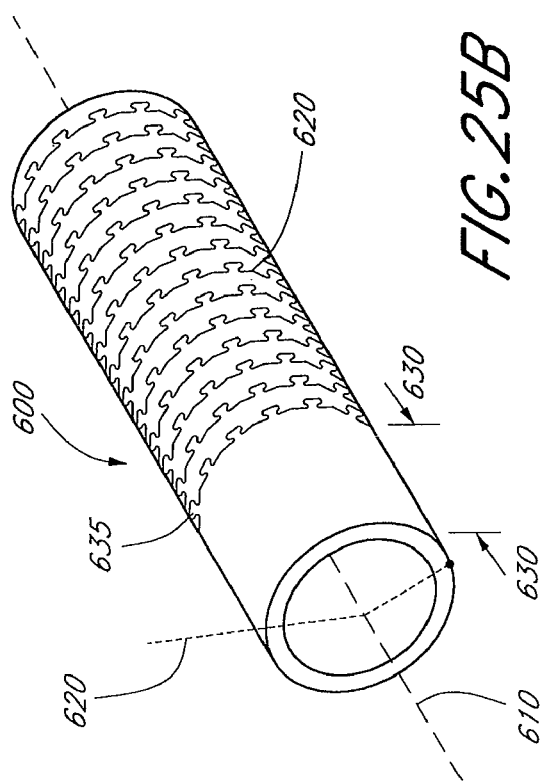

APPARATUS FOR DELIVERING AN IMPLANT WITHOUT BIAS TO A LEFT ATRIAL APPENDAGE

CROSS-REFERENCE TO RELATED U.S. APPLICATIONS

This application is a continuation of U.S. Ser. No. 14/705,561, filed May 6, 2015, which is a continuation of U.S. Ser. No. 14/079,193, filed Nov. 13, 2013, now abandoned, which is a continuation of U.S. Ser. No. 13/436,700, filed Mar. 30, 2012, now abandoned, which is a continuation of U.S. Ser. No. 11/607,253, filed Dec. 1, 2006, now abandoned, which claims the benefit of priority from U.S. Provisional No. 60/741,111, filed Dec. 1, 2005, each of which is incorporated by reference, herein.

BACKGROUND

Embolic stroke is the nation's third leading killer for adults, and is a major cause of disability. There are over 700,000 strokes per year in the United States alone. Of these, roughly 100,000 are hemorrhagic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with atrial fibrillation. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996. 61(2): 755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996. 61(2): 515.

During surgical procedures, such as mitral valve repair, thrombus in the left atrial appendage may leave the LAA and enter the blood stream of a patient. The thrombus in the blood stream of the patient can cause embolic stroke. There are known techniques for closing off the LAA so that thrombus cannot enter the patient's blood stream. For example, surgeons have used staples or sutures to close the orifice of the LAA, such that the closed off LAA surrounds the thrombus. Unfortunately, using staples or sutures to close off the LAA may not completely close the orifice of the LAA. Thus, thrombus may leave the LAA and enter the patient's blood stream, even though the LAA is closed with staples or sutures. Additionally, closing the orifice of the LAA by using staples or sutures may result in discontinuities, such as folds or creases, in the endocardial surface facing the left atrium. Unfortunately, blood clots may form in these discontinuities and can enter the patient's blood stream, thereby causing health problems. Moreover, it is difficult to place sutures at the orifice of the LAA and may result in a residual appendage. For example, an epicardial approach to ligate sutures can result in a residual appendage. Similarly, thrombus may form in the residual appendage and enter the patient's blood stream causing health problems.

Despite the various efforts in the prior art, there remains a need for a minimally invasive method and associated devices for reducing the risk of thrombus formation in the left atrial appendage. Various implantable devices and methods of delivery have been previously described. However, some delivery devices can have limited flexibility and can provide off-axis loading that creates moment arms and bending bias. Moment arms and bending bias can cause the implant to "jump" or move within the left atrial appendage when it is detached from the implant delivery system. Therefore, it would be advantageous for a left atrial appendage implantation to system to avoid moment arms and bending bias such that when the implant is released it remains in the position it had when coupled to the delivery system.

SUMMARY OF THE INVENTION

There is provided in accordance with one embodiment of the present invention a system and method for minimizing, reducing, substantially eliminating, and/or eliminating implantation bias during delivery of an implant. The system includes an implant with a distal guide tube, an actuation shaft, and a concentrically attachable disconnect mount. In one embodiment the implant is configured to contain emboli with a left atrial appendage of a heart of a patient. The implantable device has a proximal and distal end with a plurality of supports and is moveable between a collapsed and an expanded configuration. The distal guide tube at the distal end of the supports extends toward the proximal end of the implant. The actuation shaft extends through the proximal end of the implantable device and is removeably engageable with the distal guide tube. The disconnect mount is releasably engageable with the proximal end of the implant and is concentrically attachable to the proximal end of the implant. In one embodiment, the implant is self-expandable. In another embodiment, the implant is collapsed by engaging the actuation shaft with the distal guide tube while applying a relatively proximal force to the proximal end of the implant with the disconnect mount.

In one embodiment of the present invention, an implant delivery system includes an implantable device, a proximal guide tube, and a distal guide tube. The implantable device has a plurality of supports extending between a proximal end and a distal end. The supports are moveable between a collapsed configuration and an expanded configuration.

In one embodiment, the proximal guide tube is located at the proximal end of the supports and extends toward the distal end of the device. The distal guide tube is located at the distal end of the supports and extends toward the proximal end of the device. The proximal and distal guide tubes are telescoping and become further engaged as the supports move from the collapsed to the expanded configuration.

In another embodiment of the present invention, an implant delivery system includes an implantable device, an actuation shaft, and a disconnect mount. In some embodiments, the implant delivery system further comprises a distal guide tube. The implantable device has a proximal end, a distal end, and a plurality of supports extending therebetween. The implantable device is moveable between a collapsed configuration and an expanded configuration.

In one embodiment, the distal guide tube, when provided, is located at the distal end of the supports and extends toward the proximal end of the device. The actuation shaft is extendable through the proximal end of the implantable device and is removeably engageable with the distal guide tube. The disconnect mount is releasably engageable with the proximal end of the implantable device. The disconnect mount is concentrically attachable to the proximal end of the implantable device.

In some embodiments, the implantable device is self-expanding. In other embodiments, the implantable device is collapsed by engaging the actuation shaft with the distal guide tube while applying a relatively proximal force to the proximal end of the implantable device with the disconnect mount.

In yet another embodiment of the present invention, a method of actuating an implantable device with a concentric force includes providing an implantable device, applying a concentric force, and applying a distal force. The implantable device has a proximal end, a distal end, and a plurality of supports extending therebetween. The implantable device is configured to expand from a reduced-diameter configuration to an expanded-diameter configuration. In one embodiment, the concentric force is applied to the proximal end. In other embodiments, the distal force is applied to the distal end.

BRIEF DESCRIPTION OF THE DRAWINGS

FIG. 4A is a side elevational view of the distal end of the implant delivery system shown in FIG. 3A with a radially-reduced implant;

FIG. 4B is a side elevational view of the distal end of the implant delivery system shown in FIG. 4A with a radially-expanded implant;

FIG. 4C is a side elevational view of the distal end of an implant delivery system shown in FIG. 4B with a released radially-expanded implant;

FIG. 5A is a side elevational view of the distal end of the implant delivery system shown in FIG. 3B with a radially-reduced implant;

FIG. 5B is a side elevational view of the distal end of the implant delivery system shown in FIG. 5A with a radially-expanded implant;

FIG. 5C is a side elevational view of the distal end of an implant delivery system shown in FIG. 5B with a released radially-expanded implant;

FIGS. 8 and 9 are side elevational schematic representations of partial and complete barrier layers of the containment device of FIG. 7;

FIG. 10 is a side elevational schematic view of an alternate containment device in accordance with another embodiment of the present invention;

FIGS. 21A-C are schematic cross-sectional views of an embodiment of an implant release and recapture mechanism having a threaded portion of an implant actuation shaft, in accordance with another embodiment;

FIG. 22 is a schematic view of a delivery system in accordance with one embodiment of the present invention;

FIG. 22A is a cross-sectional view of an implant delivery system as shown in FIG. 22, taken along line 22A-22A;

FIG. 23 is a partial cross-sectional view of the distal end of a deployment system constructed in accordance with one embodiment of the present invention;

FIG. 24 is a partial cross-sectional view of an axially moveable core used in the system of FIG. 22;

FIG. 24A is a cross-sectional view of the axially moveable core of FIG. 24 taken along line 24A-24A;

FIG. 25B is a perspective view of a tube with the puzzle lock profile of FIG. 25A; and FIG. 25C is a close up of the puzzle lock profile of FIG. 25B.

DETAILED DESCRIPTION OF CERTAIN PREFERRED EMBODIMENTS

Figure 1:
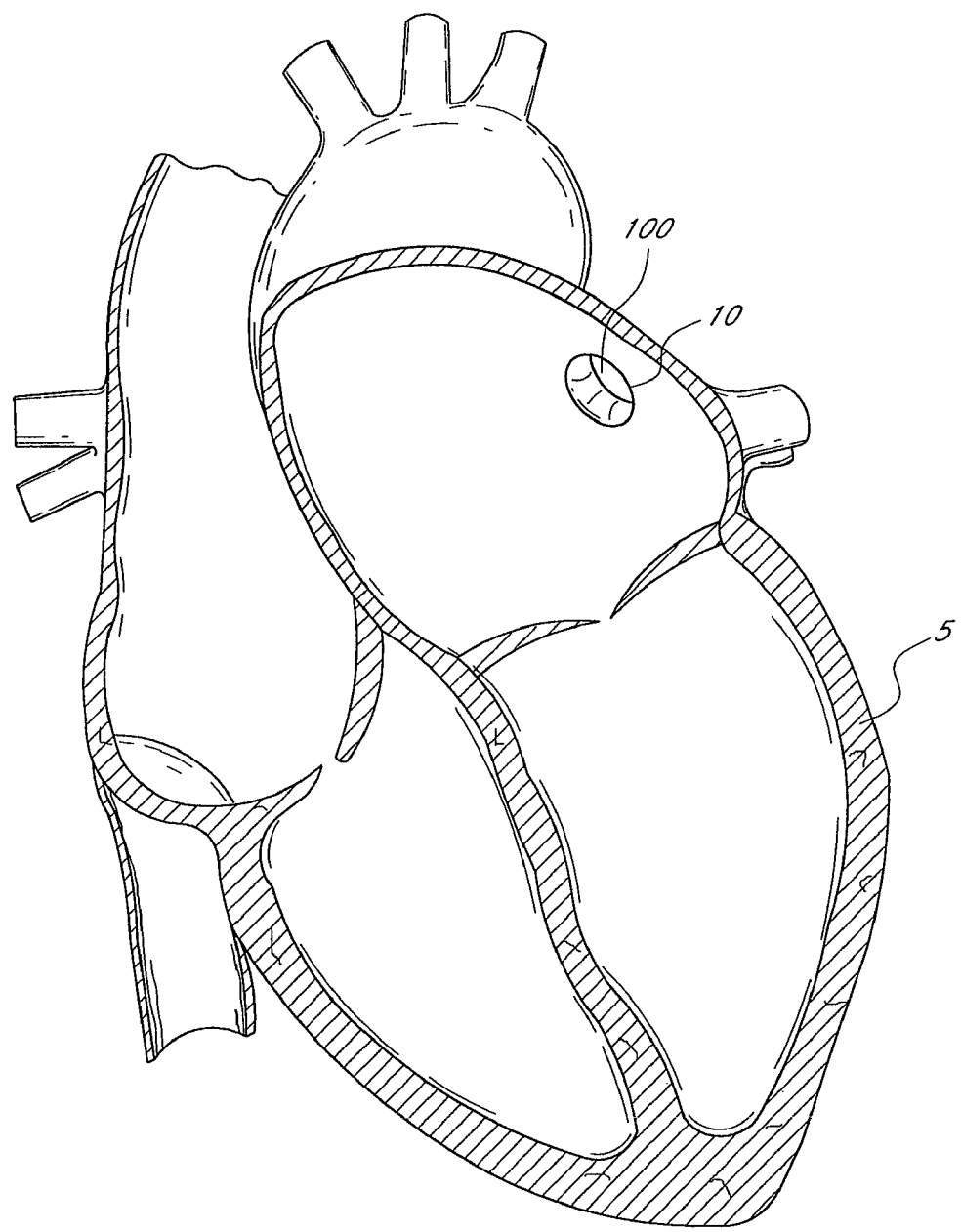
FIG. 1 is a view of a heart and its left atrial appendage.

FIG. 1 illustrates a sectional view of a heart 5 and its left atrial appendage (LAA) 10. An implant 100 is provided at least partially within the LAA 10. The terms "implant", "occlusion device" or "containment device" are broad terms intended to have their ordinary meaning. In addition, these terms are intended to refer to devices that are inserted into the body. Such devices may include a membrane, barrier and/or cover, or may omit these portions. Embodiments of the invention may also be used to treat other bodily openings, lumen and cavities, besides the LAA 10. For example, in some embodiments, the methods, devices and systems described herein are used to treat any heart opening or defect, such as a patent foramen ovale (PFO), an atrial septal defect (ASD), a ventricular septal defect (VSD), a patent ductus arteriosus (PDA), an aneurysm and/or an aortico-pulmonary window.

In various embodiments, an implant 100 can be delivered in a number of ways, e.g., using conventional transthoracic surgical, minimally invasive, or port access approaches. Delivery can be made or done in conjunction with surgical procedures as well. In one embodiment, the implant 100 is used in conjunction with various surgical heart procedures related to the heart (e.g., mitral valve repair) or surgical procedures in the region surrounding the heart. The delivery system can be used to locate and deploy the implant 100 in order to prevent the passage of embolic material from the LAA 10, such that thrombus remains contained in the LAA 10. Thrombus remains contained in the LAA 100 because the implant 100 inhibits thrombus within the LAA 10 from passing through the orifice of the LAA 10 and into the patient's blood stream. Additionally, the deployed implant 100 located in the LAA 10 can provide a smooth, non-thrombogenic surface facing the left atrium. In one embodiment, the smooth, non-thrombogenic surface facing the left atrium will not promote blood clots to form proximate to the LAA 10. Access to the heart may be provided by surgical procedures in order to deploy the implant 100 in the LAA 10. That is, the implant 100 can be deployed as an adjunct to surgical procedures. Various methods for accessing the LAA 10 and delivering an implant 100 to the LAA 10 are disclosed in U.S. application Ser. No. 11/003,696, filed Dec. 3, 2004, published as U.S. Publication No. 2005-0177182 A1, which is incorporated by reference herein.

A. Implant Delivery System

Figure 2:
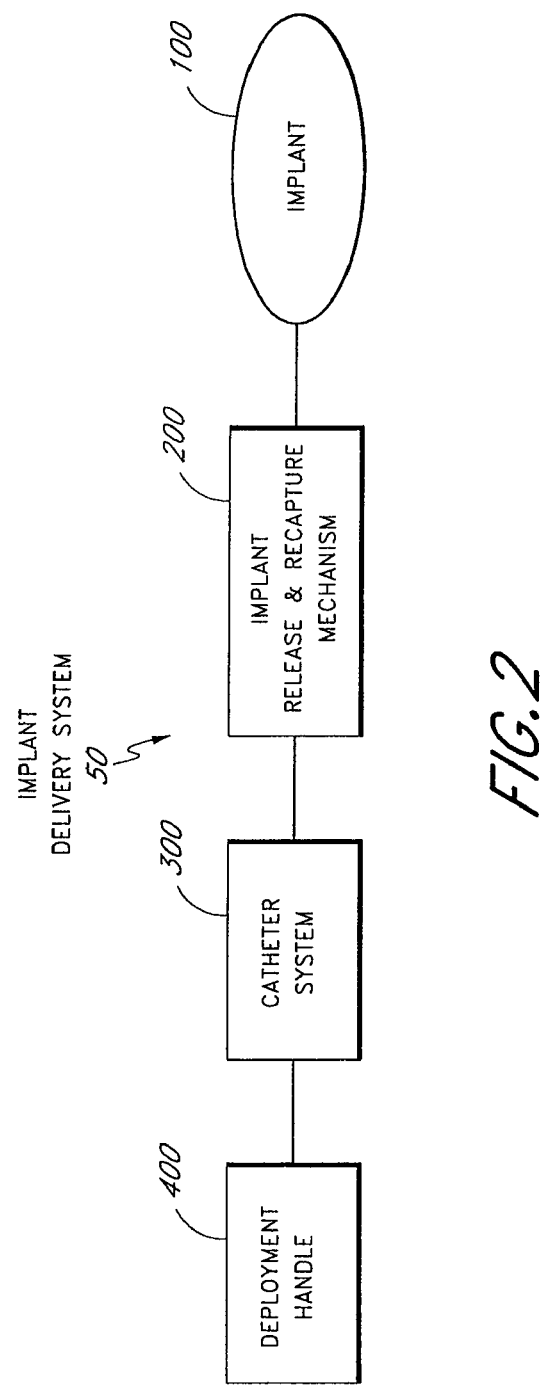
FIG. 2 is a block diagram representing a simplified implant delivery system in accordance with one embodiment of the present invention.

FIG. 2 illustrates a block diagram of an implant delivery system 50. The implant delivery system 50 includes an implant 100, an implant release and recapture mechanism 200, a catheter system 300 and a deployment handle 400. In some embodiments, the implant release and recapture mechanism 200 is the distal portion of the catheter system 300 and the deployment handle 400 is the proximal portion of the catheter system 300. The implant release and recapture mechanism 200 generally couples the implant 100 to the catheter system 300. The deployment handle 400 generally provides all the user controls and actuators of the implant delivery system 50.

Figure 2A:
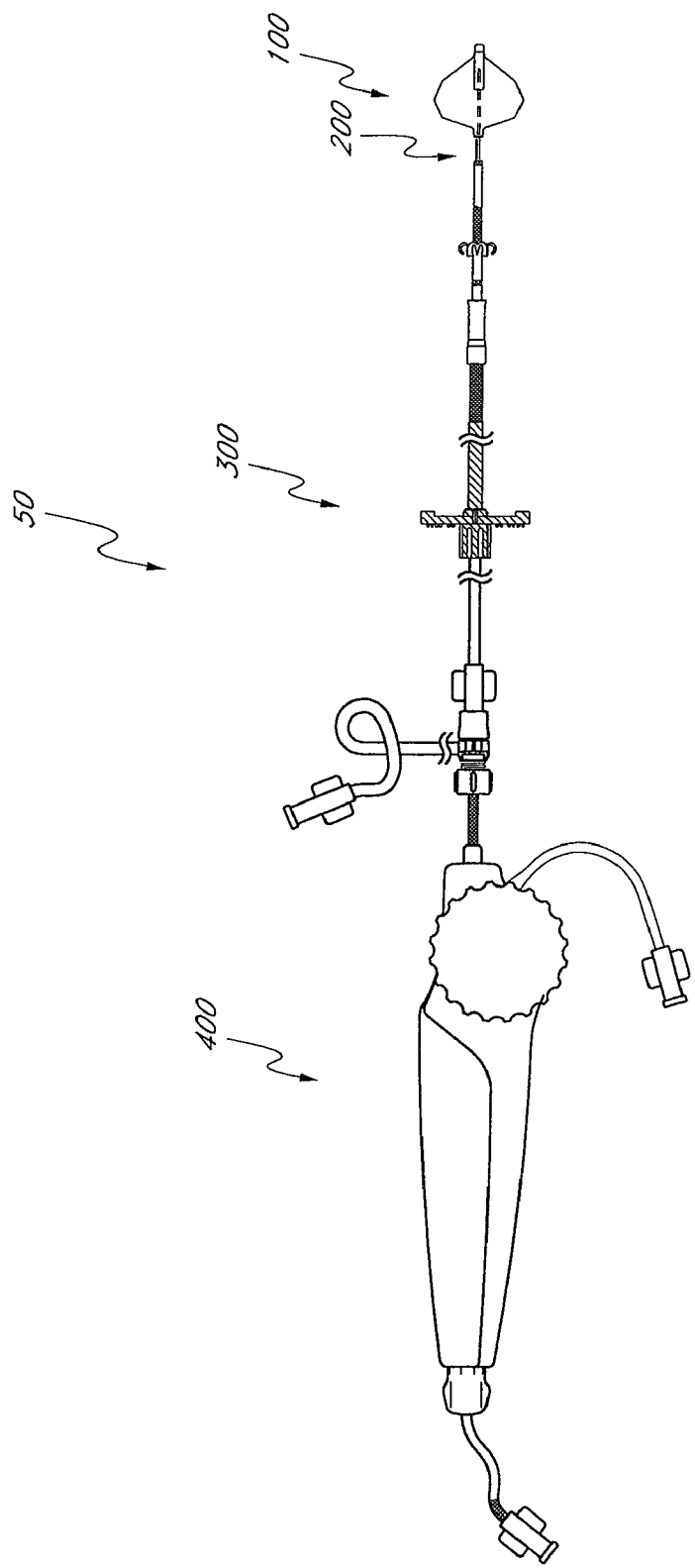
FIG. 2A is a schematic view of one embodiment of the delivery system of FIG. 2.

FIG. 2A illustrates one embodiment of the implant delivery system 50 of FIG. 2. The implant delivery system 50 includes an implant release and recapture mechanism 200 that is flexible and without bias. In this manner, when the implant 100 is released from the delivery system 50, the implant 100 maintains the position and orientation it had when coupled to the delivery system 50, and does not spring, jump, or move, as described above.

Figure 3A:
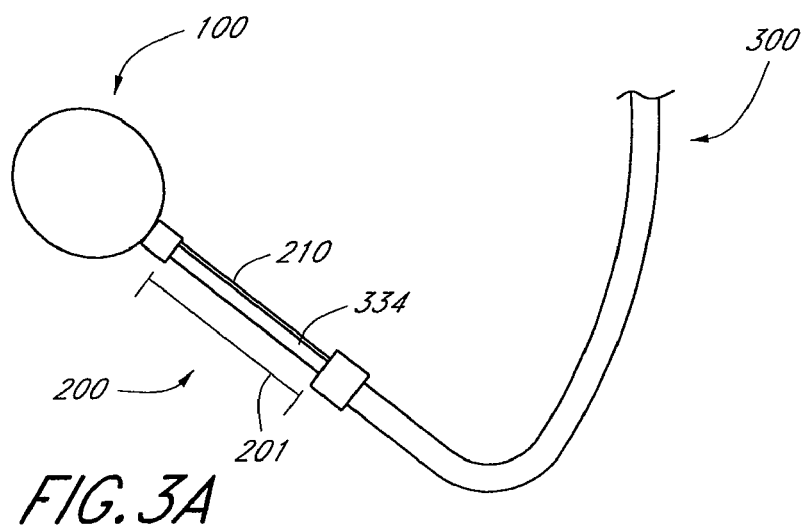
FIG. 3A is a side elevational view of the distal end of an embodiment of an implant delivery system.

FIG. 3A illustrates one example of an implant 100 (schematically shown) coupled to a catheter system 300 with an implant release and recapture mechanism 200. In the illustrated embodiment, the implant release and recapture mechanism 200 is relatively stiff and extends over a release mechanism length 201. The implant release and recapture mechanism 200 includes an implant actuation shaft 334 and a tether line 210. The implant 100 is generally self-expandable and is held in a reduced-diameter configuration by pushing against the distal end of the inside of the implant 100 while pulling on the implant's proximal end. For example, the implant actuation shaft 334 pushes against the implant distal end while the tether line 210 is held in tension to maintain the implant 100 in a reduced-diameter configuration. To expand the implant, tension on the tether line 210 is reduced and/or the implant actuation shaft 334 is moved proximally.

However, the implant actuation shaft 334 and tether line 210 can have limited flexibility and can provide off-axis loading that creates moment arms and bending bias. Deployment of the implant 100 in the confines of the heart 5 (not illustrated here) may require bending of the implant release and recapture mechanism 200, a catheter system 300, but stiffness along a release mechanism length 201 reduces flexibility and creates moment arm and bending bias.

Figure 3B:
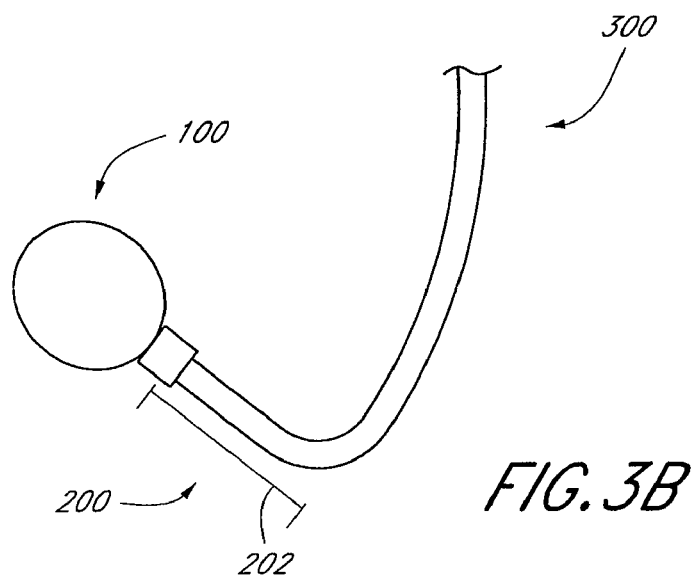
FIG. 3B is a side elevational view of the distal end of another embodiment of an implant delivery system.

FIG. 3B illustrates another embodiment of an implant 100 coupled to a catheter system 300 with an implant release and recapture mechanism 200. In the illustrated embodiment, the implant release and recapture mechanism 200 is relatively stiff and extends over a release mechanism length 202. The implant release and recapture mechanism 200 and the catheter system 300 are flexible and can be manipulated in order to access the LAA 10. When device stiffness or rigidity along a release mechanism length 202 is shorter than a release mechanism length 201, the device has increased flexibility and shorter moment arms, resulting in less bending bias.

FIGS. 4A-C illustrate the implant release sequence of the implant 100 with the implant release and recapture mechanism 200 of FIG. 3A. FIG. 4A illustrates an example of an implant 100, an implant release and recapture mechanism 200, and a catheter system 300 where the implant release and recapture mechanism 200 is relatively stiff and extends over a release mechanism length 201. FIG. 4B illustrates a catheter system 300 using an implant actuation shaft 334 and a tether line 210, which are used as components within the implant release and recapture mechanism 200. When the implant 100 is radially expanded the implant 100 can move axially toward the distal end of the implant 100, thereby exposing the implant actuation shaft 334 and tether line 210. The off-axis tension in the tether line 210 can create moment arms and bending bias which can cause the implant 100 to "jump," move, rotate, etc., within the LAA 10 when the implant 100 is detached from the implant delivery system, as is illustrated in FIG. 4C.

FIGS. 5A-C illustrate the implant release sequence of the implant 100 with the implant release and recapture mechanism 200 of FIG. 3B. FIG. 5A illustrates an example of an implant 100, an implant release and recapture mechanism 200, a catheter system 300 where the implant release and recapture mechanism 200 is relatively stiff and extends over a release mechanism length 202. Length 202 is shorter than length 201 of FIG. 4A. FIG. 5B illustrates the expansion of the implant 100 with shorter moment arms and less bending bias than the systems illustrated in FIGS. 4A-C. As illustrated in FIG. 5C, the release of the implant 100 from the catheter system 300 results in smaller moment arms and less bending bias than in FIGS. 4A-C. The detachment of the implant 100 results in less of a "jump" and reduced movement and/or rotation within the LAA 10.

1. Implant

Figure 6:
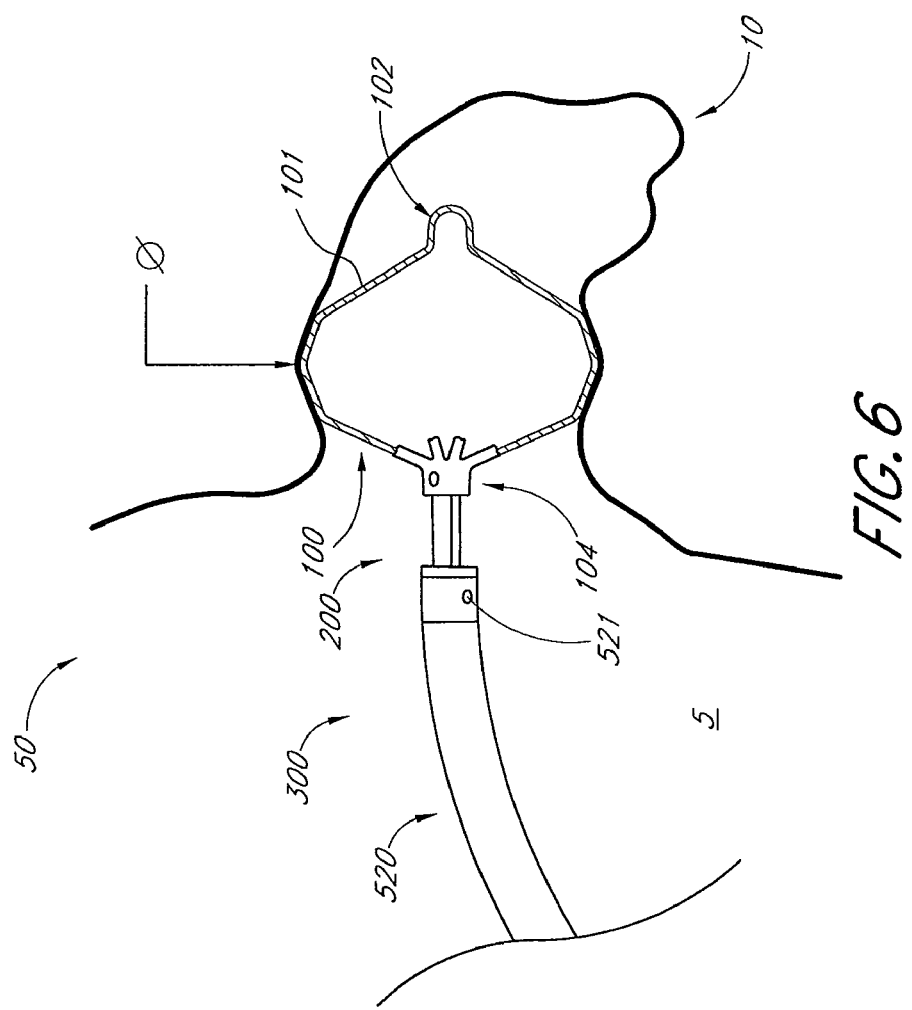
FIG. 6 is a schematic view of a deployment system delivering an implantable containment device to the left atrial appendage.

FIG. 6 illustrates an implant 100 placed inside a LAA 10 of a heart 5, an implant release and recapture mechanism 200, and a catheter system 300. In one embodiment, the implant 100 is a transluminally delivered device designed to occlude or contain particles within the LAA 10 and prevent thrombus from forming in, and emboli from originating from, the LAA 10. The delivery system 50 may be used to deliver the implant 100 to occlude or block the LAA 10 in a patient with atrial fibrillation. The delivery system 50 may be compatible for use with a transseptal sheath (not shown). The delivery system 50 and implant 100 may be selected to allow the implant 100 to be positioned, repositioned, and retrieved from the LAA 10 if necessary.

The implant 100 often includes a frame 101 and a membrane (not shown) on a proximal face 104 of the implant, such as described below. In an embodiment, the frame 101 is constructed of self-expanding nitinol supports. The membrane may be constructed of a fabric covering, such as one made of ePTFE, or an ePTFE/PE laminate. To attach the membrane to the frame 101, a PE mesh preferably is placed against the supports, with one sheet of ePTFE preferably placed over the PE mesh and another sheet of ePTFE preferably placed on an opposite side of the supports. The membrane may be heated on both sides causing the PE to melt into both sheets of ePTFE, thereby surrounding a portion of the frame 101. The nitinol supports allow the implant 100 to self-expand in the appendage 10, covering the orifice with the laminated fabric. The porous ePTFE/PE lamination facilitates rapid endothelialization and healing.

In one embodiment, the implant 100 is expandable and collapsible. The implant 100 can include anchors that extend from the implant's frame 101 when the implant 100 is expanded, as described below. The implant 100 is available in a range of sizes to accommodate the anatomy of a patient's LAA 10. When used in the LAA 10, the implant 100 may have an expanded diameter within the range of from about 1 cm to about 5 cm, and, in one embodiment, about 3 cm. The overall axial length of the implant 10 from its distal end 102 to its proximal end 104 is within the range of from about 1.5 cm to about 4 cm and, in one embodiment, about 2.5 cm.

In one embodiment, the delivery system 50 includes a transseptal, sheath 520. A radiopaque marker 521 is located near the distal end of the transseptal sheath 520.

Figure 7B:
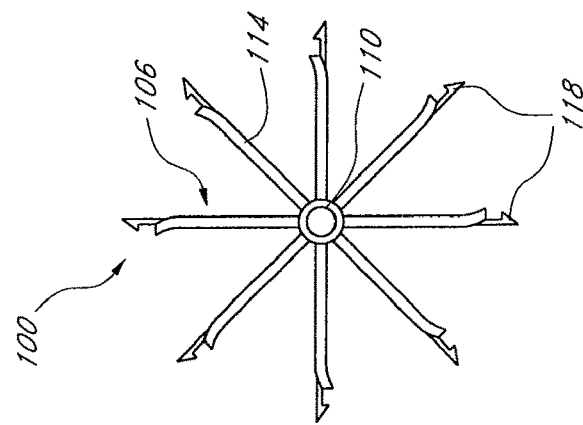
FIG. 7B is an end view taken along the line 7B-7B of FIG. 7A.
Figure 7A:
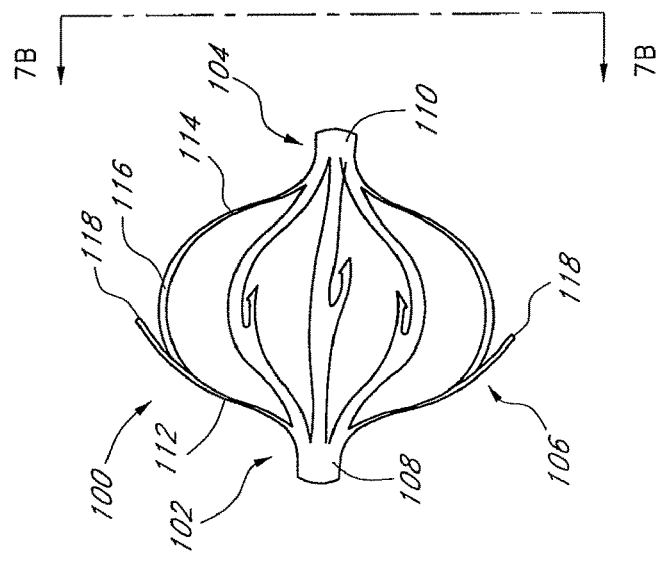
FIG. 7A is a side elevational view of the device of FIG. 7.
Figure 7:
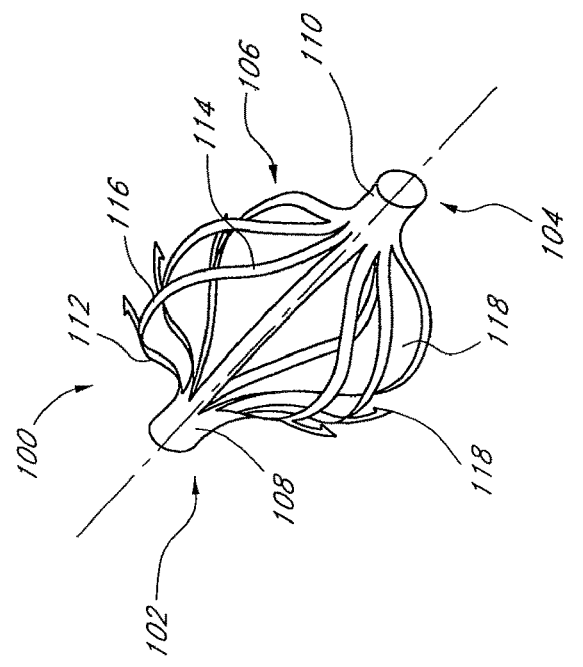
FIG. 7 is a perspective view of a support structure for a containment device in accordance with a further embodiment of the present invention.

FIGS. 7, 7A and 7B illustrate an implant 100 in accordance with another embodiment of the present invention. The implant 100 includes a distal end 102, a proximal end 104; and a longitudinal axis extending therebetween. A plurality of supports 106 extend between a distal hub 108 and a proximal hub 110. At least two or three supports 106 are provided, and in other embodiments, at least about ten supports 106 are provided. In one embodiment, sixteen supports 106 are provided. However, the precise number of supports 106 can be modified, depending upon the desired physical properties of the implant 100 as will be apparent to those of skill in the art in view of the disclosure herein, without departing from the present invention.

In an embodiment, each support 106 includes a distal spoke portion 112, a proximal spoke portion 114, and an apex 116. Each of the distal spoke portion 112, the proximal spoke portion 114, and the apex 116 may be a region on an integral support 106, such as a continuous rib or frame member which extends in a generally curved configuration as illustrated with a concavity facing towards the longitudinal axis of the implant 100. Thus, no distinct point or hinge at apex 116 is necessarily provided.

At least some of the supports 106, and, preferably, each support 106, is provided with one or two or more anchors 118 or barbs 118. In the illustrated configuration, the implant 100 is in its enlarged orientation, such as for occluding a left atrial appendage 10 or other body cavity or lumen. In, this orientation, each of the barbs 118 projects generally radially outwardly from the longitudinal axis, and is inclined in the proximal direction. One or more barbs may also be inclined distally, as is discussed elsewhere herein. In an embodiment where the barbs 118 and corresponding support 106 are cut from a single ribbon, sheet or tube stock, the barb 118 will incline radially outwardly at approximately a tangent to the curve formed by the support 106.

The illustrated anchor 118 is in the form of a barb, with at least one on each support 106 for extending into tissue at or near the opening of the LAA 10. Depending upon the embodiment, two or three barbs 118 may alternatively be desired on each support 106. In the single barb 118 embodiment of FIG. 7, each barb 118 is inclined in a proximal direction. This is to inhibit proximal migration of the implant out of the left atrial appendage 10. In this context, distal refers to the direction into the left atrial appendage 10, and proximal refers to the direction from the left atrial appendage 10 into the heart 5.

Alternatively, one or more barbs 118 may face distally, to inhibit distal migration of the implant 100 deeper into the LAA 10. Thus, the implant 100 may be provided with at least one proximally facing barb 118 and at least one distally facing barb 118. For example, in an embodiment of the type illustrated in FIG. 10, discussed below, a proximal plurality of barbs 118 may be inclined in a first direction, and a distal plurality of barbs 118 may be inclined in a second direction, to anchor the implant 100 against both proximal and distal migration.

The implant 100 constructed from the frame illustrated in FIG. 7 may be constructed in any of a variety of ways, as will become apparent to those of skill in the art in view of the disclosure herein. In one method, the implant 100 is constructed by laser cutting a piece of tube stock to provide a plurality of axially extending slots in-between adjacent supports 106. Similarly, each barb 118 can be laser cut from the corresponding support 106 or space in-between adjacent supports 106. The generally axially extending slots which separate adjacent supports 106 end a sufficient distance from each of the proximal end 104 and distal end 102 to leave a proximal hub 110 and a distal hub 108 to which each of the supports 106 will attach. In this manner, an integral cage structure may be formed. Alternatively, each of the components of the cage structure may be separately formed and attached together such as through soldering, brazing, heat bonding, adhesives, and other fastening techniques which are known in the art.

A further method of manufacturing the implant 100 is to laser cut a slot pattern on a flat sheet of appropriate material, such as a flexible metal or polymer. The supports 106 may comprise a metal such as stainless steel, nitinol, Elgiloy, or others which can be determined through routine experimentation by those of skill in the art. Wires having a circular or rectangular cross-section may be utilized depending upon the manufacturing technique. In one embodiment, rectangular cross section spokes are cut such as by known laser cutting techniques from tube stock, a portion of which forms a proximal hub 110 or a distal hub 108. The flat sheet may thereafter be rolled about an axis and opposing edges bonded together to form a tubular structure.

The apex portion 116 which carries the barb 118 may be advanced from a low profile orientation in which each of the supports 106 extend generally parallel to the longitudinal axis, to an implanted orientation as illustrated, in which the apex 116 and the barb 118 are positioned radially outwardly from the longitudinal axis. The support 106 may be biased towards the enlarged orientation, or may be advanced to the enlarged orientation under positive force following positioning within the tubular anatomical structure, in any of a variety of manners.

Referring to FIGS. 8 and 9, the implant 100 may be provided with a bather 120 such as a mesh or fabric. The barrier 120 may comprise any of a variety of materials which facilitate cellular in-growth, such as ePTFE. The suitability of alternate materials for barrier 120 can be determined through routine experimentation by those of skill in the art. The barrier 120 may be provided on either one or both axially facing sides of the implant 100. In one embodiment, the barrier 120 comprises two layers, with one layer on each side of a cage formed by a plurality of supports 106. The two layers may be bonded to each other around the supports 106 in any of a variety of ways, such as by heat bonding with or without an intermediate bonding layer such as polyethylene or FEP, adhesives, sutures, and other techniques which will be apparent to those of skill in the art in view of the disclosure herein. In an embodiment, the barrier 120 has a thickness of no more than about 0.003" and a porosity within the range of from about 5.mu.m to about 60.mu.m.

Barrier 120 may be provided on only one hemisphere, proximal face 122, or may be carried by the entire implant 100 from proximal end 104 to distal end 102. The barrier may be secured to the radially inwardly facing surface of the supports 106, as illustrated in FIG. 9, or may be provided on the radially outwardly facing surfaces of supports 106, or both.

A further embodiment of the implant 100 is illustrated in FIG. 10, in which the apex 116 is elongated in an axial direction to provide additional contact area between the implant 100 and the wall of the tubular structure. In this embodiment, one or two or three or more anchors 118 may be provided on each support 106, depending upon the desired clinical performance. The implant 100 illustrated in FIG. 10 may also be provided with any of a variety of other features discussed herein, such as a partial or complete barrier 120. In addition, the implant 100 illustrated in FIG. 10 may be enlarged using any of the techniques disclosed elsewhere herein.

Figure 11:
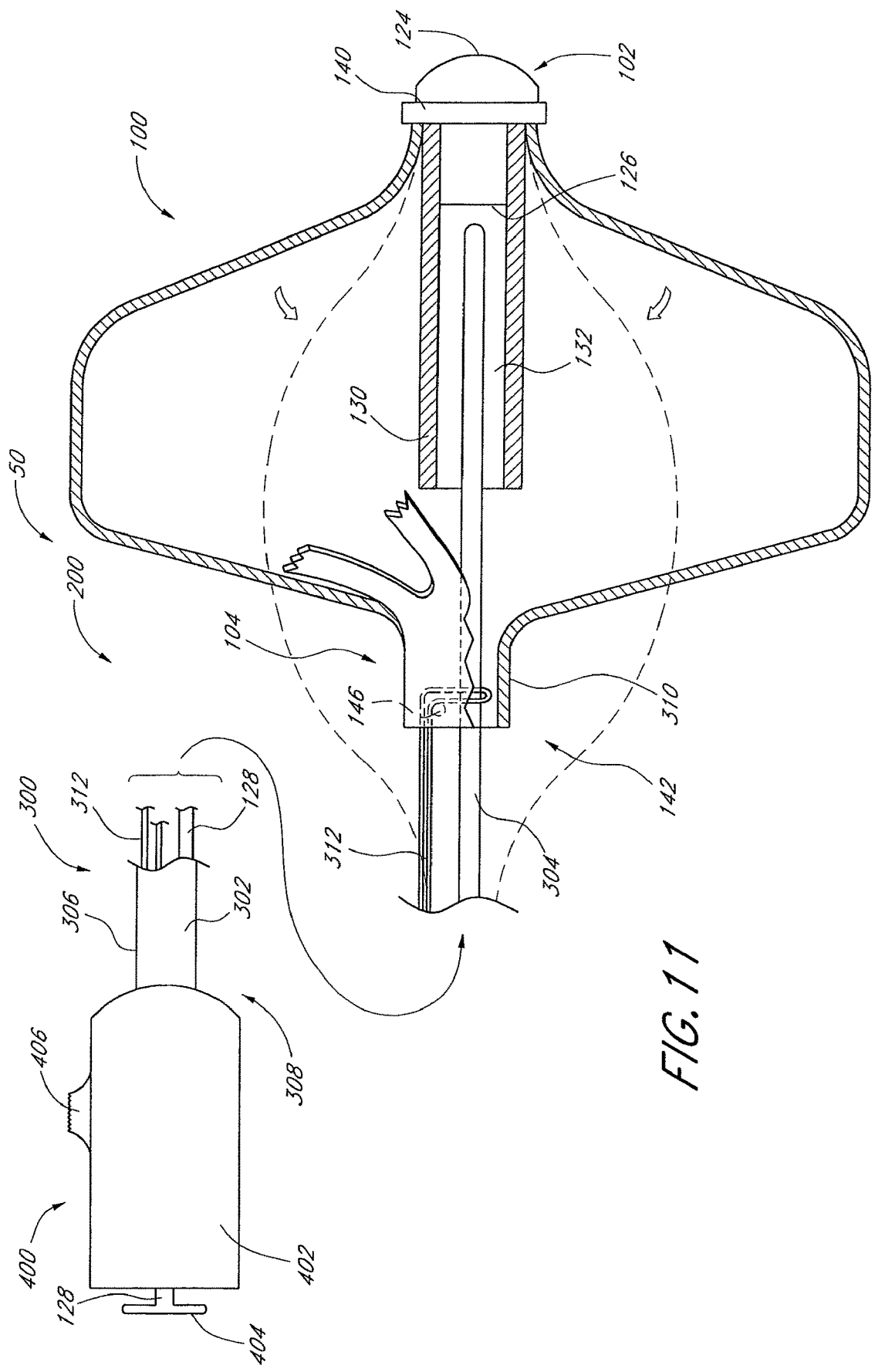
FIG. 11 is a schematic view of a deployment system in accordance with one embodiment of the present invention.

FIG. 11 illustrates another embodiment of the present invention. The implant 100 may be in the form of any of those described previously herein, as modified below. In general, the implant 100 is movable from a reduced crossing profile to an enlarged crossing profile. The implant 100 is generally introduced into the body in its reduced crossing profile, and when positioned at the desired deployment location, the implant 100 is expanded to its enlarged crossing profile. When expanded, the implant 100 obstructs or filters the flow of desired particles, emboli, blood, etc., or performs other functions while positioned therein.

The implant 100 may be biased in the direction of the enlarged crossing profile, may be neutrally biased, or may be biased in the direction of the reduced crossing profile. Any modifications to the device and deployment system to accommodate these various aspects of the implant 100 may be readily accomplished by those of skill in the art in view of the disclosure herein.

The implant 100 is a detachable component of an adjustable implant delivery system 50. The implant deliver system 50 generally includes a catheter 302 for inserting in implant into a patient's vasculature, advancing it percutaneously through the vasculature, positioning it at a desire deployment location, and deploying the implant 100 at the deployment location, such as within a body cavity or lumen, as discussed above. The catheter 302 generally includes an elongate flexible tubular body 306 that extends between a proximal end 308 and a distal end 310. The catheter body has a sufficient length and diameter to permit percutaneous entry into the vascular system and transluminal advancement through the vascular system to the desired deployment site.

For example, in an embodiment intended for access at the femoral vein and deployment within the left atrial appendage 50, the catheter 302 has a length within the range of from about 50 cm to about 150 cm, and a diameter of generally no more than about 15 French. Further dimensions and physical characteristics of catheters for navigation to particular sites within the body are well understood in the art and will not be further described herein.

The tubular body 306 is further provided with a handle 402 generally on the proximal end 308 of the catheter 302. The handle 402 permits manipulation of the various aspects of the implant delivery system 50, as will be discussed below. Handle 402 may be manufactured in any of a variety of ways, typically by injection molding or otherwise forming a handpiece for single-hand operation, using materials and construction techniques well known in the medical device arts.

In the illustrated embodiment, the distal end 102 of the implant 100 is provided with an implant plug 124. The implant plug 124 may be integral with the distal end 102 of the implant or it may be a separate, attachable piece. Implant plug 124 provides a stopping surface 126 for contacting an axially movable core 304 or other such similar structure as described herein. The core 304 extends axially throughout the length of the catheter body 302, and is attached at its proximal end to a core control 404 on the handle 402. In some embodiments, the axially movable core is referred to as a drive shaft or an implant actuation shaft. In one embodiment, the implant plug 124 comprises an atraumatic tip, such that contact between the atraumatic tip and the inside surface of the LAA 10 does not cause significant damage to the LAA 10.

The core 304 may comprise any of a variety of structures which has sufficient lateral flexibility to permit navigation of the vascular system, and sufficient axial column strength to enable reduction of the implant 100 to its reduced crossing profile. Any of a variety of structures such as hypotube, solid core wire, "bottomed out" coil spring structures, or combinations thereof may be used, depending upon the desired performance of the finished device. In one embodiment, the core 304 comprises stainless steel tubing.

The distal end of core 304 is positioned within a recess, cavity or lumen 132 defined by a proximally extending distal guide tube 130. In the illustrated embodiment, the distal guide tube 130 is a section of tubing such as metal hypotube, which is attached at the distal end 102 of the implant and extends proximally within the implant 100. In some embodiments the distal guide tube 130 includes a distal end 102 of the implant, an implant plug 124, and/or a stopping surface 126 as described herein. The distal guide tube 130 preferably extends a sufficient distance in the proximal direction to inhibit buckling or prolapse of the core 304 when distal pressure is applied to the core control 404 to reduce the profile of the implant 100. However, the guide tube 130 should not extend proximally a sufficient distance to interfere with the opening of the implant 100.

As will be appreciated by reference to FIG. 11, the guide tube 130 may operate as a limit on distal axial advancement of the proximal end 104 of implant 100. Thus, the guide tube 130 preferably does not extend sufficiently far proximally from the distal end 102 to interfere with optimal opening of the implant 100. The specific dimensions are therefore relative, and will be optimized to suit a particular intended application. In one embodiment, the implant 100 has an implanted outside diameter within the range of from about 5 mm to about 45 mm, and an axial implanted length within the range of from about 5 mm to about 45 mm. The guide tube 130 has an overall length of about 3 mm to about 35 mm, and an outside diameter of about 0.095 inches. Additional disclosure relating to this embodiment is discussed below, relating to FIGS. 11A and 11B.

Figure 12A:
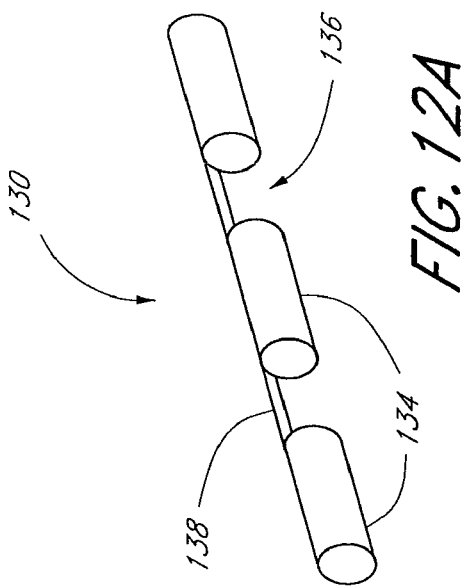
FIG. 12A is a perspective view of a flexible guide tube for use in the configurations of FIG. 11 and/or FIG. 14.
Figure 12B:
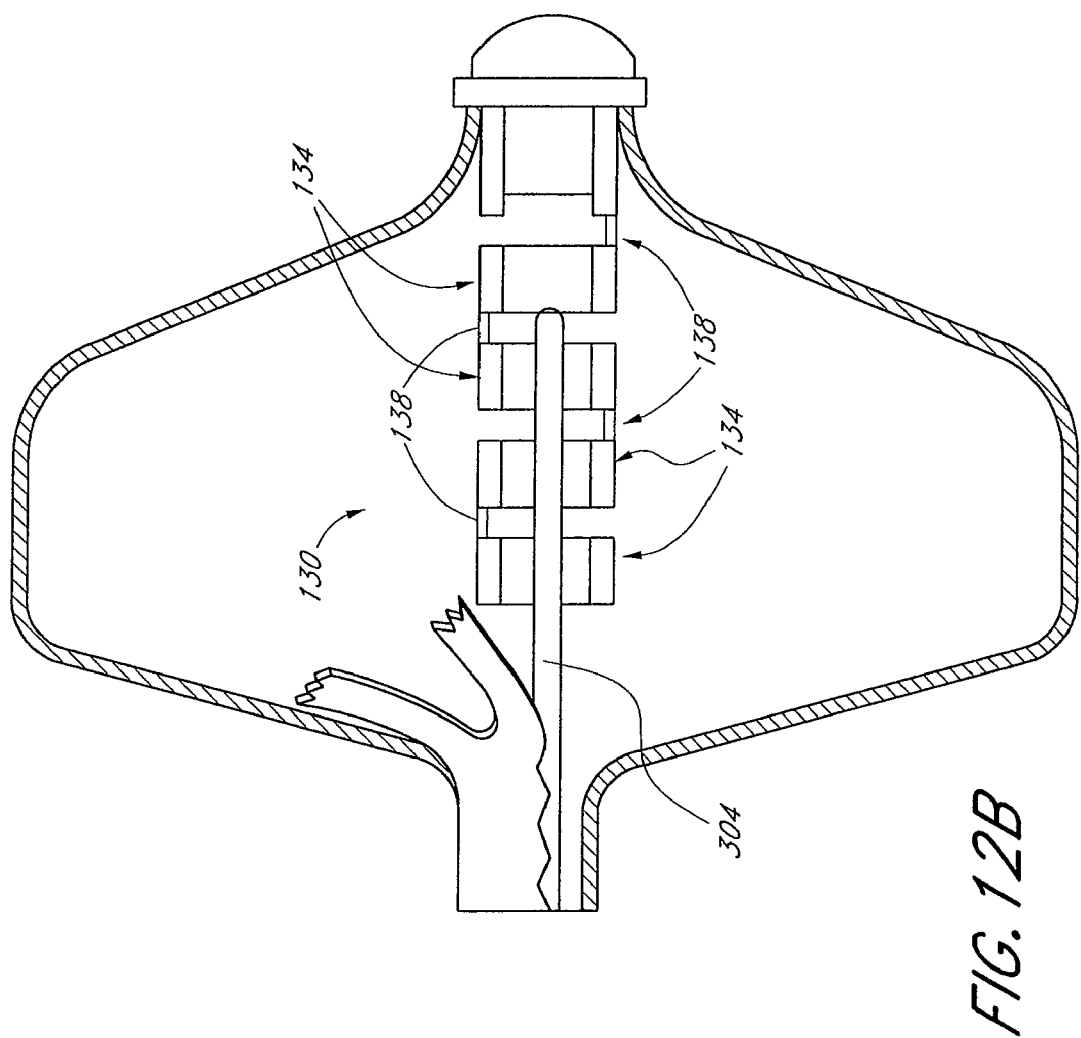
FIG. 12B is a schematic view of a flexible guide tube for use in embodiments of the configurations of FIG. 11.

An alternate embodiment of a guide tube 130 is schematically illustrated in FIGS. 12A and 12B. In this configuration, the guide tube 130 comprises a plurality of tubular segments 134 spaced apart by at least one intervening space 136. This allows increased flexibility of the guide tube 130, which may be desirable during the implantation step, while retaining the ability of the guide tube 130 to maintain linearity of the core 304 while under axial pressure. Although three segments 134 are illustrated in FIG. 12A and four segments are illustrated in FIG. 12B, as many as 10 or 20 or more segments 134 may be desirable depending upon the desired flexibility of the resulting implant. Each adjacent pair of segments 134 may be joined by a hinge element 138 which permits lateral flexibility. In the illustrated embodiment of FIG. 12A, the hinge element 138 comprises an axially extending strip or spine 138, which provides column strength along a first side of the guide tube 130. The guide tube 130 may therefore be curved by compressing a second side of the guide tube 130 which is generally offset from the spine 138 by about 180.degree. A limit on the amount of curvature may be set by adjusting the axial length of the space 136 between adjacent segments 134. As illustrated in FIG. 12B, an embodiment of a guide tube 130 may have each axial spine 138 be rotationally offset from the next adjacent axial spine 138 to enable flexibility of the overall guide tube 130 throughout a 360.degree. angular range of motion.

Alternatively, the flexible hinge point 138 between each adjacent segment 134 may be provided by cutting a spiral groove or plurality of parallel grooves in a tubular element in between what will then become each adjacent pair of segments 134. In this manner, each tubular element 134 will be separated by an integral spring like structure, which can permit flexibility. As a further alternative, the entire length of the guide tube 130 may comprise a spring. Each of the forgoing embodiments may be readily constructed by laser cutting or other cutting from a piece of tube stock, to produce a one piece guide tube 130. Alternatively, the guide tube 130 may be assembled from separate components and fabricated together using any of a variety of bonding techniques which are appropriate for the construction material selected for the tube 320.

Various distal end 102 constructions may be utilized, as will be apparent to those of skill in the art in view of the disclosure herein. In the illustrated embodiment, the distal implant plug 124 extends within the implant 100 and is attached to the distal end of the guide tube 130. The implant plug 124 may be secured to the guide tube 130 and implant 100 in any of a variety of ways, depending upon the various construction materials. For example, any of a variety of metal bonding techniques such as a welding, brazing, interference fit such as threaded fit or snap fit, may be utilized. Alternatively, any of a variety of bonding techniques for dissimilar materials may be utilized, such as adhesives, and various molding techniques. In one construction, the implant plug 124 comprises a molded polyethylene cap, and is held in place utilizing a distal cross pin 140 which extends through the implant 100, the guide tube 130 and the implant plug 124 to provide a secure fit against axial displacement.

Some left atrial appendage implants, such as some of those described in some of the embodiments above (for examples, see FIGS. 11-12B) and below (e.g., see FIG. 14-16B), include a single guide tube 130 at the distal end 102 of the implant 100 that connects to or engages an implant actuation shaft and provides axial load transmission from the distal guide tube 130 to the implant 100 at its distal end 102. In some embodiments, the shaft may be an implant actuation shaft 334, an axially moveable core 304 or rotatable core 342.

When the implant actuation shaft is particularly flexible or relatively long for actuation of a long implant 100, it could buckle if not adequately supported within the implant 100. To prevent bending or buckling of the implant actuation shaft 334, support preferably is provided only inside the implant 100 in order to maintain the interface with a catheter system 300 proximal and adjacent to the implant 100 as flexible as possible. Given the continuously changing length of the implant 100 depending on its expansion state, a support member that also changed length with the implant 100 would be useful as well.

Figure 13A:
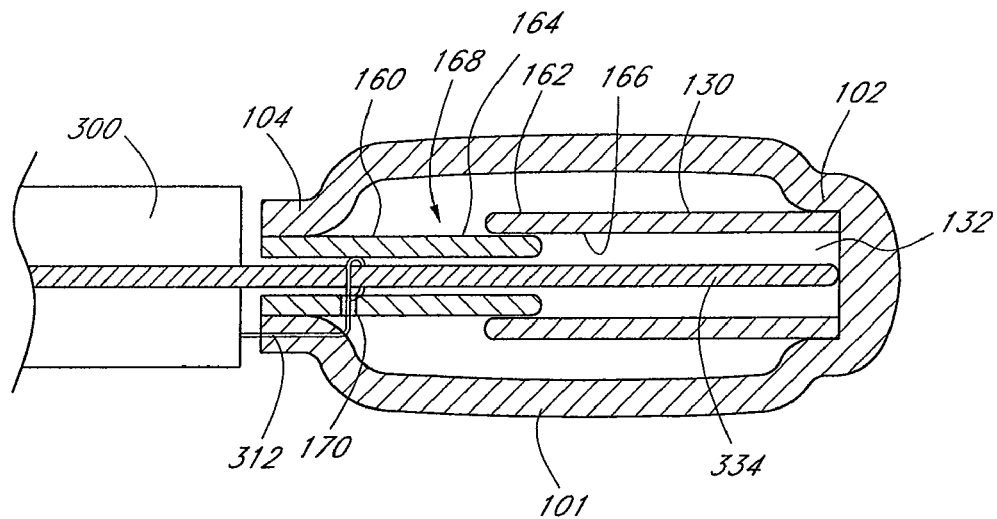
FIG. 13A is a schematic view of an implant with concentric slideable guide tubes in a radially-reduced state in accordance with one embodiment of the present invention.
Figure 13B:
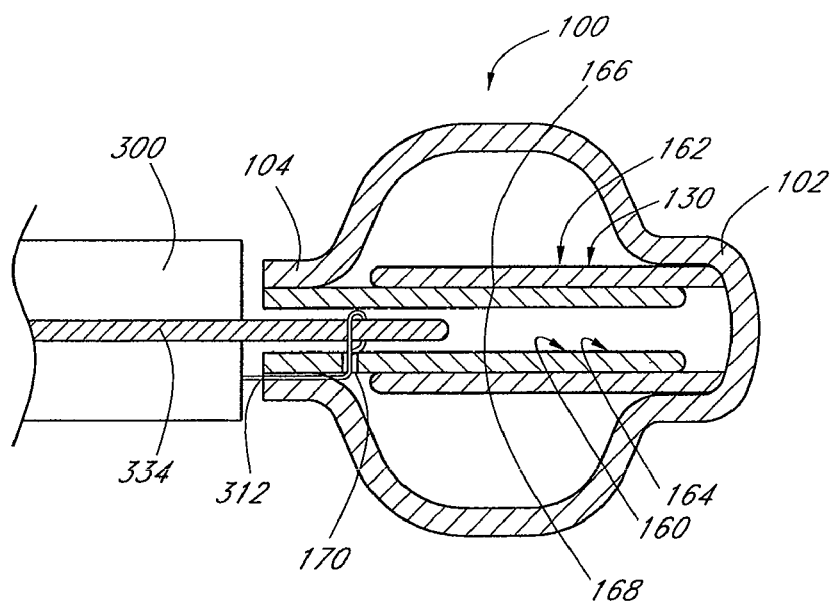
FIG. 13B is a schematic view of the implant with concentric slideable guide tubes of FIG. 13A in a radially-expanded state.

FIGS. 13A and 13B illustrate an alternate embodiment of an implant 100, which includes multiple guide tubes 162, 164. The implant 100 includes two substantially concentric or axially aligned telescoping guide tubes 162, 164, which are slidably moveable with respect to one another. The outer guide tube 162 is attached to the implant's distal end 102 or may be integrally formed therewith, and the inner guide tube 164 is attached to its proximal end 104 or may be integrally formed therewith, although in other embodiments they are attached to proximal and distal ends, respectively. In a concentric embodiment, the outer guide tube 162 has an internal diameter sufficiently large enough to contain the outer diameter of the inner guide tube 164. In certain embodiments, the telescoping guide tubes 162 and 164 perform a support function when each is anchored at either the distal end 102 or proximal end 104 of the implant 100 and by freely floating at the interface between telescoping guide tubes 162 and 164.

The outer guide tube 162 and the inner guide tube 164 are sized to allow full support of an implant actuation shaft 334 without increasing the collapse force used to reduce the implant's diameter. The telescoping guide tubes 162 and 164 can be utilized with embodiments having a disconnect mount 236 (see FIGS. 17-21), tethered embodiments, or any other embodiments disclosed herein.

Referring to FIG. 13A, when the implant 100 is in a radially reduced state, the inner guide tube 164 overlaps the outer guide tube 162, as shown. Alternatively, the inner guide tube 164 may not overlap with the outer guide tube 162 in the radially reduced state of the implant 100. Referring to FIG. 13B, when the implant 100 is radially expanded, the inner guide tube 164 slides into the outer guide tube 162 as the overall length of the implant 100 is axially shortened. The outer guide tube 162 can have a flared end to facilitate collapse of the implant 100. A flared end of the outer guide tube 162 can help guide the inner guide tube 164 during expansion. Similarly, the inner guide tube 164 can have a tapered end.

In some embodiments of an implant 100 with multiple guide tubes, either of the outer guide tube 162 or the inner guide tube 164 may also be a distal guide tube 130 or a proximal guide tube 160. The outer guide tube 162 can be a distal guide tube 130 attached at its distal end to the distal end 102 of the implant 100, and the inner guide tube 164 can be a proximal guide tube 160 attached at its proximal end to the proximal end 104 of the implant 100. The outer guide tube 162 may include a mating surface on or near its distal end to engage a mating surface on the distal hub 108, or elsewhere on the implant 100.

Relative proximal and distal movement of the inner guide tube 164 and outer guide tube 162 is preferably limited by a motion limit. In one embodiment, the motion limit includes at least one cross pin. In other embodiments, the motion limit includes at least one flare, annular ring, bump, or other suitable mechanism as is well known to those of skill in the art. The outer guide tube 162 slidably engages the inner guide tube 164, which preferably enters the proximal end of the outer guide tube 162. One advantage of this embodiment is a reduction in the likelihood that the insertion of an implant actuation shaft 334 into the implant 100 will bind on the proximal end of distal guide tube 130 while assembling a implant delivery system 50 or while attempting to recapture a detached implant 100. Alternatively, in another embodiment, the outer guide tube 162 can be attached at its proximal end to the proximal end 104 of the implant 100, and the inner guide tube 164 can be attached at its distal end to the distal end 102 of the implant 100.

In an embodiment of an implant 100 with multiple guide tubes, the distal guide tube 130 has a distal guide tube lumen 132 and the proximal guide tube 160 has a proximal guide tube lumen 170. These lumens 132 and 170 may contain radiopaque or contrast materials injected into the catheter system 300 through ports in the deployment handle 400. The proximal guide tube 160 may have a window 170 that passes through the wall of the proximal guide tube 160. The window 170 may be used to release contrast materials in the proximal guide tube lumen 170 toward the proximal end 104 of the implant 100. This window 170 may also be used as an anchor point or port through which a pull wire 312 from a catheter system 300 may be used to secure the implant 100 prior to detachment.

In certain embodiments of an implant 100 with multiple guide tubes, a slideable engagement surface 166 of the outer guide tube 162 may interface with a slideable engagement surface 168 of the inner guide tube 164. Various embodiments of the outer guide tube 162 and inner guide tube 164 may comprise generally circular cross sections which allow free rotation about the concentric axis of the guide tubes along the generally coaxial cylindrical slideable engagement surfaces 166 and 168. Alternatively, other embodiments may have slideable engagement surfaces 166 and 168 which are elliptically-shaped or contain certain key and slot configurations or similar interface configurations known in the art to prevent or reduce relative rotation between the outer guide tube 162 and inner guide tube 164. Depending on how the guide tubes are attached to the ends of the implant 100, these rotation-inhibiting embodiments may provide additional support to reduce rotation in the frame 101 of the implant 100.

Figure 14:
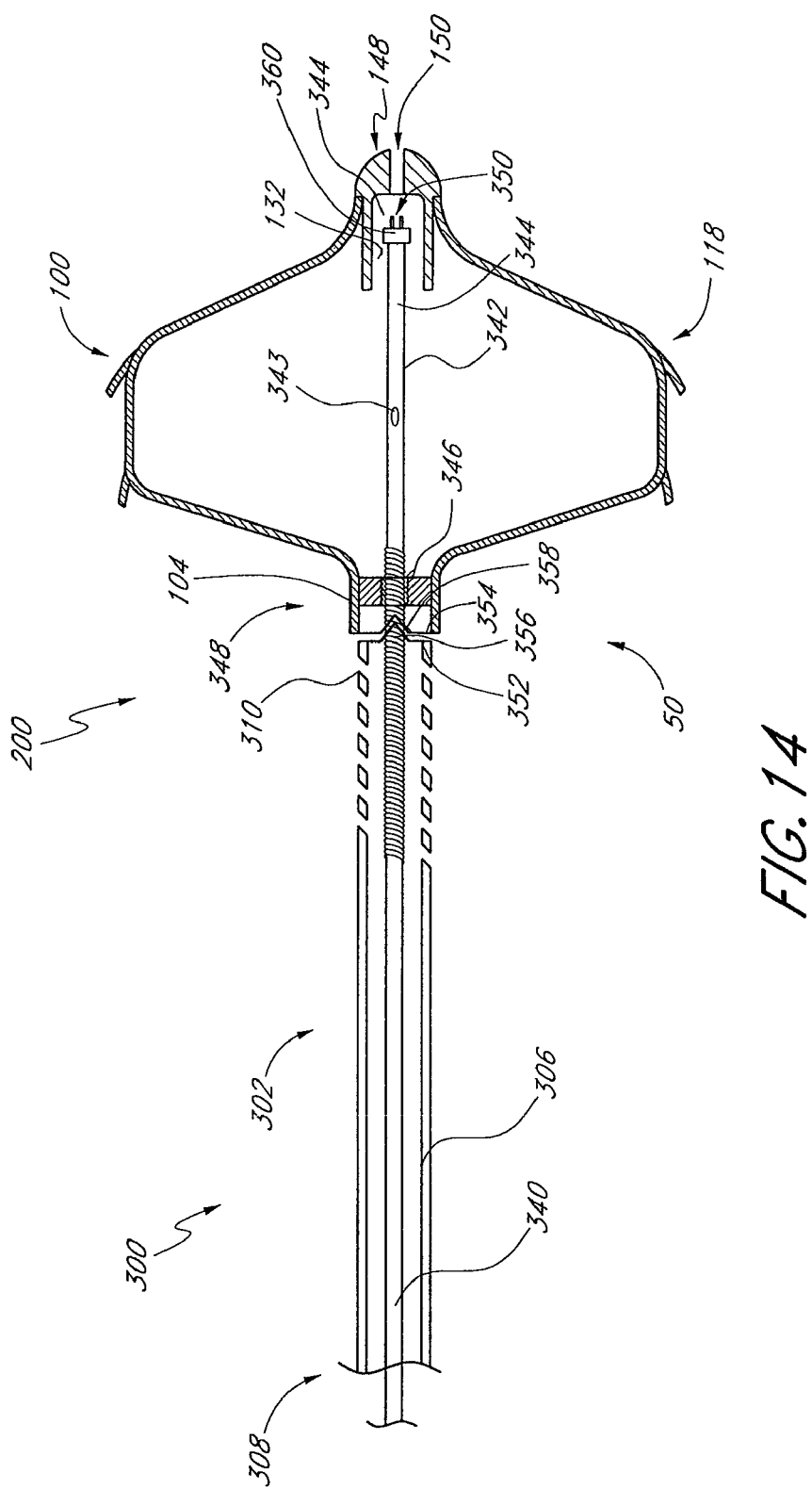
FIG. 14 is a schematic view of an alternate deployment system in accordance with one embodiment of the present invention.

In some embodiments of the implant actuation shaft 334, the shaft may be an axially moveable core 304, a rotatable core 342, or a shaft that uses an unscrew-to-release mechanism similar to an embodiment as illustrated in FIG. 14 (see below). By using two telescoping guide tubes 130 and 160, the free detensioned length of the implant 100 can be doubled.

Further advantages of multiple guide tube embodiments are described in the context of an improved implant release and recapture mechanism.

2. Implant Release and Recapture Mechanisms

Various embodiments of implant release and recapture mechanisms provide an interface between an implant and a catheter system used to deploy, detach, and recapture the implant.

a. Pull Wire Mechanisms

Referring back to FIG. 11, there is illustrated an embodiment of an implant delivery system 50 with a detachable implant 100, an implant release and recapture mechanism 200, a catheter system 300, and a deployment handle 400. As illustrated in this embodiment, the implant release and recapture mechanism 200 includes a release element, such as a pull wire 312, which keeps the proximal end 104 of the implant 100 in tension. An axially moveable core 304 simultaneously pushes against the distal end 102 of the implant 100. The combination of pulling on the implant proximal end 104 while pushing on its distal end 102 keeps the implant 100 in a compressed state. When either the core 304 is pulled proximally or the pull wire 312 is allowed to move distally, the tension on the ends of the implant 100 is reduced, thereby allowing the spring loaded or shape memory material in the implant 100 to radially expand into its normal expanded state.

In this embodiment, the proximal end 104 of the implant 100 is provided with a releasable lock 142 for attachment to a pull wire 312. Pull wire 312 extends proximally throughout the length of the tubular body 306 to a proximal pull wire control 406 on the handle 402.

As used herein, the term pull wire is intended to include any of a wide variety of structures which are capable of transmitting axial tension or compression such as a pushing or pulling force with or without rotation from the proximal end 308 to the distal end 310 of the catheter 302. Thus, monofilament or multifilament metal or polymeric rods or wires, woven or braided structures may be utilized. Alternatively, tubular elements such as a concentric tube positioned within the outer tubular body 306 may also be used as will be apparent to those of skill in the art.

In the illustrated embodiment in FIG. 11, the pull wire 312 is releasably connected to the proximal end 104 of the implant 100. This permits proximal advancement of the proximal end of the implant 100, which cooperates with a distal retention force provided by the core 304 against the distal end of the implant to axially elongate the implant 100 thereby reducing it from its implanted configuration to its reduced profile for implantation. The proximal end of the pull wire 312 may be connected to any of a variety of pull wire controls 406, including rotational knobs, levers and slider switches, depending upon the design preference.

The implant delivery system 50 thus permits the implant 100 to be maintained in a low crossing profile configuration, to enable transluminal navigation to a deployment site. Following positioning at or about the desired deployment site, proximal retraction of the core 304 enables the implant 100 to radially enlarge under its own bias to fit the surrounding tissue structure. Alternatively, the implant can be enlarged under positive force, such as by inflation of a balloon or by a mechanical mechanism. Once the clinician is satisfied with the position of the implant 100, such as by injection of dye and visualization using conventional techniques, the core 304 is proximally retracted thereby releasing the lock 142 and enabling detachment of the implant 100 from the deployment system 300.

If, however, visualization reveals that the implant 100 is not at the location desired by the clinician, proximal retraction of the pull wire 312 with respect to the core 304 will radially reduce the diameter of the implant 100, thereby enabling repositioning of the implant 100 at the desired site. Thus, the present invention permits the implant 100 to be enlarged or reduced by the clinician to permit repositioning and/or removal of the implant 100 as may be desired.

The proximal end 104 of the implant 100 is preferably provided with a releasable lock 142 for attachment of the pull wire 312 to the deployment catheter 302. In the illustrated embodiment in FIG. 11, the releasable lock 142 is formed by advancing the pull wire 312 distally around a proximal cross pin 146, and providing an eye or loop which extends around the core 304. As long as the core 304 is in position within the implant 100, proximal retraction of the pull wire 312 will advance the proximal end 104 of the implant 100 in a proximal direction. See FIG. 11A. However, following deployment, proximal retraction of the core 304 such as by manipulation of the core control 404 will pull the distal end of the core 304 through the loop on the distal end of the pull wire 312. The pull wire 312 may then be freely proximally removed from the implant 100, thereby enabling detachment of the implant 100 from the delivery system 50 within a treatment site. See FIG. 11B.

Figure 11A:
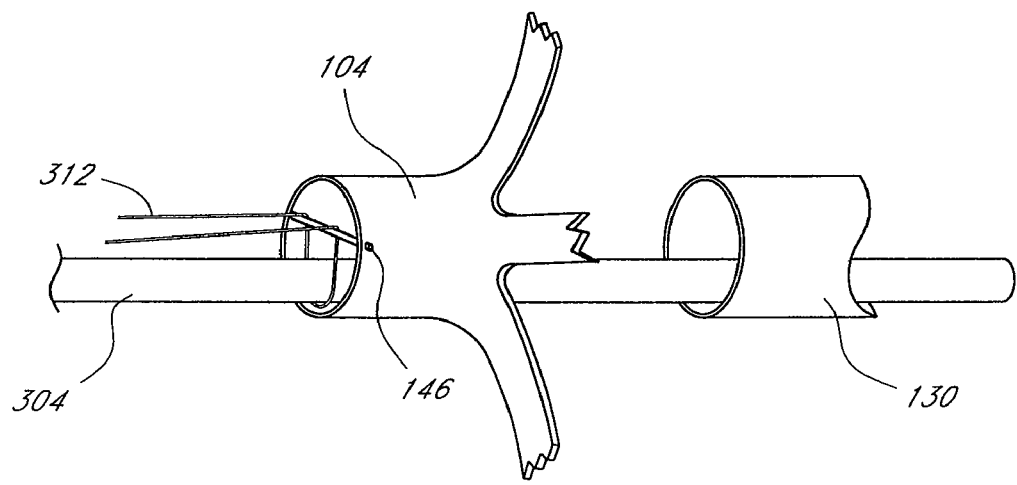
FIG. 11A is an enlarged detail view of the deployment system of FIG. 11, showing a releasable lock in an engaged configuration.
Figure 11B:
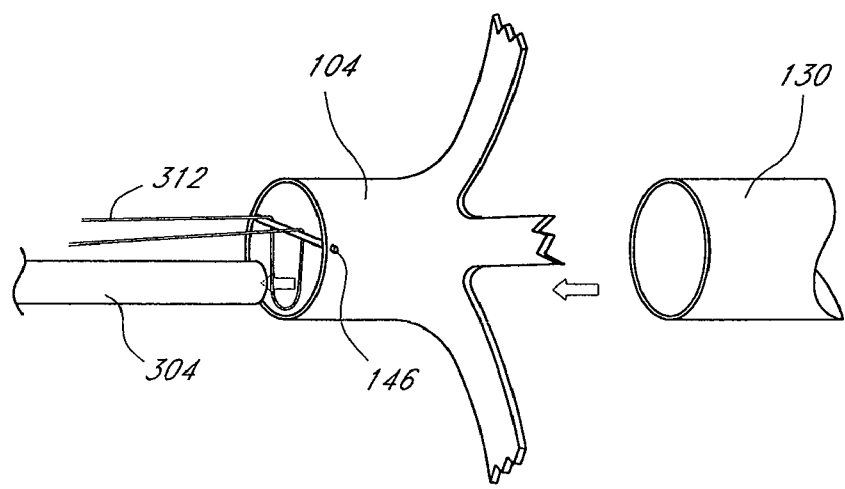
FIG. 11B is an enlarged detail view as in FIG. 11A, with a core axially retracted to release the implant.

The embodiment illustrated in FIGS. 11, 11A and 11B may impart bias to the implant 100 because the location of the cross pin 146 creates a moment arm with respect to the core 304 when tension is applied to the pull wire 312 in order to maintain the implant 100 in a radially-reduced configuration. Tension through the pull wire 312 may be on the order of six pounds of force, which when loaded off-center by the pull wire 312 over the distance between the center of the core 304 over the cross pin 146 may result in significant torque and bias on the implant 100 while it is being deployed in the LAA 10. This bias may result in deflection in the delivery system 50 which may cause the implant 100 to jump, move, rotate, etc., when released from the catheter system 300 during detachment.

b. Threadable Torque Rod Mechanisms

FIG. 14 illustrates an alternate embodiment of an implant deployment system 50 in which an implant 100 is radially enlarged or reduced by rotating a torque element extending throughout the deployment catheter. This embodiment of the implant deployment system 50 reduces the bias of moment arms described in the previous embodiment by eliminating off-center pull wires 312 (as illustrated in FIGS. 11, 11A and B). Instead, the elongate flexible tubular body 306 of the deployment catheter 302 includes a rotatable torque rod 340 extending axially therethrough. The proximal end of the torque rod 340 may be connected at a proximal manifold to a manual rotation device such as a hand crank, thumb wheel, rotatable knob or the like. Alternatively, the torque rod 340 may be connected to a power driven source of rotational energy such as a motor drive or air turbine. The distal end of the torque rod 340 is integral with or is connected to a rotatable core 342 which extends axially through the implant 100. A distal end 344 of the rotatable core 342 is positioned within a cavity 132 as has been discussed.

The terms torque rod or torque element are intended to include any of a wide variety of structures which are capable of transmitting a rotational torque throughout the length of a catheter body. For example, solid core elements such as stainless steel, nitinol or other nickel titanium alloys, or polymeric materials may be utilized. In an embodiment intended for implantation over a guidewire, the torque rod 340 is preferably provided with an axially extending central guidewire lumen. This may be accomplished by constructing the torque rod 340 from a section of hypodermic needle tubing, having an inside diameter of from about 0.001 inches to about 0.005 inches or more greater than the outside diameter of the intended guidewire. Tubular torque rods 340 may also be fabricated or constructed utilizing any of a wide variety of polymeric constructions which include woven or braided reinforcing layers in the wall. Torque transmitting tubes and their methods of construction are well understood in the intracranial access and rotational atherectomy catheter arts, among others, and are not described in greater detail herein.

Use of a tubular torque rod 340 also provides a convenient infusion lumen for injection of contrast media within the implant 100, such as through a port 343 or lumen 350. In one embodiment, axially moveable core 304 also includes a lumen 350. The lumen 350 preferably allows visualization dye to flow through the lumen 350 of the axially moveable core 304, through the lumen 150 of the implant end cap 148, and into the left atrial appendage 10. Such usage of visualization dye is useful for clinical diagnosis and testing of the position of the implant 100 within the left atrial appendage 10 or other body opening, as described in greater detail below.

The marker 360 as shown in FIG. 14 advantageously assists in locating the position of the distal end 344 of the axially moveable core 342. In one embodiment, marker 360 comprises a radiopaque band press fit onto the distal end 344 of the axially moveable core 342. Marker 360 preferably is made from a material readily identified after insertion into a patient's body by using visualization techniques that are well known to those of skill in the art. In one embodiment, the marker 360 is made from gold, or tungsten, or any such suitable material, as is well known to those of skill in the art. In another embodiment, marker 360 is welded, soldered, or glued onto the distal end 344 of the axially moveable core 342. In one embodiment, marker 360 is an annular band and surrounds the circumference of the axially moveable core 342. In other embodiments, the marker 360 does not surround the circumference of the axially moveable core 342. In other embodiments, marker 360 includes evenly or unevenly spaced marker segments. In one embodiment, the use of marker segments is useful to discern the radial orientation of the implant 100 within the body.

The proximal end 104 of the implant 100 is provided with a threaded aperture 346 through which the core 342 is threadably engaged. As will be appreciated by those of skill in the art in view of the disclosure herein, rotation of the threaded core 342 in a first direction relative to the proximal end 104 of the implant 100 will cause the rotatable core 342 to advance distally. This distal advancement will result in an axial elongation and radial reduction of the implantable device 100. Rotation of the rotatable core 342 in a reverse direction will cause a proximal retraction of the rotatable core 342, thus enabling a radial enlargement and axial shortening of the implantable device 100.

The deployment catheter 302 is further provided with an anti-rotation lock 348 between a distal end 310 of the tubular body 306 and the proximal end 104 of the implant 100. In general, the rotational lock 348 may be conveniently provided by cooperation between a first surface 352 on the distal end 310 of the deployment catheter 302, which engages a second surface 354 on the proximal end 104 of the implant 100, to rotationally link the deployment catheter 302 and the implantable device 100. Any of a variety of complementary surface structures may be provided, such as an axial extension on one of the first 352 and second surfaces 354 for coupling with a corresponding recess on the other of the first 352 and second surfaces 354. Such extensions and recesses may be positioned laterally offset from the axis of the catheter 302. Alternatively, they may be provided on the longitudinal axis with any of a variety of axially releasable anti-rotational couplings having at least one flat such as a hexagonal or other multifaceted cross-sectional configuration.

Upon placement of the implant 100 at the desired implantation site, the torque rod 340 is rotated in a direction that produces an axial proximal retraction. This allows radial enlargement of the radially outwardly biased implant 100 at the implantation site. Continued rotation of the torque rod 340 will cause the threaded core 342 to exit proximally through the threaded aperture 346. At that point, the deployment catheter 302 may be proximally retracted from the patient, leaving the implanted device 100 in place.

By modification of the decoupling mechanism to allow the core 342 to be decoupled from the torque rod 340, the rotatable core 342 may be left within the implant 100, as may be desired depending upon the intended deployment mechanism. For example, the distal end of the core 342 may be rotatably locked within the end cap 148, such as by including complimentary radially outwardly or inwardly extending flanges and grooves on the distal end of the core 342 and inside surface of the cavity 132. In this manner, proximal retraction of the core 342 by rotation thereof relative to the implant 100 will pull the end cap 148 in a proximal direction under positive force. This may be desirable as a supplement to or instead of a radially enlarging bias built into the implant 100.

In other embodiments, the torque rod 340 is threaded at its distal end. The distal end is threaded into a sliding nut located within a guide tube extending from the distal end of the implant 100. Such embodiments are described in greater detail in U.S. application Ser. No. 10/642,384, filed Aug. 15, 2003, published as U.S. Publication No. 2005/0038470, which is expressly incorporated by reference herein. Another embodiment of an implant deployment system that could include a torque rod threaded at its distal end in a manner similar to an embodiment illustrated in FIG. 16A.

Figure 15A:
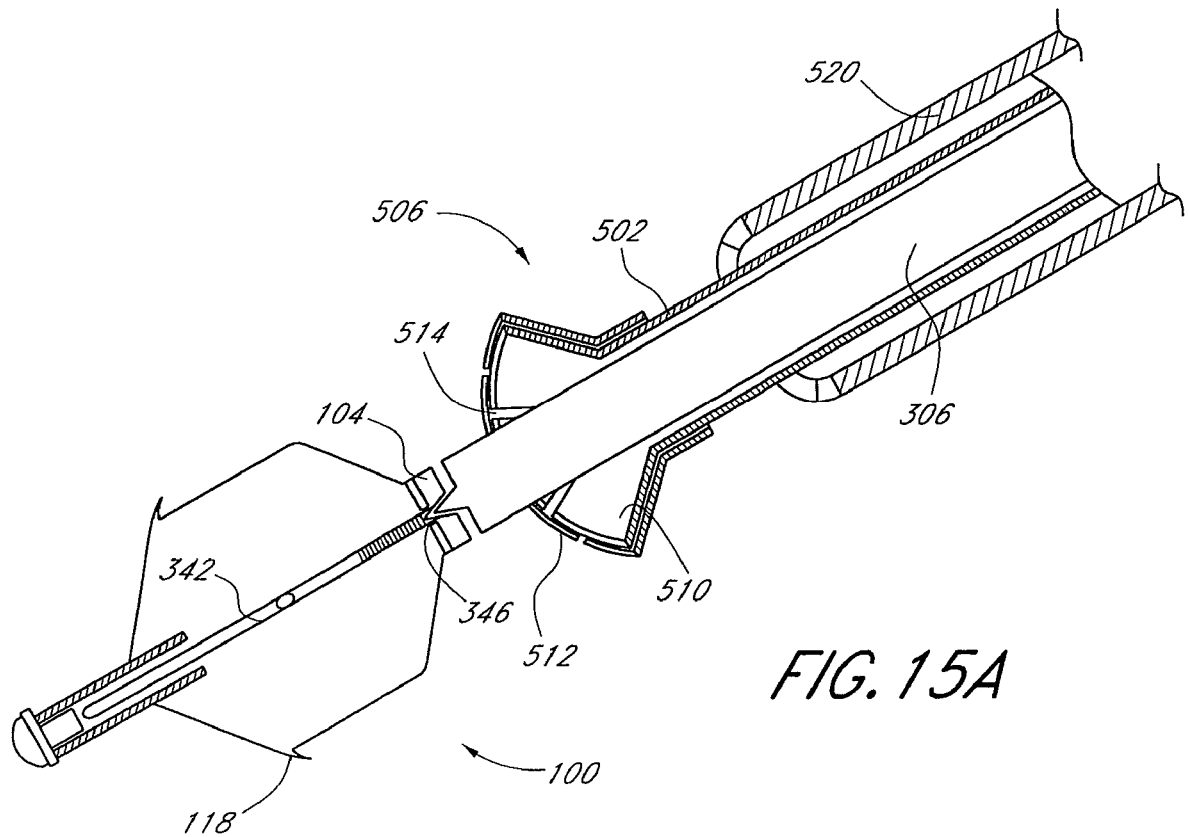
FIG. 15A illustrates a schematic cross-sectional view through the distal end of a retrieval catheter having a containment device removably connected thereto in accordance with one embodiment of the present invention.

The implant 100 may also be retrieved and removed from the body in accordance with a further aspect of the present invention. One manner of retrieval and removal is described with respect to FIGS. 15A-E. Referring to FIG. 15A, an implanted device 100 is illustrated as releasably coupled to the distal end of the tubular body 306, as has been previously discussed. Coupling may be accomplished by aligning the tubular body 306 with the proximal end 104 of the deployed implant 100, under fluoroscopic visualization, and distally advancing a rotatable core 342 through the threaded aperture 346. Threadable engagement between the rotatable core 342 and aperture 346 may thereafter be achieved, and distal advancement of core 342 will axially elongate and radially reduce the implant 100.

The tubular body 306 is axially movably positioned within an outer tubular delivery or retrieval catheter 502. In various embodiments, the retrieval catheter 502 may be separate and distinct from the delivery or deployment catheter 302, or the retrieval catheter 502 may be coaxial with the delivery or deployment catheter 302, or the retrieval catheter 502 may be the same catheter as the delivery or deployment catheter 302. Catheter 502 extends from a proximal end (not illustrated) to a distal end 506. The distal end 506 is preferably provided with a flared opening, such as by constructing a plurality of petals 510 for facilitating proximal retraction of the implant 100 as will become apparent.

Petals 510 may be constructed in a variety of ways, such as by providing axially extending slits in the distal end 506 of the catheter 502. In this manner, preferably at least about three, and generally at least about four or five or six petals or more will be provided on the distal end 506 of the catheter 502. Petals 510 manufactured in this manner would reside in a first plane, transverse to the longitudinal axis of the catheter 502, if each of such petals 510 were inclined at 90 degrees to the longitudinal axis of the catheter 502.

Figure 15B:
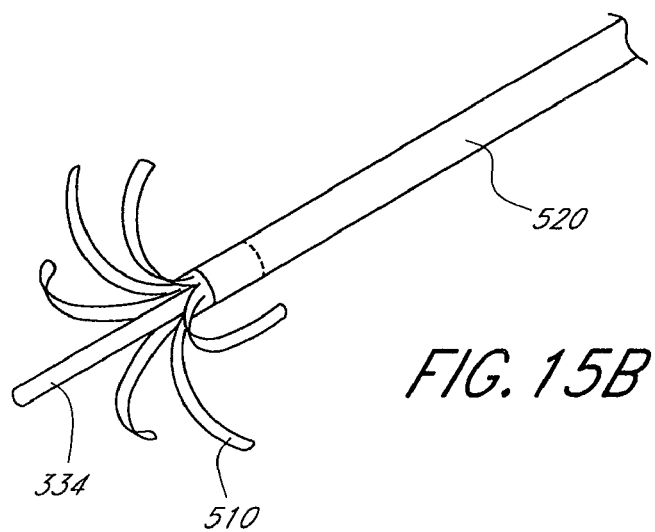
FIG. 15B is a perspective view of an embodiment of a single layer petal configuration of a portion of a retrieval catheter in accordance with one embodiment of the present invention.

In one embodiment, a second layer of petals 512 are provided, which would lie in a second, adjacent plane if the petals 512 were inclined at 90 degrees to the longitudinal axis of the catheter 502. Preferably, the second plane of petals 512 is rotationally offset from the first plane of petals 510, such that the second petals 512 cover the spaces 514 formed between each adjacent pair of petals 510. The use of two or more layers of staggered petals 510 and 512 has been found to be useful in retrieving implants 100, particularly when the implant 100 carries a plurality of tissue anchors 118. However, in many embodiments, the retrieval catheter 502 includes only a single plane of petals 510, such as illustrated in FIG. 15B.

The petals 510 and 512 may be manufactured from any of a variety of polymer materials useful in constructing medical device components such as the catheter 502. This includes, for example, polyethylene, PET, PEEK, PEBAX, and others well known in the art. The second petals 512 may be constructed in any of a variety of ways. In one convenient construction, a section of tubing which concentrically fits over the catheter 502 is provided with a plurality of axially extending slots in the same manner as discussed above. The tubing with a slotted distal end may be concentrically positioned on the catheter 502, and rotated such that the space between adjacent petals 512 is offset from the space between adjacent petals 510. The hub of the petals 512 may thereafter be bonded to the catheter 502, such as by heat shrinking, adhesives, or other bonding techniques known in the art. FIG. 15B shows a perspective view of an embodiment of a single layer of petals 510 which is coaxial with a transseptal catheter 520 and an implant actuation shaft 334. The implant actuation shaft 334 can be rotatable core 342 as illustrated in FIG. 15A.

Figure 15C:
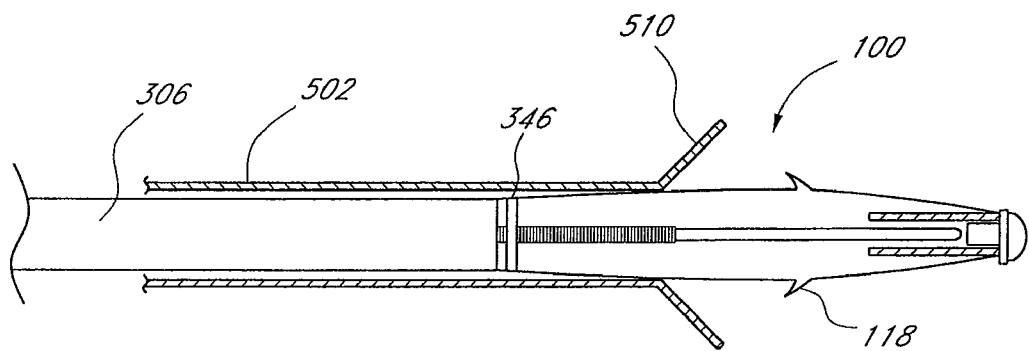
FIG. 15C is a schematic cross-sectional view of the system illustrated in FIG. 15A, with the containment device axially elongated and radially reduced.
Figure 15D:
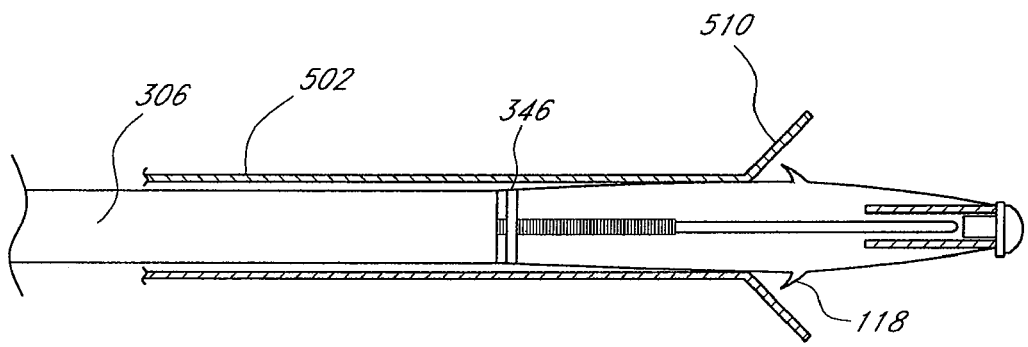
FIG. 15D is a cross-sectional schematic view as in FIG. 15C, with the containment device drawn part way into the retrieval catheter.
Figure 15E:
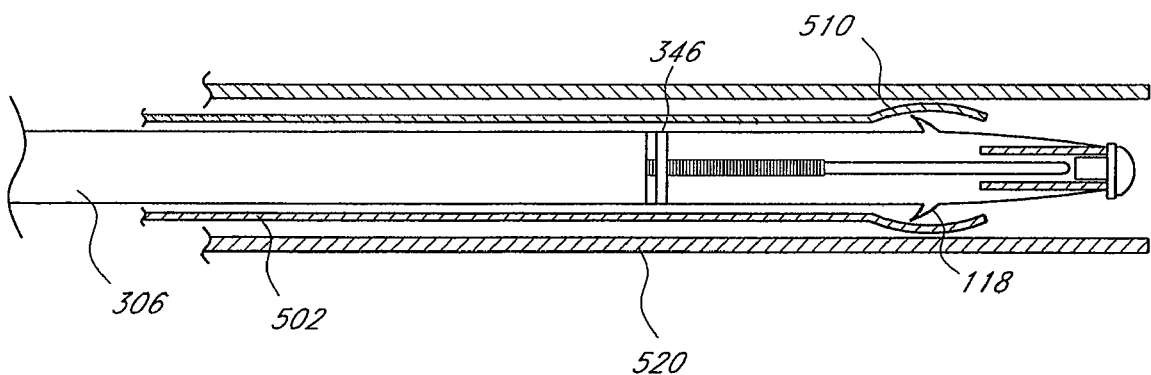
FIG. 15E is a schematic view as in FIG. 15D, with the containment device and delivery catheter drawn into a transseptal sheath.

The removal sequence will be further understood by reference to FIGS. 15C through 15E. Referring to FIG. 15C, the radially reduced implant 100 is proximally retracted part way into the retrieval catheter 502. This can be accomplished by proximally retracting the tubular body 306 and/or distally advancing the catheter 502. As illustrated in FIG. 15D, the tubular body 306 having the implant 100 attached thereto is proximally retracted a sufficient distance to position the tissue anchors 118 within the petals 510. The entire assembly of the tubular body 306, within the retrieval catheter 502 may then be proximally retracted within the transseptal sheath 520 or other tubular body as illustrated in FIG. 15E. The collapsed petals 510 allow this to occur while preventing engagement of the tissue anchors 118 with the distal end of the transseptal sheath 520 or body tissue. The entire assembly having the implant 100 contained therein may thereafter be proximally withdrawn from or repositioned within the patient.

The embodiments illustrated in FIGS. 14 and 15 may impart bias to the implant 100 because relative rotation between the catheter system 300 and the implant 100 is required in order to release the threaded locking system described above. When the implant 100 is to be radially expanded within the LAA 10 the torque rod 342 must be rotated with respect to the threaded aperture 346 in the implant 100. The rotation of the rod with respect to the implant may result in torque, causing a rotational bias in the implant 100 with respect to the LAA 10 as well as with respect to the catheter system 300. This bias may result in deflection in the delivery system 50 which may cause the implant 100 to "jump" or "spin" when released from the catheter system 300 during detachment.

c. Axial Decoupling Mechanisms

Figure 16B:
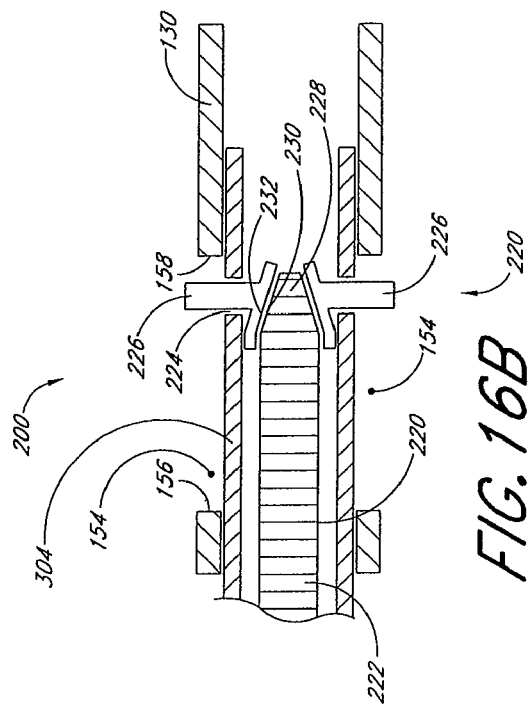
FIG. 16B is a schematic partial sectional view of an assembly incorporating quick-disconnect functionality of the assembly in FIG. 16A.
Figure 16A:
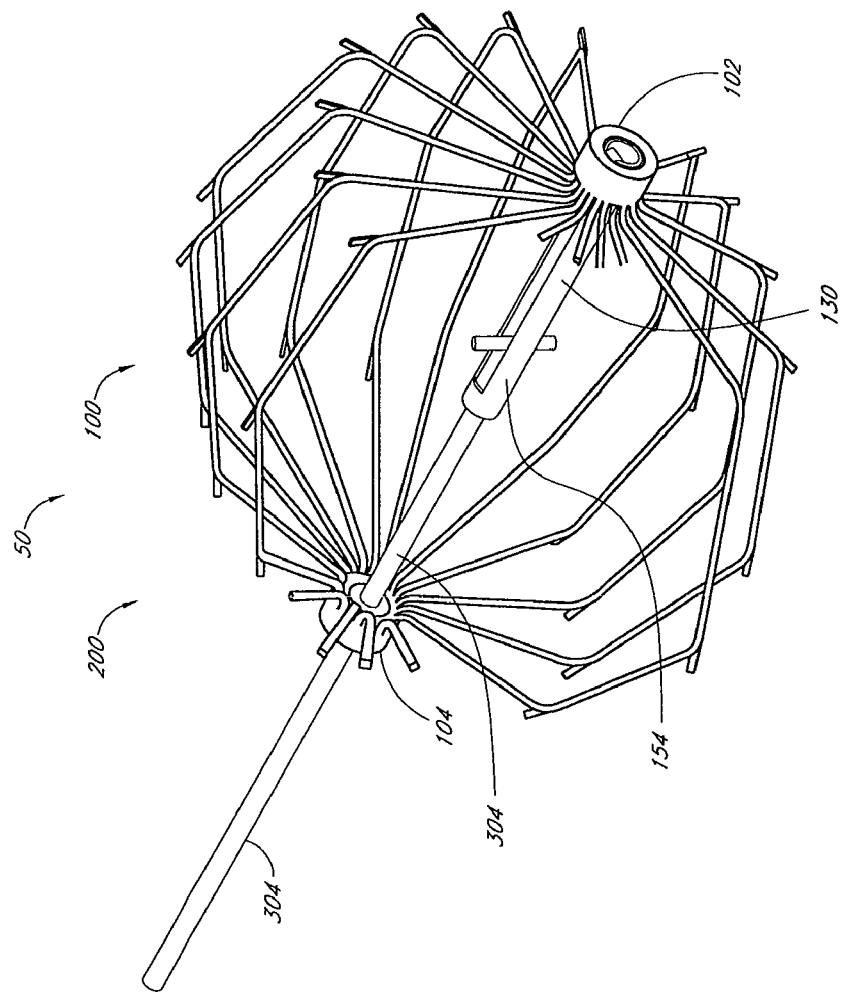
FIG. 16A is a schematic cross-sectional view of a distal portion of an adjustable implant deployment system, in accordance with another embodiment.

FIGS. 16A and 16B illustrate another embodiment of an implant delivery system 50. The system 50 of the illustrated embodiment provides some axial decoupling between an axially moveable core 304 and an implant 100. This embodiment of the implant deployment system 50 reduces the bias of torsion loads described in the previous embodiment by eliminating rotational forces related to a threaded engagement between an implant 100 and a catheter system 300 (as illustrated in FIGS. 14 and 15). Furthermore, it is clinically advantageous to provide axial decoupling between the axially moveable core 304 and the implant 100 is because axial decoupling assures that movement of the axially moveable core 304, as well as other components of the adjustable implant delivery system 50 that are coupled to the axially moveable core 304 (for example, but not limited to the deployment handle 400 and the catheter system 300, described further herein), do not substantially affect the shape or position of the implant 100. Such axial decoupling prevents inadvertent movement of the axially moveable core 304 or deployment handle 400 from affecting the shape or position of implant 100.

For example, in one embodiment, if the user inadvertently pulls or pushes the axially moveable core 304 or the deployment handle 400, the position of the implant 100 within the left atrial appendage 10 preferably will not be substantially affected. In addition, axial decoupling also preferably prevents the motion of a beating heart 5 from translating into movement of the axially moveable core 304, the catheter 300, and/or the components coupled to the axially moveable core 304 and catheter 300, including the deployment handle 400. By decoupling the implant 100 from the axially moveable core 304 and other components coupled to the axially moveable core 304, the risk of accidentally dislodging the implant 100 from the left atrial appendage 10 is reduced.

The illustrated implant release and recapture mechanism 200 of FIGS. 16A and 16B provides quick-disconnect functionality for release of axially moveable core 304 from guide tube 130 by using non-rotational forces. As illustrated, the implant release and recapture mechanism 200 includes a guide tube 130, which comprises at least one slot 154. Two opposing slots 154 are shown in the embodiment of FIGS. 16A and 16B. Axially moveable core 304 is coupled to guide tube 130 by quick-disconnect functionality.

Axially moveable core 304 in this embodiment includes a retractable lock 220 in the form of an elongate key 222 extending through the lumen of the core 304, and two opposing ports 224 in axially moveable core 304 through which two tabs 226 extend. The distal tip 228 of the key 222 includes a contact surface 230 operable to engage contact surfaces 232 of the tabs 226. The key 222 is moveable relative to the axially moveable core 304, and can be moved distally such that contact surface 230 engages contact surfaces 232 of tabs 226, translating into radial movement of tabs 226. Radial movement of tabs 226 causes them to project into slots 154 of the guide tube 130 by bending radially outwardly, and extending in a substantially radial direction. In one embodiment, the key 222 is secured in place relative to the axially moveable core 304, so that the tabs 226 remain projected into the slots 154 of the guide tube 130. With the tabs 226 secured in place, axial movement of axially moveable core 304 preferably is limited by interference between the tabs 226 and the proximal and distal surfaces 156, 158 of guide tube 130.

In one embodiment, the key 222 is made from an elongate wire, rod, or tube flexible enough for delivery through the adjustable implant delivery system 50 described above, and strong enough to apply enough force to tabs 226 to achieve the functionality described above. In one embodiment, the key 222 is made from stainless steel. The key 222 preferably is locked in place relative to the axially moveable core 304 by using a control, such as a thumbswitch or other such device as is well known to those of skill in the art. For example, in one embodiment, the axially moveable core 304 is secured to the proximal portion of a deployment handle 400 (not shown) such that the position of the axially moveable core 304 is fixed with respect to the deployment handle 400. A key 222 preferably is inserted inside of the axially moveable core 304 such that it may slide axially within the axially moveable core 304. The proximal portion of the key 222 preferably is coupled to a control, such as, for example, a thumbswitch. The thumbswitch preferably is provided such that it may slide axially with respect to the deployment handle 400 (and therefore with respect to the axially moveable core 304) over a predetermined range. By coupling the thumbswitch to the proximal portion of the key 222, axial movement of the key 222 with respect to the axially moveable core 304 is achieved over the predetermined range. In addition, by locking the thumbswitch in place (by using mechanisms well known to those of skill in the art, such as release buttons, tabs, or their equivalents), the key 222 may be locked in place with respect to the axially moveable core 304. Alternatively, switches, levers, buttons, dials, and similar devices well known to those of skill in the art may be used instead of a thumbswitch as the control for the retractable lock 220.

To decouple axially moveable core 304 from the guide tube 130, retractable lock 220 is released by moving key 222 proximally relative to axially moveable core 304, thereby removing radial forces from contact surfaces 232 of tabs 226. In one embodiment, tabs 226 are biased to bend inward upon the removal of the radial forces from their contact surfaces 232. For example, tabs 226 preferably are constructed from a spring material, or a shape memory metal, such as, for example, nickel titanium. Alternatively, in another embodiment, key 222 is moved distally to decouple axially moveable core 304 from the guide tube 130. For example, in one embodiment, key 222 includes a cutout, notch, or slot along at least a portion of its distal end. In one embodiment, as the key 222 is moved distally, the cutout, notch, or slot is moved such that it engages the tabs 226, allowing them to flex inwardly preferably under their own bias. In another embodiment, tabs 226 are biased to bend outward upon removal of a radial force from a contact surface 232, and bend inward upon application of a radial force to contact surface 232. In such embodiment, the key 222 preferably is advanced distally to apply force on a contact surface 232 such that tabs 226 are directed inward. In one embodiment, the key 222 is advanced proximally to apply force on a contact surface 232 such that tabs 226 are directed inward.

In other embodiments, a guide tube 130 need not be connected to the implant 100, and for example, can be provided as part of the axially moveable core 304, or even the deployment handle 402 in order to decouple axial movement between the implant 100 and the rest of the delivery system 50. For example, in one embodiment, an axially moveable core may include two concentric or axially aligned tubes, slidably moveable with respect to one another, such as, for example, an outer tube and an inner tube, such as describe above with respect to FIGS. 13A and 13B. The outer tube may include a mating surface on or near its distal end to engage a mating surface on the distal hub, or elsewhere on the implant. The outer tube slidably engages an inner tube, which enters the outer tube at the outer tube's proximal end. In one embodiment, a solid core is used instead of an inner tube. Relative proximal and distal movement of the inner and outer tube is preferably limited by a motion limit.

In one embodiment, the motion limit includes at least one cross pin. In other embodiments, the motion limit includes at least one flare, annular ring, bump, or other suitable mechanism as is well known to those of skill in the art. The inner tube extends preferably to a handle as described above for operating the axially moveable core. The engagement of the outer tube and the inner tube of the axially moveable core may occur anywhere between the handle and the implant along the length of the core.

In another embodiment, the inner tube includes a mating surface on its distal end to engage a mating surface on the distal hub of the implant. The inner tube slidably engages an outer tube, which at least partially covers the inner tube at the inner tube's proximal end. Relative proximal and distal movement of the inner and outer tube is preferably limited by a motion limit as described above, with the outer tube extending outside of the patient and operably connected to a handle.

d. Multiple Guide Tube Mechanisms

Again referring to FIGS. 13A and 13B, various embodiments of a multiple guide tube system may provide additional buckling and bending support for any implant actuation shaft 334 traversing an axis of an implant 100, as described above. Also, providing dual, opposed guide tube allows decoupling of implant motion with respect to the delivery catheter over a longer axial distance. For example, a single guide tube having may allow for axial movement decoupling over the length of the single guide tube, but dual guide tubes allow for axial movement decoupling over the length defined by both guide tubes.

Single guide tube embodiments are illustrated in FIGS. 16A and 16B, and described in U.S. application Ser. No. 10/642,384, filed Aug. 15, 2003, published as U.S. Publication No. 2005/0038470, incorporated by reference herein. Implants including single guide tubes generally include a nut that is configured to slide within the guide tube along a limited axial range of motion. A tab, or protrusion, generally extends from the external side wall of the nut into a slot provided in the guide tube wall. The interference between the tab and the slot defines an axial range of motion provided by the guide tube/sliding nut assembly. An axial moveable core, or a torque rod, is generally coupled to the nut (e.g., a threaded portion of the core screws into a mating portion of the nut), and an implant is generally coupled to the distal end of the single guide tube; therefore, the axial range of motion defined by the guide tube/sliding nut assembly also defines an axial range of motion between the axial moveable core and the implant.

The axial range of motion between the axial moveable core and the implant defines a distance over which axial movement of the implant is decoupled from the axial moveable core. This decoupling distance provides many clinical advantages. For example, once the implant is expanded within the patient's heart, such as within the LAA, it generally remains attached to the axial moveable core. By remaining attached to the axial moveable core the clinician can verify the implant position and sealing against the LAA wall prior to final deployment, or release, from the axial moveable core.

Forces provided by the patient's moving heart act upon the core-coupled implant. It is desirable that the implant is free to move with the movement of the patient's beating heart, and that the implant does not resist such forces. Resistance to heart movement could cause the implant to become dislodged from its implantation site, or to change it orientation in an undesired manner.

The guide tube/sliding nut assembly of the single guide tube embodiments addresses this issue by providing limited decoupling between the implant and an axial moveable core, as discussed above. However, the decoupling length is generally limited by the length of the guide tube slot, which is limited by the guide tube length. It would be advantageous to increase the decoupling length. In one embodiment, decoupling length is increased by employing a dual guide tube configuration, such as described above with respect to FIGS. 13A and 13B, and below. In addition, a dual guide tube configuration can be employed with any of the deployment systems, delivery systems, implants, catheters, and catheter systems described herein.

Although the embodiments of FIGS. 13A and 13B illustrate one pull cord or tether 312 configuration, certain preferred embodiments of an implant delivery system 50 with a multiple guide tubes do not include a pull cord 312. Removing the tether 312 can reduce system bias from moment arms. Instead, an embodiment of an implant delivery system 50 with a multiple guide tubes 130 and 160, or 164 and 162, may be used with a threaded rod 342 configuration as described above relating to FIGS. 14 and 15. In other embodiments, an implant delivery system 50 with multiple guide tubes does not use a threaded torque rod configuration in order to reduce system bias from rotation of the implant 100 with respect to a torque rod 342.

In certain embodiments an implant delivery system 50 with multiple guide tubes can provide for some axial load decoupling by providing slideable axial support to an implant 100, which is attached at its proximal end 104 to a catheter system 300. After an implant actuation shaft 334 is withdrawn from the distal end 102 of an implant, the freely slideable concentric guide tubes 130 and 160 (or 162 and 164) may absorb some of the axial loading caused by the beating of a heart 5, thereby allowing the implant 100 frame 101 to deform with the beating of a heart 5 without imparting a complete load to the remainder of the implant delivery system 50.

In one embodiment, a multiple guide tube configuration may be used to simplify an implant release and recapture mechanism 200. For example, the implant release and recapture mechanism 200 provides extendable support to a non-threaded shaft 334 that provides axial force to the distal end 104 of an implant 100 without providing off-center moment arms or rotational loads relative to the implant 100 during implant deployment or detachment (such as is illustrated in one embodiment in FIGS. 21A-21C, as described below).

In one embodiment, multiple guide tubes provide additional axial support and guided slidable surfaces to the implant 100 while preventing the shaft 334 from buckling over a the guide tube lengths. Substantially coaxial tubes provide for easier alignment of the ends 102 and 104 of an implant 100, and simplify the re-insertion of a shaft 334 into an implant 100 during recapture of detached or deployed implants. In addition, the multiple guide tube configuration provides support for the distal loading provided by the shaft 334, and works with any collapse or release mechanism. However, it would be advantageous to provide the necessary proximal loading to the proximal end 104 of an implant 100 in order to radially reduce an implant 100 in a manner that did not impart moment arms or rotational loads to the implant 100 during deployment or detachment, as described in the following embodiments.

e. Concentric Collapse and Release Mechanisms

FIGS. 17-21 illustrate cross-sectional views of various embodiments of the distal end of an implant delivery system 50 that includes an implant 100, an implant release and recapture mechanism 200, and a catheter system 300, which is attachable to a deployment handle 400 (not illustrated). The illustrated embodiments provide mechanisms to release an implant 100 from a catheter system 300 such that the implant's position and orientation do not change as a result of the release process. For example, the illustrated embodiments reduce bias and moment arms that cause deformation of the implant 100 and loads within the implant delivery system 50. Such bias and moment arms can cause the implant 100 to jump or change orientation when released from the implant delivery system 50. These embodiments include a flexible interface between the implant 100 and the catheter system 300. They also reduce off-axis loading, thereby reducing moment arms and bending bias within the system 50. Some embodiments include a tether line 210 system (not shown) or a torque rod 340 configuration (not shown), as described above.

Referring to FIGS. 17-20, the illustrated embodiments have an implant 100 with a frame 101, a proximal end 104 and a distal end 102, a stopping surface 126 at the distal end 102 of the implant 100, and a disconnect mount interface 180 on the proximal end 104 of the implant 100. The implant of FIGS. 17-20 is schematically shown, and may have any suitable configuration as described herein. The disconnect mount interface 180 has a finger interface 182 which interacts with a flexible finger 238 on a disconnect mount 236 on the catheter system 300, as described below. Embodiments of the finger interface 182 may be in the form of a protruding finger, an interlocking feature, a groove, a slot, a window, or other similar features for releasably holding a disconnect mount 236 flexible finger 238. The distal end 102 of the implant 100 may also have an end cap 148. Various embodiments and combinations of embodiments of the implant 100 may be used, including but not limited to single and multiple guide tube configurations, as describe above.

In some embodiments, the catheter system 300 includes a disconnect mount 236 provided on the distal end 310 of a delivery catheter 302. The disconnect mount 236 may be any mechanical mount that releases one body from another without creating any or substantial moment arms or bending bias. The disconnect mount 236 may provide releaseable concentric tension or concentric loading to an implant 100.

The loading imparted by the disconnect mount 236 to the implant 100 may be in a proximal or distal direction. Distal loading may be imparted to advance the entire catheter system 300 and implant 100 distally into a heart 5. Proximal loading may be used in conjunction with a distally-loading shaft that works with the disconnect mount 236 in placing an implant 100 in tension in order to radially reduce a diameter of the implant 100. In one embodiment, a disconnect mount 236 may include an annular ring, which may be controlled to switch between an expanded and a reduced diameter configuration. In one embodiment, the disconnect mount 236 acts like a stent, such as by radially expanding or contracting. For example, the disconnect mount 236 can include a shape memory alloy, such as nickel titanium, which self-expands. In other embodiments, the disconnect mount 236 expands under positive force, such as in response to radial forces provided by an inflation balloon.

The terms "concentric tension," "concentric loading," and "concentric force" are broad terms intended to have their ordinary meanings. In addition, these terms refer to forces that are provided either in an inward or outward direction with respect to a longitudinal axis, and forces symmetrical about a longitudinal axis. Some of the symmetrical forces may be in directions with components along an axis extending distally or proximally along the longitudinal axis, and may also be perpendicular to the longitudinal axis. For example, in one embodiment, a disconnect mount is a generally cylindrical structure having a longitudinal axis and flexible fingers extending longitudinally from its end. The flexible fingers are generally biased to flex inward, towards the longitudinal axis, or outward, away from the longitudinal axis. The fingers are generally aligned with openings in a mating portion of the implantable device. The openings generally extend around or within a portion of the circumference of the mating portion of the implantable device. As the fingers flex, they provide concentric force that maintains a portion of the fingers within the windows of the implant mating surface. When the fingers are engaged with the implant mating portion, proximal or distal force can thereafter be applied to the implant with the disconnect mount to move the implant, or at least the portion of the implant coupled to the disconnect mount, in a proximal or distal direction.

Concentric forces can be used to release the implant from a delivery system without applying bias to the implant, as described herein. For example, by concentrically releasing tension from the proximal end of the implant, the implant will not substantially jump, move, or otherwise change its orientation with respect to the delivery system when released.

In some embodiments, the disconnect mount includes two, three, four, or a plurality of actuating fingers, such as ten or more actuating fingers. As illustrated, the disconnect mount 236 has at least two flexible fingers 238 which engage recesses, windows, or corresponding structure in a disconnect mount interface 180 located at the proximal end 104 of an implant 100.

The disconnect mount 236 can be created from rod stock using a combination Swiss screw machine and Electrical Discharge Machining (EDM) operation to fashion at least two substantially symmetric flex fingers 238 with protruding portions 240. The disconnect mount interface 180 may have a finger interface 182 that is specially adapted to releasably hold a disconnect mount 236 flexible finger 238 in place. The catheter system 300 has an implant actuation shaft 334 that extends through the catheter body 302 and through the implant 100 to touch the stopping surface 126 at the distal end 102 of the implant 100. When the implant actuation shaft 334 provides a sufficient load in the distal direction against the stopping surface 126 while a tensile load in a proximal direction is applied to the proximal end 104 of the implant 100, the implant 100 can be held in a radially-reduced configuration which overcomes the normal shape-memory bias toward a radially-expanded configuration for the implant 100.

When the implant actuation shaft 334 is retracted proximally into the catheter body 302, the implant 100 tends to return to its radially-expanded configuration by moving proximally (e.g., see FIGS. 17, 19, 20). When the tensile loading on the proximal end 104 of the implant 100 is reduced by allowing the proximal end 104 of the implant to move distally, the implant 100 tends to return to its radially-expanded configuration by moving distally (e.g., see FIGS. 18, 21). The retraction of the implant actuation shaft 334 and reduction in tensile loading on the proximal end 104 of the implant 100 may occur independently, simultaneously, or incrementally to control the relative axial placement of the implant 100 in a LAA 10.

Still referring to FIGS. 17-20, there is illustrated various embodiments of a disconnect mount 236 with a corresponding disconnect mount interface 180 and a lock tube 234. The disconnect mount interface 180 may have a finger interface 182 that is adapted to releasably hold a disconnect mount 236 flexible finger 238 in place. The protruding portions 240 of the flex fingers 238 are captured within cutouts, recesses, or windows located on the finger interface 182 of the disconnect mount interface 180, which is located on a proximal portion 104 of the implantable device 100. For example, the implant's 100 finger interface 182 can include cutouts that releasably engage flex fingers 238 of the delivery system. While the flex fingers 238 hold on to the proximal end 104 of the implant 100, an implant actuation shaft 334 extends through the implant 100 and pushes distally against the distal end 102 of the implant 100. As described above, the implant 100 can be made self-expanding, so that when the distal pushing force exerted by the implant actuation shaft 334 or the proximal pulling (or holding) force applied by the flex fingers 238 is removed the implant 100 automatically radially expands to a predetermined size and shape. The implant 100 can be maintained in its reduced diameter configuration by holding the proximal end 104 of the implant 100 with the flex fingers 238 and pushing against the distal end 102 of the implant 100 with the implant actuation shaft 334. In this configuration, relative movement between the inner implant actuation shaft 334 and the concentric, outer flex fingers 238 controls implant 100 expansion and collapse.

An embodiment of flex fingers 238 can be biased to extend either radially inwardly or radially outwardly. In embodiments where the flex fingers 238 are biased to extend radially inwardly, the flex fingers 238 engage a disconnect mount interface 180 to lock an implant 100 to the implant delivery system 50 when a structure prevents the flex fingers 238 from extending radially inwardly. In one embodiment the flex fingers 238 are held in place with a disconnect mount interface 180 of the implant 100 by the presence of an implant actuation shaft 334 which extends through the implant 100 and prevents the flex fingers 238 from extending radially inwardly. When the implant actuation shaft 334 is withdrawn proximally toward the catheter system 300 past the disconnect mount 236, the open space created by the removal of the implant actuation shaft 334 leaves room for the flex fingers 238 to extend radially inwardly under its bias. This radial movement of the flex fingers 238 releases the disconnect mount 236 from the disconnect mount interface 180, thereby releasing the implant 100 from the implant delivery system 50.

In embodiments where the flex fingers 238 are biased to extend radially outwardly, the flex fingers 238 engage a disconnect mount interface 180 to lock an implant 100 to the implant delivery system 50 in its natural state. When a structure or a load causes the flex fingers 238 to extend radially inwardly, the radial movement of the flex fingers 238 releases the disconnect mount 236 from the disconnect mount interface 180, thereby releasing the implant 100 from the implant delivery system 50.

In some embodiments, the flex fingers 238 are held in the finger interface 182 by a lock tube 234. The lock tube 234 can be axially slideable with respect to the catheter body 302 and with respect to a disconnect mount 236. In one embodiment, the lock tube 234 has a threaded portion (not illustrated) that threads into the disconnect mount 236 and extends under and between the flex fingers 238, thereby preventing the flex fingers 238 from collapsing inward (in a manner similar to the embodiment illustrated in FIGS. 17-18).

In another embodiment the lock tube 234 has a threaded portion (not illustrated) that threads over the disconnect mount 236 and extends over the flex fingers 238, thereby preventing the flex fingers 238 from expanding outward (in a manner similar to the embodiment illustrated in FIGS. 19-20). In other embodiments, a lock tube 234 can be threaded to a catheter body 302, or a lock tube 234 may not be threaded and retains its axial positioning with respect to a disconnect mount 236 until the user actuates the lock tube to release the flex fingers 238. In other embodiments, an implant actuation shaft 334 can include a protruding feature, such as a tab, key or pin, that engages a lock tube 234 and allows torque to be transferred from the implant actuation shaft 334 to the lock tube 234.

Figure 17A:
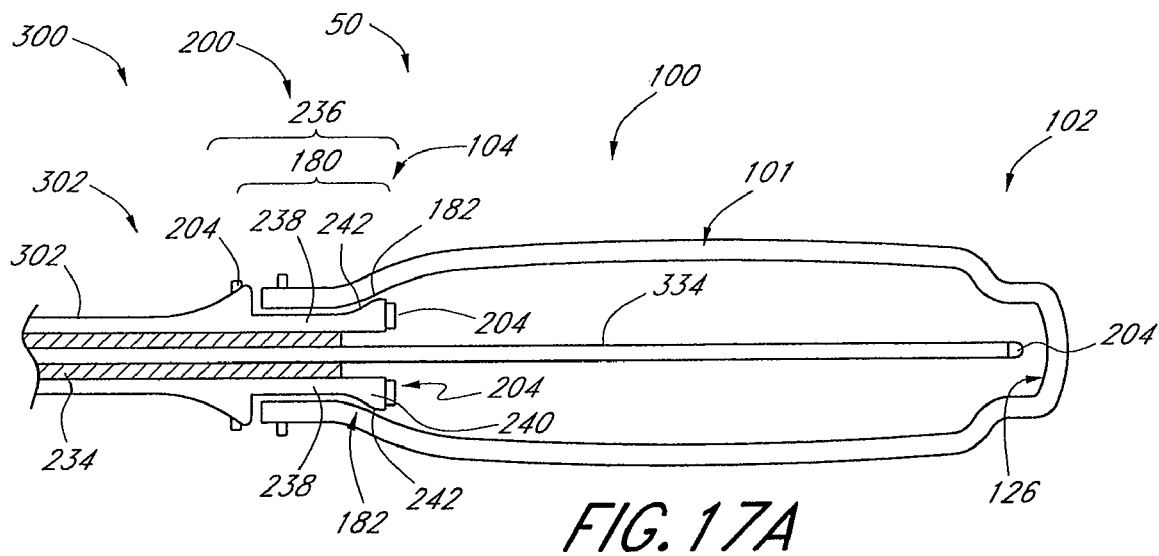
FIGS. 17A-C are schematic cross-sectional views of an implant release and recapture mechanism having an internal lock tube, in accordance with another embodiment.
Figure 17B:
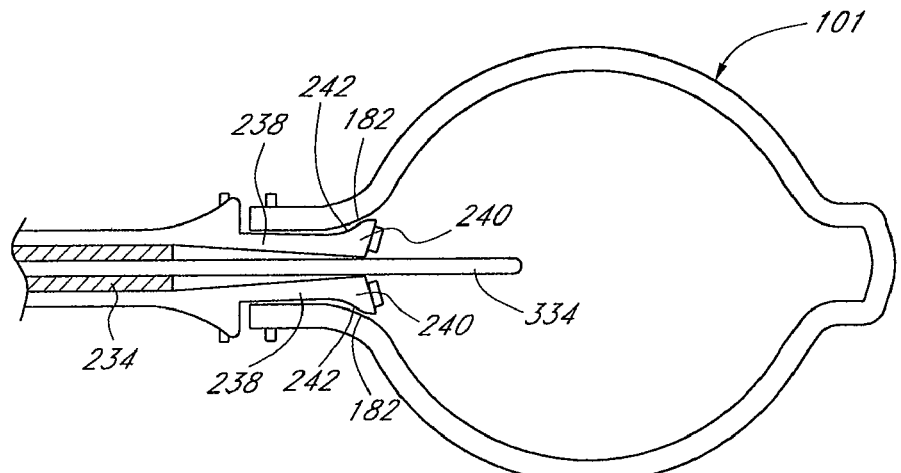
Figure 17C:
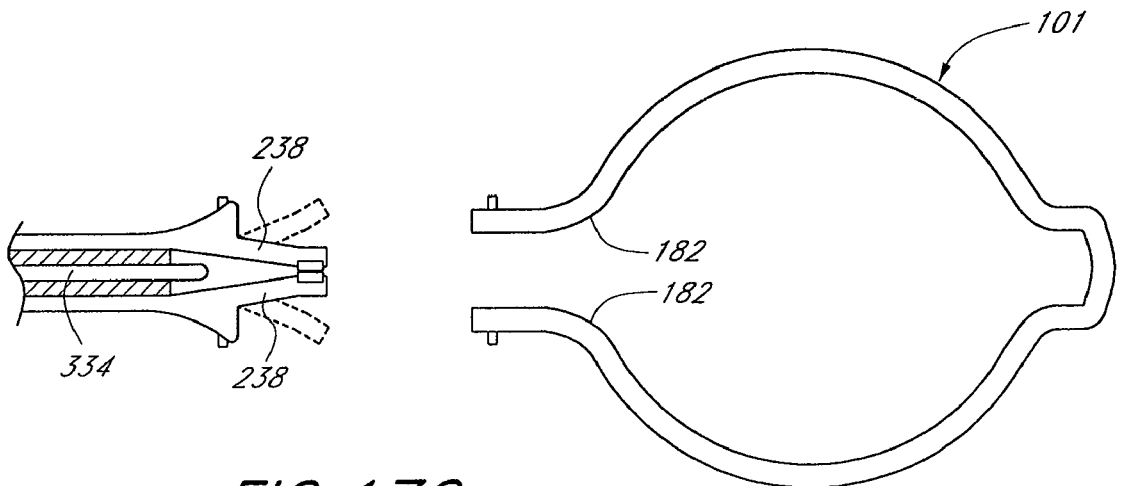

FIGS. 17A-17C illustrate an embodiment of a disconnect mount 236 having flex fingers 238, a corresponding disconnect mount interface 180, and a lock tube 234 at least partially contained within a catheter body 302. In certain embodiments illustrated in FIGS. 17A-17C, the flex fingers 238 can be biased to extend radially outwardly or inwardly to apply concentric loading, as discussed above.

In one embodiment, the flex fingers 238 are biased outwardly. The flex fingers 238 can also include a proximal inclined surface 242 at the transition from the flex finger 238 to the protruding portion 240. Referring to embodiments in FIG. 17B, after the implant 100 is deployed or radially expanded in a LAA 10 (not illustrated here), anchors 118 (not illustrated here) on the implant frame 101 secure the implant 100 within the LAA 10. The interface between the implant 100 and the disconnect mount 236 provides concentric loading to the implant 100. In one embodiment the concentric loading is concentric tension. At this point, the lock tube 234 can be withdrawn proximally away from contact with the flex fingers 238, allowing the flex fingers 238 to deflect inwardly.

When the flex fingers 238 are moved proximally with respect to the implant 100, such as when the catheter system 300 is withdrawn proximally away from the expanded implant 100 in the LAA 10, the inside edge of the disconnect mount interface 180 can press onto the proximal inclined surface 242, which provides a radially inward force to the flex finger 238. As illustrated, the embodied disconnect mount interface 180 uses a finger interface 182 in the form of an internal surface of a proximal end 104 of the implant 100. The radially inward force causes the flex fingers 238 or at least a distal portion of the flex fingers 238 to move radially inwardly.

The amount of deflection in the flex fingers 238 that effective to release the disconnect mount 236 from the disconnect mount interface 180 may depend on the thickness of the lock tube 240 alone (as is illustrated in FIG. 17B), or it may depend on the removal of the implant actuation shaft 334 proximal to the flex fingers 238 (as is illustrated in FIG. 17C) in order to release the implant 100. Once the flex fingers 238 are sufficiently radially deflected, the implant 100 is disconnected from the delivery system 50 without imparting any or any substantial moment arms, bending bias, or rotational bias with respect to the implant 100. As depicted in FIG. 17C, once the implant 100 is detached, the flex fingers 238 will bias toward their natural state (inward bias is illustrated in solid lines and outward bias is illustrated in dotted lines).

In another embodiment illustrated in FIGS. 17A-17C, the flex fingers 238 are biased inwardly. Referring to embodiments in FIG. 17B, after the implant 100 is deployed and radially expanded in a LAA, anchors on the implant frame 101 secure the implant 100 within the LAA. The interface between the implant 100 and the disconnect mount 236 provides concentric loading to the implant 100. In one embodiment the concentric loading is concentric tension. At this point, the lock tube 234 can be withdrawn proximally away from contact with the flex fingers 238, allowing the flex fingers 238 to deflect inwardly to their natural, biased state. The amount of deflection in the flex fingers 238 that is effective to release the disconnect mount 236 from the disconnect mount interface 180 may depend on the thickness of the lock tube 240 alone (as is illustrated in FIG. 17B), or it may depend on the removal of the implant actuation shaft 334 proximal to the flex fingers 238 (as is illustrated in FIG. 17C) in order to release the implant 100. Once the flex fingers 238 are sufficiently radially deflected, the implant 100 is disconnected from the delivery system 50 without imparting any or any substantial moment arms, bending bias, or rotational bias with respect to the implant 100. As depicted in FIG. 17C, once the implant 100 is detached, the flex fingers 238 will bias toward their natural state (inward bias is illustrated in solid lines and outward bias is illustrated in dotted lines). When the flex fingers 238 are biased inwardly, the lock tube 334 can be slideably engaged under the flex fingers 238 to deflect the fingers outwardly.

In some embodiments, when the implant 100 is in its collapsed configuration the tension created by a load between the implant actuation shaft 334 and the flex fingers 238 may create pullout forces sufficient to cause inward flex of the flex fingers 238 and potentially pinch underlying structure, such as the implant actuation shaft 334, which could cause the implant 100 to bind. However, the lock tube 234 can prevent this from happening and can serve as a buffer between the flex fingers 238 and the underlying implant actuation shaft 334. This provides smooth and uninterrupted movement of the implant actuation shaft 334 in and out of the implant 100 during expansion. It also allows for smooth disconnect during release of the implant 100 ("boing-less" release, or releasing without the implant "jumping", moving, or changing its position or orientation).

In some embodiments, markers 204 are provided at locations visible under fluoroscopy or other means known in the art of visualizing the manipulation or implantation of devices within a body. The markers 204, which can be radiopaque in nature, can be placed on any surfaces to assist in deployment or recapture of an implant 100, as is described above for the embodiment of a marker 360 as shown in FIG. 14, which advantageously assists in locating the position of a distal end 344 of an axially moveable core 342. In various embodiments, a marker 204 comprises a radiopaque band, dot, coating, or material that is attached to a disconnect mount 236, a distal end 104 of an implant 100, and a portion of an implant actuation shaft 334. Marker 204 preferably is made from a material readily identified after insertion into a patient's body by using visualization techniques that are well known to those of skill in the art. In one embodiment, the marker 204 is made from gold, or tungsten, or any such suitable material, as is well known to those of skill in the art. In another embodiment, marker 204 is welded, soldered, or glued onto a structure for marking. In one embodiment, the use of markers 204 segments is useful to discern the radial orientation of the implant 100 within the body.

Figure 18A:
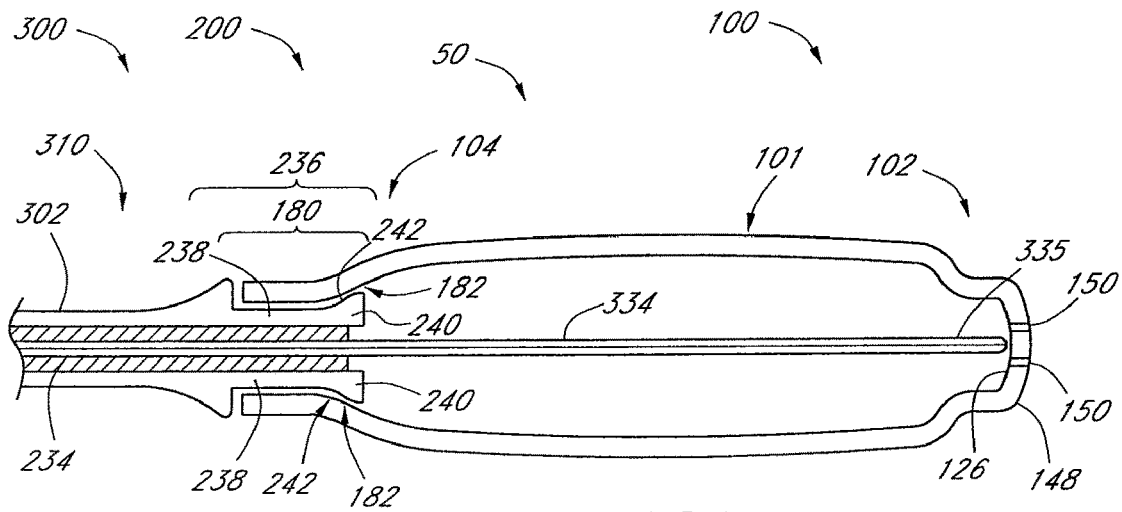
FIGS. 18A-C are schematic cross-sectional views of another implant release and recapture mechanism having an internal lock tube, in accordance with another embodiment.
Figure 18B:
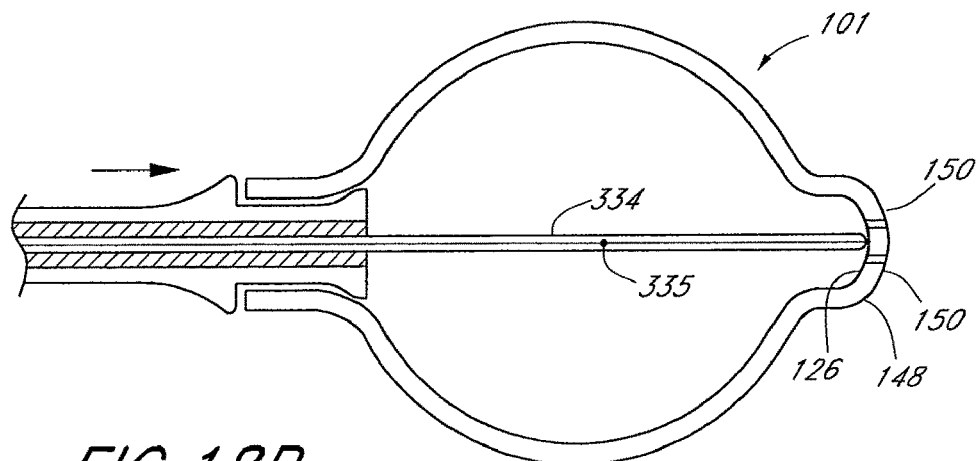
Figure 18C:
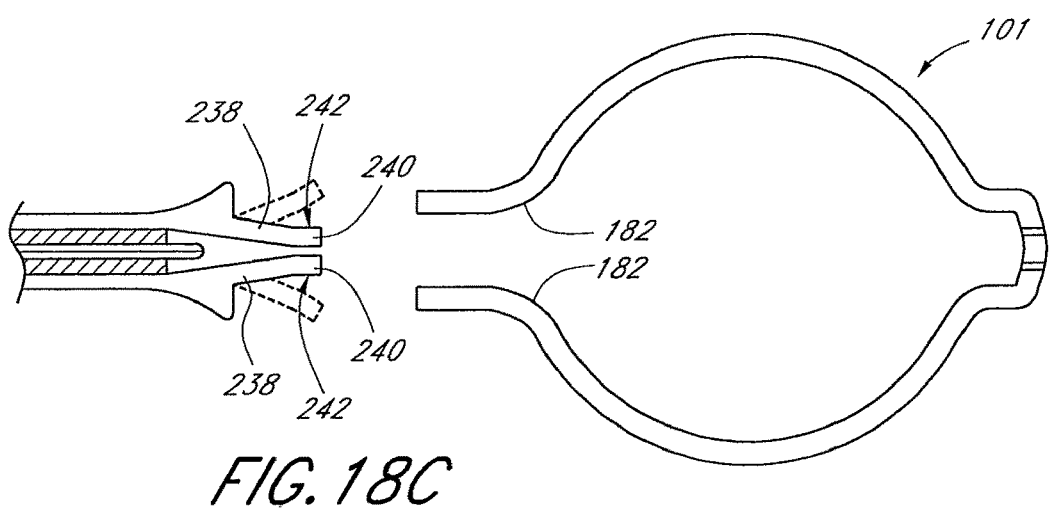

Referring to FIGS. 18A-18C, there is illustrated an embodiment of a disconnect mount 236 with flex fingers 238, a corresponding disconnect mount interface 180, and a lock tube 234 at least partially contained within a catheter body 302. The embodiment illustrated in FIGS. 18A-18C is similar in many ways with the embodiment illustrated in FIGS. 17A-17C, and includes many of the same components described above. The embodiment illustrated in FIGS. 18A-18C can optionally include markers (not illustrated). The illustrated embodiment also includes a lumen 335 in the implant actuation shaft 334, and lumens 150 in an end cap 148 at the distal end 102 of the implant 100. In addition, the illustrated embodiments can be deployed in a proximal or distal direction, as discussed in greater detail below. Any of the features of embodiments illustrated in FIGS. 17 and 18 can be used in conjunction with each other, along with combinations of embodiments illustrated in FIGS. 19-21, or any other embodiments of the invention described herein.

Referring to FIGS. 18A-18C, an embodiment of a catheter system 300 has an implant actuation shaft 334 which extends through the catheter body 302 and can extend through the implant 100 to touch the stopping surface 126 at the distal end 102 of the implant 100. When the implant actuation shaft 334 provides a sufficient load in the distal direction against the stopping surface 126 while a proximally-directed load is applied to the proximal end 104 of the implant 100, the implant 100 can be held in sufficient tension to overcome the normal shape-memory bias toward a radially-expanded configuration for the implant 100, resulting in an implant 100 with a radially-reduced configuration. The embodiment of the system 50 illustrated in FIGS. 17A-17C depicts steps where the implant actuation shaft 334 is retracted proximally into the catheter body 302 and the implant 100 tends to return to its radially-expanded configuration as of its distal end 102 moving proximally.

The embodiment of the system 50 illustrated in FIGS. 18A-18C depict steps where the concentric tensile loading on the proximal end 104 of the implant 100 is reduced by allowing the proximal end 104 of the implant 100 to move distally such that the implant 100 as a whole tends to return to its radially-expanded configuration by moving distally. The retraction of the implant actuation shaft 334 and reduction in concentric tensile loading on the proximal end 104 of the implant 100 may occur independently, simultaneously, or incrementally to control the relative axial placement of the implant 100 in a LAA 10.

The lumen 335 in the implant actuation shaft 334 may contain radiopaque or contrast materials injected into the catheter system 300 through ports in the deployment handle 400, as described above and below. The exit point for contrast to exit the lumen 335 may be at the distal tip of the implant actuation shaft 334 or along any exit port (not illustrated) along the implant actuation shaft 334. One embodiment of a lumen 335 is similar to the lumen 350 of the tubular torque rod 340 described above and illustrated in FIG. 14. The lumen 335 preferably allows visualization dye to flow through the lumen 335 of the implant actuation shaft 334 and through the implant frame 101 or through at least one lumen 150 of the implant end cap 148, and into the LAA 10 (not illustrated here). Such usage of visualization dye is useful for clinical diagnosis and testing of the position of the implant 100 within the LAA 10 or other body openings.

FIGS. 19A-19C and 20A-20C illustrate additional embodiments of a disconnect mount 236 having flex fingers 238, a corresponding disconnect mount interface 180, and a catheter body 302, which is at least partially contained within a lock tube 234. The disconnect mount 236 provides concentric loading to the implant 100 without imparting rotational loads to the implant 100. The flex fingers 238 can be biased to extend radially outwardly or inwardly, as discussed above. In one embodiment, the flex fingers 238 are biased inwardly. The flex fingers 238 can also include a proximal inclined surface 242 at the transition from the flex finger 238 to the protruding portion 240. As illustrated, the embodied disconnect mount interface 180 uses a finger interface 182 in the form of slots or windows in a wall of a proximal end 104 of the implant 100. Referring to embodiments in FIGS. 19B and 20B, after the implant 100 is deployed and radially expanded in a LAA 10 (not illustrated here), anchors 118 (not illustrated here) on the implant frame 101 secure the implant 100 within the LAA 10. The interface between the implant 100 and the disconnect mount 236 provides concentric loading to the implant 100. In one embodiment the concentric loading is concentric tension.

Figure 19A:
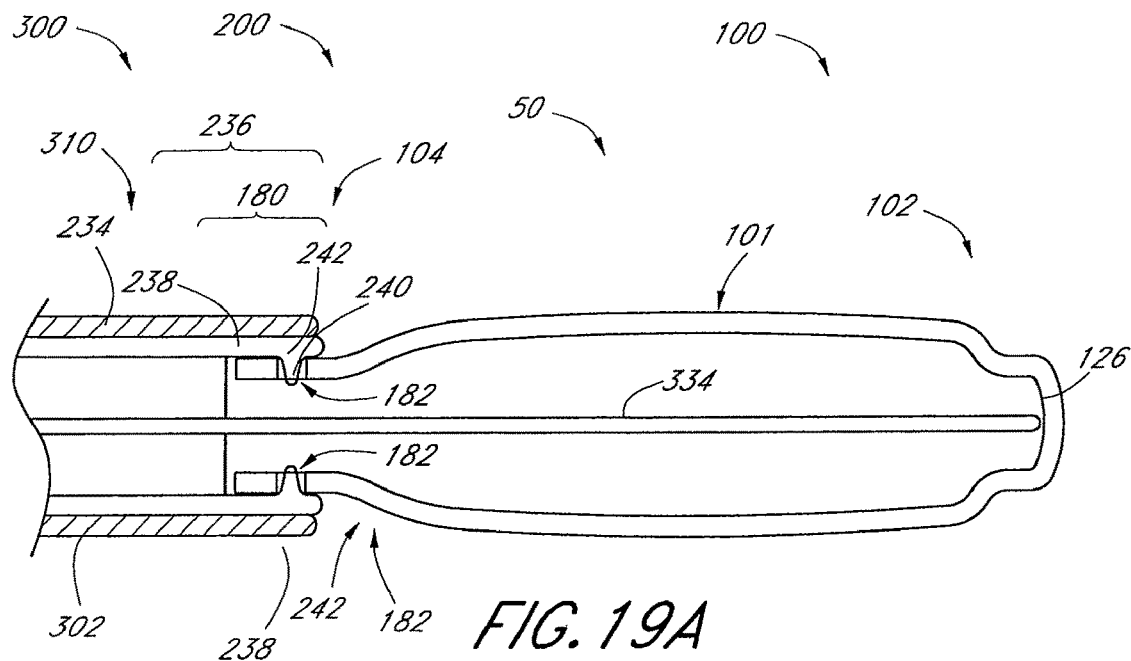
FIGS. 19A-C are schematic cross-sectional views of an implant release and recapture mechanism of an implant deployment system having an external lock tube, in accordance with another embodiment.
Figure 19B:
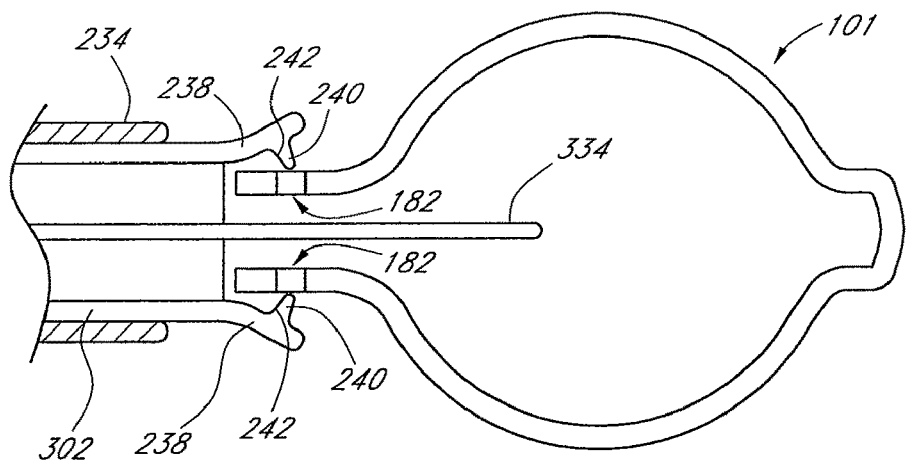
Figure 19C:
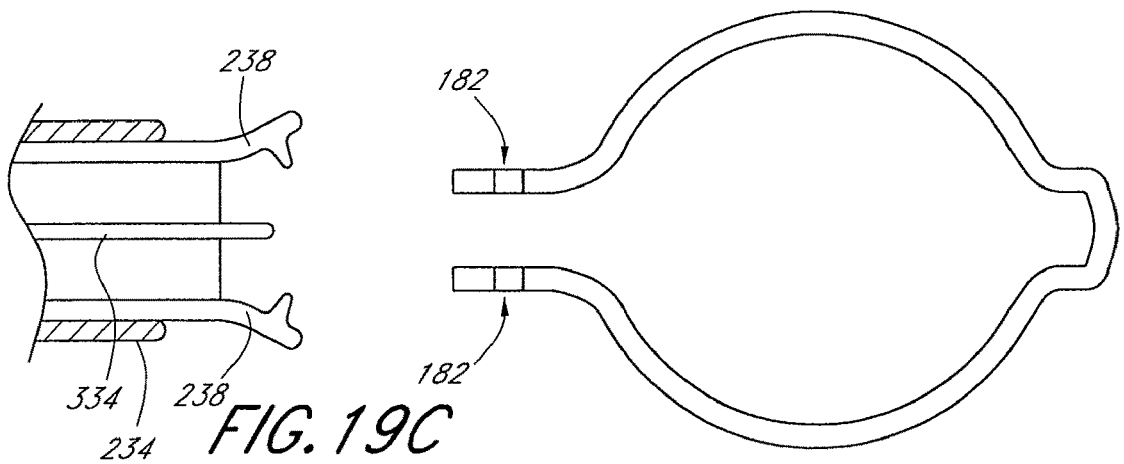

The lock tube 234 can be withdrawn proximally away from contact with the flex fingers 238, allowing the flex fingers 238 to deflect outwardly. When the flex fingers 238 are moved proximally with respect to the implant 100, such as when the catheter system 300 is withdrawn proximally away from the expanded implant 100 in the LAA 10, the inside edge of the disconnect mount interface 180 can press onto the proximal inclined surface 242, which provides a radially outward force to the flex fingers 238. The radially outward force causes the flex fingers 238 or at least a distal portion of the flex fingers 238 to move radially outwardly. Once the flex fingers 238 are sufficiently radially deflected, the implant 100 is disconnected from the delivery system 50 without imparting any or any substantial moment arms or bending bias with respect to the implant 100. As depicted in FIGS. 19C and 20C, once the implant 100 is detached, the flex fingers 238 will bias toward their natural state (inward bias is illustrated in solid lines and outward bias is illustrated in dotted lines).

In another embodiment illustrated in FIGS. 19A-19C and 20A-20C, the flex fingers 238 are biased outwardly. Referring to embodiments in FIGS. 19B and 20B, after the implant 100 is deployed and radially expanded in a LAA, anchors (not illustrated) on the implant frame 101 secure the implant 100 within the LAA. The interface between the implant 100 and the disconnect mount 236 provides concentric loading to the implant 100. In one embodiment the concentric loading is concentric tension. At this point, the lock tube 234 can be withdrawn proximally away from contact with the flex fingers 238, allowing the flex fingers 238 to deflect outwardly in their natural state.

Once the flex fingers 238 are sufficiently radially deflected, the implant 100 is disconnected from the delivery system 50 without imparting any or any substantial moment arms or bending bias with respect to the implant 100. As depicted in FIGS. 19C and 20C, once the implant 100 is detached, the flex fingers 238 will bias toward their natural state (inward bias is illustrated in solid lines and outward bias is illustrated in dotted lines). When the flex fingers 238 are biased outwardly, the lock tube 334 can be slideably engaged over the flex fingers 238 (not illustrated in FIG. 19C) or over a finger pivot axis 239 (as illustrated in FIG. 20C) in order to deflect the flex fingers 238 inwardly to facilitate extraction of the implant delivery system and/or catheter system from the body.

Figure 20A:
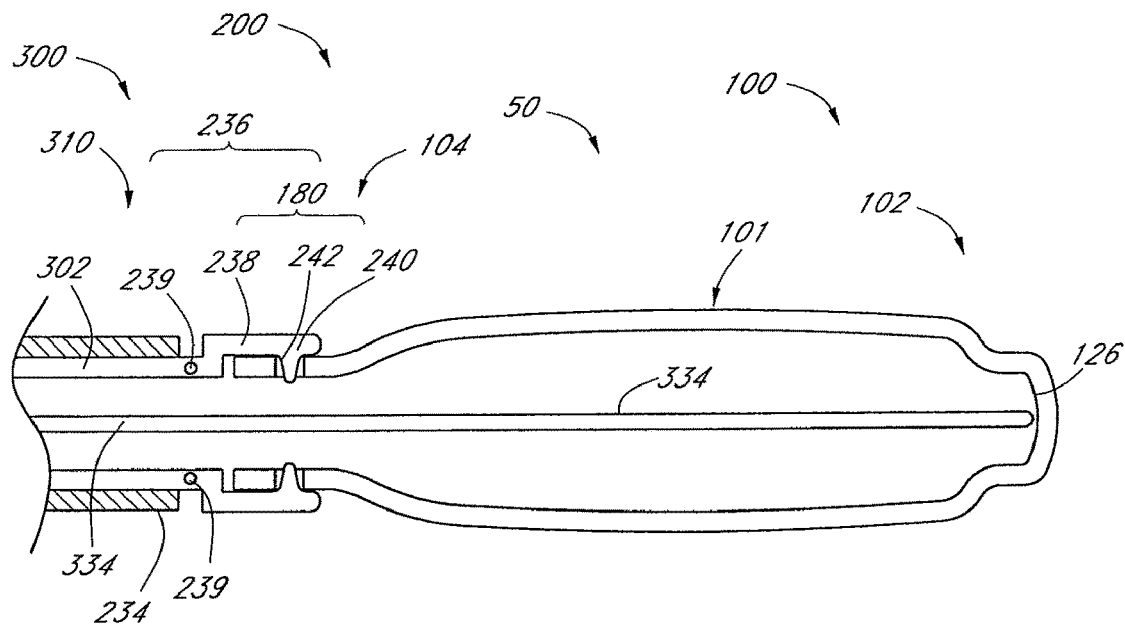
FIGS. 20A-C are schematic cross-sectional views of another implant release and recapture mechanism having an external lock tube, in accordance with another embodiment.
Figure 20B:
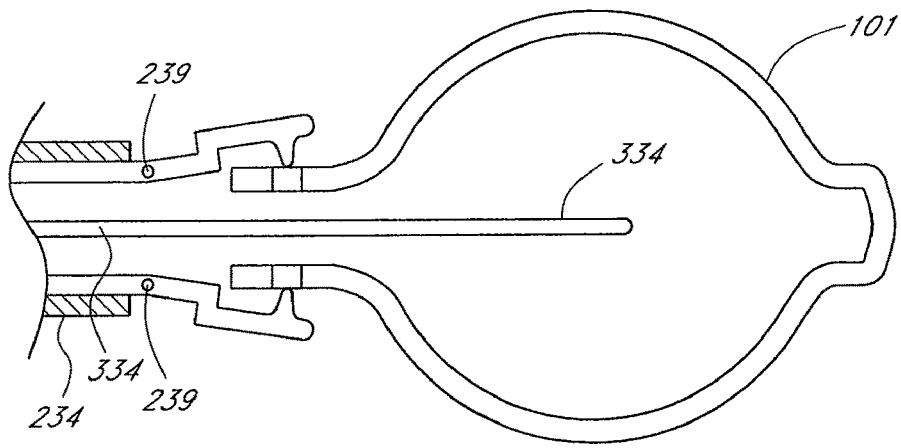
Figure 20C:
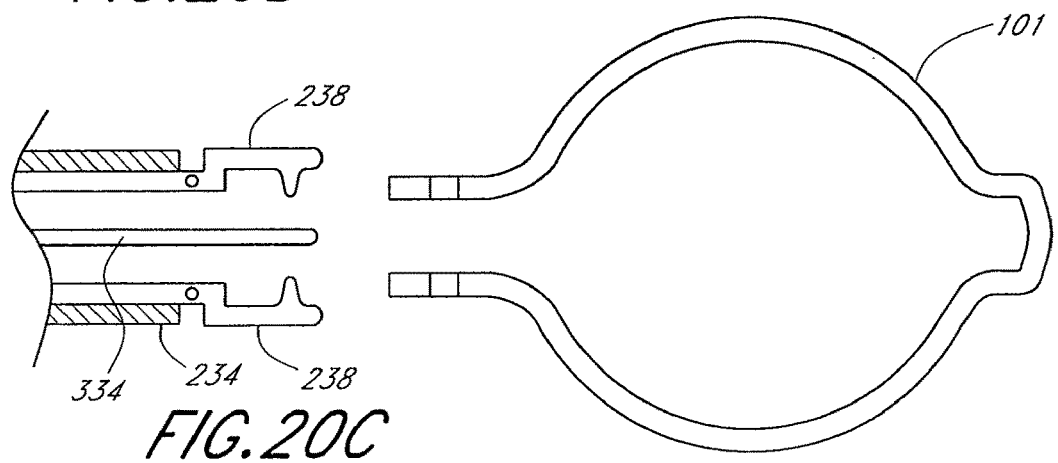

FIGS. 20A-20C illustrate an embodiment of a disconnect mount 236 with flex fingers 238, a corresponding disconnect mount interface 180, and a catheter body 302 at least partially contained within a lock tube 234, as described above. The illustrated embodiment of FIGS. 20A-20C includes a lock tube 234 that only partially surrounds the flex fingers 238 of the disconnect mount 236. In addition, a finger pivot axis 239 located proximally to the flex fingers 238 defines the axis about which the flex fingers rotate. In leaving the lock tube 234 proximal to the flex fingers 238 and at least a portion of the disconnect mount 236, the lock tube 234 can maintain a relatively smaller lock tube 234 diameter than would be the case if the lock tube 234 had to enclose the entire diameter of the disconnect mount 236, resulting in easier insertion of the catheter system 300 into the body. The finger pivot axis 239 can be formed as a crease in an extended flex finger 238 located proximally to an increase in disconnect mount 236 diameter, or as a physical hinge or pin in a linkage mechanism to create the disconnect mount 236.

All of the foregoing embodiments, including those of FIGS. 17A-20C could include an implant that has a single or dual guide tubes, as discussed above. For example, in the embodiments of FIGS. 17A-20C, the implant 100 could include a distal, outer guide tube attached to the distal end 102 of the implant 100, and a concentric, proximal, inner guide tube attached to the proximal end 104 of the implant 100.

FIGS. 21A-21C illustrate another embodiment of a distal portion of an implant delivery system 50, which includes an implant 100, an implant release and recapture mechanism 200, a catheter system 300, and a deployment handle 400 (not illustrated). The illustrated embodiments include an implant 100 that has a proximal end 104, a distal end 102 with a stopping surface 126, a frame 101, tissue anchors 118, and a disconnect mount interface 180 on the proximal end 104 of the implant 100. The disconnect mount interface 180 has a finger interface 182 which interacts with a flexible finger 238 on a disconnect mount 236 on the catheter system 300 to apply releasable concentric loads in a manner similar to the embodiments described above. Embodiments of the finger interface 182 may be in the form of a protruding finger, an interlocking feature, a groove, a slot, a window, or other similar features for releasably holding, engaging and/ or coupling a disconnect mount flexible finger 238. The distal end 102 of the implant 100 may also have an end cap 148 with zero or more lumens 150. Various embodiments and combinations of embodiments of the implant 100 may be used, including but not limited to single or multiple guide tube configurations, as described above.

As illustrated, FIGS. 21A-21C show an implant with a multiple guide tube configuration as is described above relating to FIGS. 13A and 13B. The implant 100 has an outer guide tube 162 which is also a distal guide tube 130, and an inner guide tube 164 which is also a proximal guide tube 160.

In some embodiments the catheter system 300 has a disconnect mount 236 provided on the distal end 310 of a delivery catheter 302. The disconnect mount 236 may be any mechanical mount that releases one body from another without creating any or any substantial moment arms or bending bias. The disconnect mount 236 may provide releaseable concentric tension or concentric loading to an implant 100. The loading imparted by the disconnect mount 236 to the implant 100 may be in a proximal or distal direction. For example, in some embodiments, the concentric loading applies tension in a proximal direction with respect to the implant, and in other embodiments, the concentric loading applies a pushing force in a distal direction.

Distal loading may be imparted to advance the entire catheter system 300 and implant 100 distally into a heart. Proximal loading may be used in conjunction with a distally-loading shaft that works with the disconnect mount 236 in placing an implant 100 in tension in order to radially reduce a diameter of the implant 100. In one embodiment, a disconnect mount 236 includes an annular ring that is controlled to switch between an expanded and a reduced diameter configuration. In one embodiment, the disconnect mount 236 may act like a stent, and radially expand when activated.

In other embodiments, a disconnect mount includes two, three, four, or a plurality of actuating fingers, such as ten or more actuating fingers. As illustrated, the disconnect mount 236 has at least two flexible fingers 238 which may engage within recesses, windows, or corresponding structure in a disconnect mount interface 180 on a proximal end 104 of an implant 100. The disconnect mount interface 180 may have a finger interface 182 that is specially adapted to releasably hold a disconnect mount 236 flexible finger 238 in place.

The disconnect mount 236 can be created from rod stock using a combination Swiss screw machine and Electrical Discharge Machining (EDM) operation to fashion at least two substantially symmetric flex fingers 238 with protruding portions 240. The disconnect mount interface 180 may have a finger interface 182 that is specially adapted to releasably hold a disconnect mount 236 flexible finger 238 in place.

The protruding portions 240 of the flex fingers 238 are captured within cutouts, recesses, or windows located on the finger interface 182 of the disconnect mount interface 180, which is located on a proximal portion 104 of the implantable device 100. For example, the implant's finger interface 182 can include cutouts that releasably engage flex fingers 238 of the delivery system 50.

In some embodiments, the catheter system 300 has an implant actuation shaft 334 which extends through the catheter body 302 and can extend through the implant 100 to touch the stopping surface 126 at the distal end 102 of the implant 100. When the implant actuation shaft 334 provides a sufficient load in the distal direction against the stopping surface 126 while a tensile load in a proximal direction is applied to the proximal end 104 of the implant 100, the implant 100 can be held in a radially-reduced configuration. This overcomes the shape-memory bias toward a radially-expanded configuration for the implant 100.

When the implant actuation shaft 334 is retracted proximally into the catheter body 302, the implant 100 tends to return to its radially-expanded configuration by moving proximally. When the tensile loading on the proximal end 104 of the implant 100 is reduced by allowing the proximal end 104 of the implant to move distally, the implant 100 tends to return to its radially-expanded configuration by moving distally (as is depicted in the embodiment illustrated in FIGS. 21A-21C). The retraction of the implant actuation shaft 334 and reduction in tensile loading on the proximal end 104 of the implant 100 may occur independently, simultaneously, or incrementally to control the relative axial placement of the implant 100 in a LAA 10.

In some embodiments, a lumen 335 (not illustrated) in the implant actuation shaft 334 may contain radiopaque or contrast materials injected into the catheter system 300 through ports in the deployment handle 400, as described above and below. In some embodiments, the implant actuation shaft 334 may be constructed of a flexible material, such as a puzzle lock profile 600, as described relating to FIG. 25A below.

In the illustrated embodiment of FIGS. 21A-21C, the implant actuation shaft 334 includes a threaded portion 336. In this embodiment, any rotational loads imparted due to the threadable engagement between the hub 236 and the implant actuation shaft 334 are transferred within the implant release and recapture mechanism 200 on the side with the catheter system 300, thereby avoiding rotational loading of the implant 100 within the LAA 10.

The threaded portion 336 of the implant actuation shaft 334 may be manufactured by a lathing or machining process from the same material as the implant actuation shaft 334, or threaded portion 336 may be a separate piece that is bonded, welded, soldered, braided, or otherwise attached to a portion of the implant actuation shaft 334. In the illustrated embodiment, rotating the implant actuation shaft 334 causes it to advance longitudinally. For example, the threaded portion 336 engages a threaded portion 246 of a disconnect mount 236 in a screw-like manner. Rotating the implant actuation shaft 334 when the threaded portions 336, 246 are engaged causes the shaft 334 to advance proximally or distally, depending upon the direction of shaft rotation. When the threads are disengaged, the actuation shaft 334 can slide with respect to the implant 100.

The illustrated embodiment can provide anywhere in the range of 0%-100% of the collapse of the implant 100 by axially sliding a implant actuation shaft 334. In some embodiments, the implant actuation shaft 334 causes 25%, 30%, 40%, 50%, 60%, 70%, 75%, 80%, 90%, or 95% of the collapse or expansion of the implant 100, and can lock the implant in a partially-expanded or partially-reduced state. This provides the advantage of allowing the clinician to verify proper position and orientation of the implant 100 in small steps as the implant 100 is deployed within the patient's body.

Expansion of the implant 100 occurs while the threaded portion 336 of the implant actuation shaft 334 is engaged with the threaded portion 246 the disconnect mount 236. While the threaded portion 336 of the implant actuation shaft 334 is engaged with the threaded portion 246 the disconnect mount 236, the implant actuation shaft 334 is essentially locked in place unless sufficient torque is provided to rotate the two threaded portions 336 and 246 with respect to one another. This allows the implant 100 to be held or maintained in a fully or partially radially-reduced configuration.

While the flex fingers 238 hold the proximal end 104 of the implant 100 with concentric tensile force, an implant actuation shaft 334 extends through the implant 100 and pushes distally against the distal end 102 of the implant 100. As described above, the implant 100 can be made self-expanding, so that when the distal pushing force exerted by the implant actuation shaft 334 or the concentric proximal pulling (or holding) force applied by the flex fingers 238 is removed or reduced the implant 100 automatically radially expands to a predetermined size and shape. The implant 100 can be maintained in its reduced diameter configuration by holding the proximal end 104 of the implant 100 with the flex fingers 238 and pushing against the distal end 102 of the implant 100 with the implant actuation shaft 334. In this configuration, relative movement between the inner implant actuation shaft 334 and the concentric, outer flex fingers 238 controls implant 100 expansion and collapse.

In some embodiments, the flex fingers 238 are biased to extend either radially inwardly or radially outwardly. In embodiments where the flex fingers 238 are biased to extend radially inwardly, the flex fingers 238 engage a disconnect mount interface 180 to lock an implant 100 to the implant delivery system 50 when a structure prevents the flex fingers 238 from extending radially inwardly.

In one embodiment, as illustrated in FIGS. 21A-21C, the flex fingers 238 may be held in place with a disconnect mount interface 180 of the implant 100 by the presence of an implant actuation shaft 334 which extends through the implant 100 and prevents the flex fingers 238 from extending radially inwardly. When the implant actuation shaft 334 is withdrawn proximally toward the catheter system 300 past the disconnect mount 236, the open space created by the removal of the implant actuation shaft 334 leaves room for the flex fingers 238 to extend radially inwardly under its bias. This radial movement of the flex fingers 238 releases the disconnect mount 236 from the disconnect mount interface 180, thereby releasing the implant 100 from the implant delivery system 50.

In embodiments where the flex fingers 238 are biased to extend radially outwardly, the flex fingers 238 engage a disconnect mount interface 180 to lock an implant 100 to the implant delivery system 50 in its natural state. When a structure or a load causes the flex fingers 238 to extend radially inwardly the radial movement of the flex fingers 238 releases the disconnect mount 236 from the disconnect mount interface 180, thereby releasing the implant 100 from the implant delivery system 50 with significantly reduced or non-existent bending bias and rotational bias.

In some embodiments of an implant delivery system 50, markers 204 (not illustrated) may be placed in locations visible by fluoroscopic or other means known in the art of visualizing the manipulation or implantation of devices within a body. The markers 204, which can be radiopaque in nature, can be placed on any surfaces to assist in deployment or recapture of an implant 100, as is described above for the embodiment of a marker 360 as shown in FIG. 14, which advantageously assists in locating the position of a distal end 344 of an axially moveable core 342.

In various embodiments, a marker 204 comprises a radiopaque band, dot, coating, or material that is attached to a disconnect mount 236, a distal end 104 of an implant 100, and a portion of an implant actuation shaft 334. Marker 204 preferably is made from a material readily identified after insertion into a patient's body by using visualization techniques that are well known to those of skill in the art. In one embodiment, the marker 204 is made from gold, or tungsten, or any such suitable material, as is well known to those of skill in the art. In another embodiment, marker 204 is welded, soldered, or glued onto a structure for marking. In one embodiment, the use of markers 204 segments is useful to discern the radial orientation of the implant 100 within the body.

Referring once again to FIGS. 21A-21C, flex fingers 238 can be biased to extend radially outwardly or inwardly, as discussed above. In one embodiment, the flex fingers 238 are biased outwardly. The flex fingers 238 can also include a proximal inclined surface 242 at the transition from the flex finger 238 to the protruding portion 240. As illustrated, the embodied disconnect mount interface 180 uses a finger interface 182 in the form of slots or windows in a wall of a proximal end 104 of the implant 100.

Referring to embodiments in FIG. 21B, after the implant 100 is deployed and radially expanded in a LAA 10 (not illustrated here), anchors 118 on the implant frame 101 secure the implant 100 within the LAA 10. As depicted in FIG. 21C, the implant actuation shaft 334 can be withdrawn proximally away from contact with the flex fingers 238, allowing the flex fingers 238 to deflect inwardly. When the flex fingers 238 are moved proximally with respect to the implant 100, such as when the catheter system 300 is withdrawn proximally away from the expanded implant 100 in the LAA 10, the inside edge of the disconnect mount interface 180 can press onto the proximal inclined surface 242 (not shown), which provides a radially inward force to the flex fingers 238.

The radially inward force causes the flex fingers 238 or at least a distal portion of the flex fingers 238 to move radially inwardly. Once the flex fingers 238 are sufficiently radially deflected, the implant 100 is disconnected from the delivery system 50 without imparting any or any substantial moment arms or bending bias with respect to the implant 100. As depicted in FIG. 21C, once the implant 100 is detached, the flex fingers 238 will bias toward their natural state (inward bias is illustrated in solid lines and outward bias is illustrated in dotted lines).

In another embodiment illustrated in FIGS. 21A-21C, the flex fingers 238 are biased inwardly. Referring to embodiments in FIG. 21B, after the implant 100 is deployed and radially expanded in a LAA 10 (not illustrated here), anchors 118 on the implant frame 101 secure the implant 100 within the LAA 10. As depicted in FIG. 21C, the implant actuation shaft 334 can be withdrawn proximally away from contact with the flex fingers 238, allowing the flex fingers 238 to deflect inwardly in their natural state. Once the flex fingers 238 are sufficiently radially deflected, the implant 100 is disconnected from the delivery system 50 without imparting any moment aims or bending bias with respect to the implant 100. As depicted in FIG. 21C, once the implant 100 is detached, the flex fingers 238 will bias toward their natural state (inward bias is illustrated in solid lines and outward bias is illustrated in dotted lines). When the flex fingers 238 are biased inwardly, the implant actuation shaft 334 can be slideably engaged under the flex fingers 238 in order to deflect the flex fingers 238 outwardly.

As illustrated in FIGS. 21A-C, some embodiments include a flexible sock 392 positioned between the catheter body 302 and the disconnect mount 236. The sock 392 is discussed in greater detail below. In some embodiments, a catheter body 302 may be directly mounted to a disconnect mount 236.

In the illustrated embodiments described herein, an implant deployment system generally includes an implant coupled to a catheter with a release mechanism. The system also generally includes a mechanism to expand or contract the diameter of the implant. Although many of the embodiments describe the release mechanism coupled to the distal end of the catheter and the proximal end of the implant, it should be well understood by those of skill in the art that in other embodiments, the release mechanism is coupled to the distal end of the implant.

In addition, when the release mechanism is coupled to the proximal end of the implant, the implant is expanded by either moving the distal end of the implant proximally, by moving the proximal end of the implant distally, or by moving both ends towards the center of the implant. In many cases, the proximal end of the implant is held in place with respect to the patient's LAA and the distal end of the implant is allowed to move proximally under the self-expanding forces of the implant. However, in some situations, for example when treating patients that have a very short LAA, it may be desirable to perform a different procedure. For example, in such situations the clinician may desire to hold the distal end of the implant in place with respect to the patient's LAA while moving the proximal end of the implant distally; otherwise, the proximal end of the implant could wind up positioned within the patient's left atrium.

In some embodiments, the implant is expanded "in a distal direction" as just described by coupling the release mechanism to the distal end of the implant and then releasing tension from the implant's proximal end. Once the implant is radially expanded, the implant is released and the catheter is removed. For example, in one embodiment, the catheter and/or release mechanism extends through the implant's proximal end and its body to contact a portion near the distal end of the implant from within the implant.

The term "in a distal direction" refers to the steps of keeping the distal end of the implant in a relatively, substantially fixed position with respect to the deployment site while advancing the proximal end of the implant distally. Similarly, the term "in a proximal direction" refers to the steps of holding the proximal end of the implant in a relatively, substantially fixed position with respect to the deployment site while advancing the distal end of the implant proximally.

Therefore, the deployment systems can be configured to deploy in a proximal or a distal direction (or both). In addition, for any deployment direction configuration, the deployment systems can be further configured such that the release mechanism couples to either the proximal or distal end of the implant.

Figure 21D:
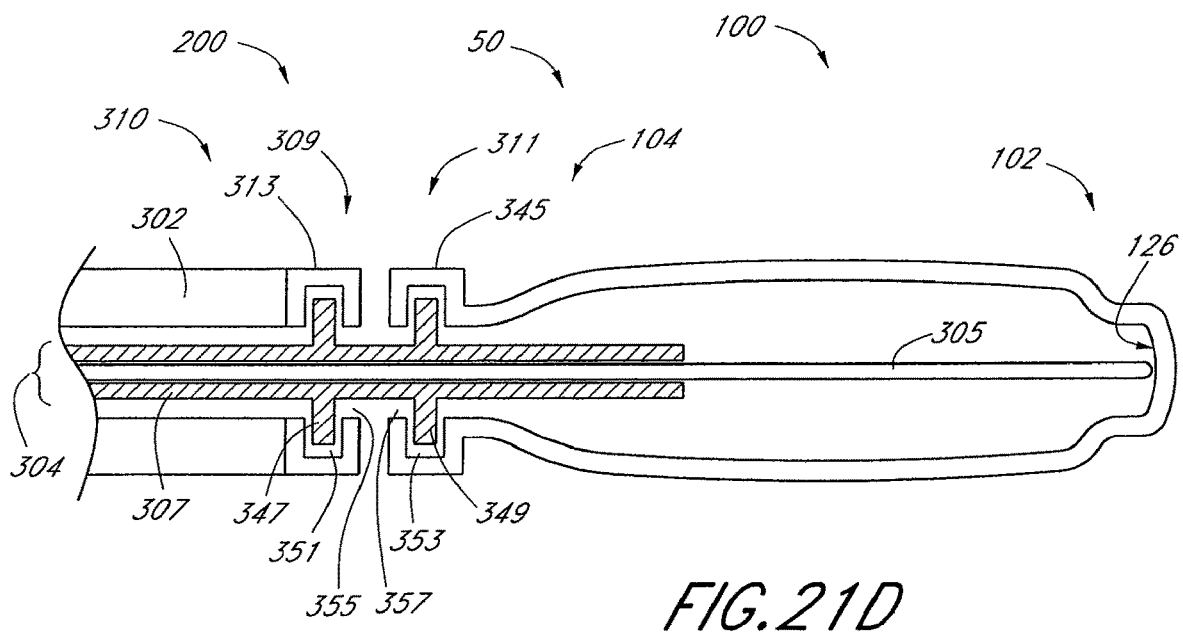
FIGS. 21D-E are cross-sectional views of another embodiment of an implant release mechanism.
Figure 21E:
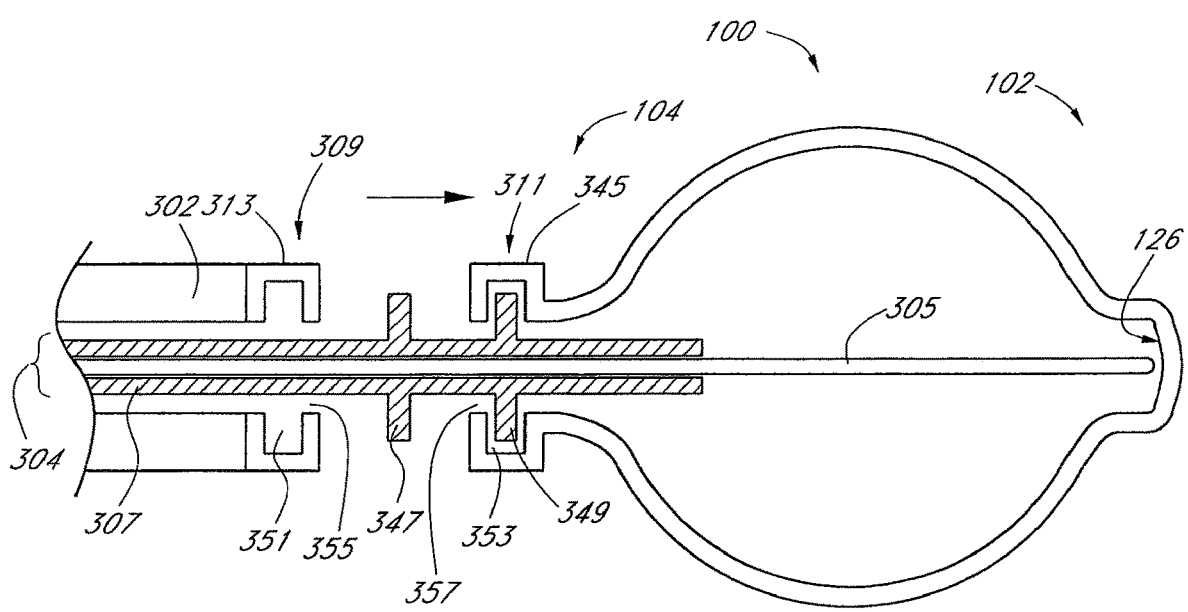

Referring to FIGS. 21D and 21E, in one embodiment the deployment system 50 is configured to deploy the implant 100 in a distal direction, and the release mechanism 200 is coupled to the proximal end 104 of the implant 100. A shaft, such as an axially moveable core 304, extends through the implant 100 and contacts the distal end 102 of the implant 100. The core 304 includes an inner core 305 and an outer core 307, which are coaxially aligned and can be longitudinally moved with respect to each other.

The outer core 307 includes two longitudinally spaced locking mechanisms. The first locking mechanism 309 is configured to engage and secure the outer core 307 to a mating portion 313 of the distal end 310 of the catheter 302. The second locking mechanism 311 is configured to engage and secure the outer core 307 to a mating portion 345 of the implant 100. In one embodiment, the locking mechanisms 309 and 311 include two radially offset cams 347 and 349 configured to engage mating surface slots 351 and 353, respectively, extending annularly within corresponding catheter mating portion 313 and implant mating portion 345, respectively.

Initially the cams 347 and 349 of the outer core 307 engage and are locked within both the catheter mating portion 313 and implant mating portion 345, respectively. In this configuration, the catheter 302, outer core 307, and implant 100 are fixed with respect to each other, and can be advanced together through a deployment sheath, such as a transseptal sheath (not illustrated here) or other retractable sheath.

The inner core 305 is extended to contact and push against the distal end 102 of the implant 100. Pushing on the distal surface 126 at the distal end 102 with the inner core 305 while holding the proximal end 104 in tension with the outer core 307 maintains the implant 100 in a reduced-diameter configuration. The diameter-reduced implant 100 is advanced through the patient's vasculature to a desired deployment site. At the deployment site, the implant's 100 distal end 102 is positioned under visualization at a desired location.

The outer core 307 is rotated with respect to the catheter 302 to cause the catheter cam 347 to align with an exit slot 355 in the catheter mating portion 313. Because the catheter cam 347 and implant cam 349 are offset from one another, alignment of the first cam 347 with the catheter mating portion's 313 exit slot 355 does not cause the second cam 349 to be aligned with the implant mating portion's 345 exit slot 357. For example, in some embodiments, the cams 347 and 349 are offset by about 15, 45, or 90 degrees from each other.

The outer core 307 is then advanced distally with respect to the catheter 302. The outer core 307 is now axially decoupled from the catheter 302, but still coupled to the proximal end of the implant 100 via the second cam 349-mating portion 345 engagement. As the outer core 307 is moved distally, the proximal end 104 of the implant 100 is also advanced distally. This causes the implant 100 to expand in a distal direction, e.g., while maintaining the distal end 102 of the implant 100 in a substantially fixed position with respect to the deployment site (e.g., the LAA 10, not pictured here). In addition, as the outer core 307 is advanced distally with respect to the catheter 302, the outer core 307 is also advanced distally with respect to the inner core 305. This prevents distal advancement of the outer core 307 from pushing the implant 100 deeper into the LAA 10, or out of the desired deployment location.

When the implant 100 is fully expanded the outer core 307 is disengaged, or decoupled from the implant 100 by rotating the second cam 349 with respect to the implant 100. When the implant cam 349, or a cam tab, is aligned with an exit slot 357 in the implant mating portion 345, the outer core 307 can be retracted proximally with respect to the implant 100 without substantially affecting the implant's 100 deployment location or orientation. At this point the outer core 307 is decoupled from both the catheter 302 and implant 100, and may withdrawn with the catheter 302 and inner core 305 from the patient's vasculature.

In some embodiments the inner 305 and outer shafts 307 are made from flexible hypotube. In other embodiments, the locking mechanisms 309 and 311 are sometimes referred to as an implant key or tip or as a catheter key or tip. The mating portion 313 of the catheter 302 is sometimes referred to as the locking tip.

Figure 21F:
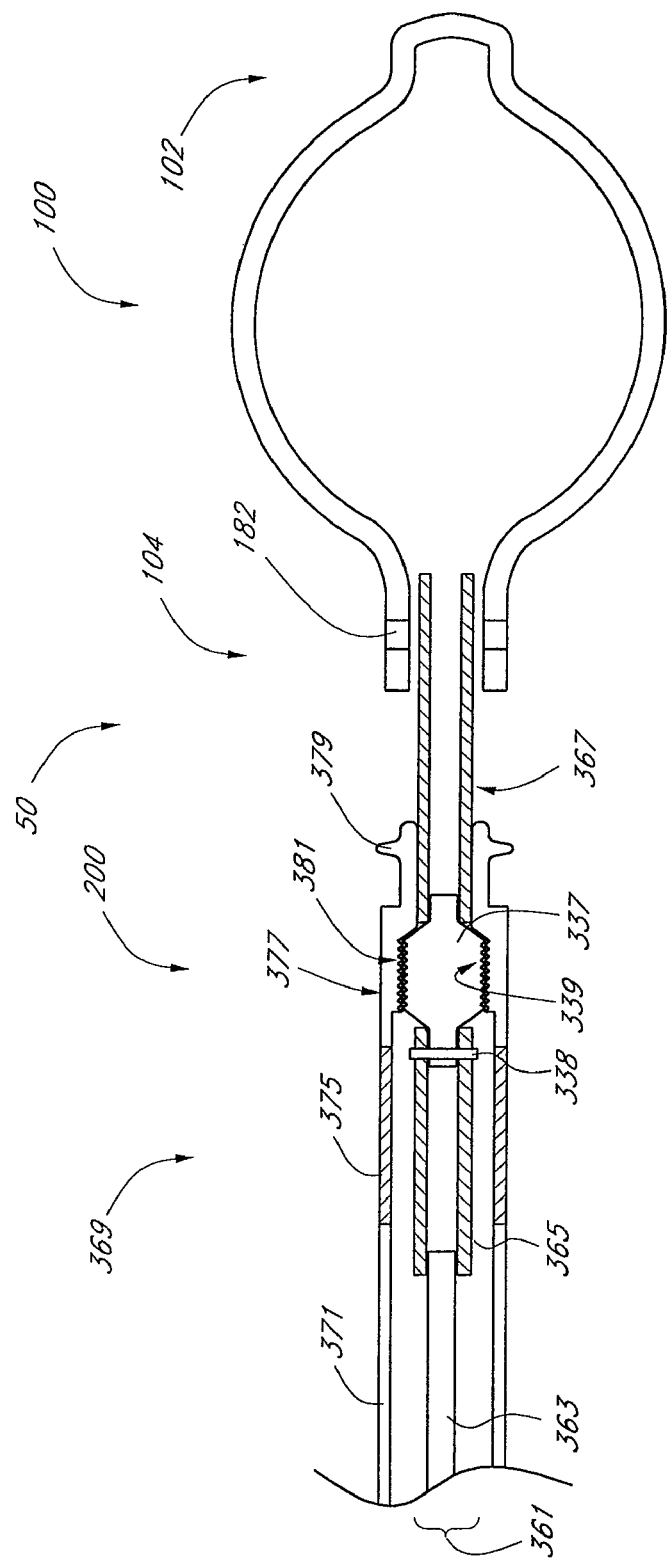
FIG. 21F is a cross-section view of another embodiment of an implant release mechanism.

FIG. 21F illustrates another flexible implant delivery system in accordance with yet another embodiment of the invention. The delivery system 50 includes an implantable device 100 and a release mechanism 200. The configuration described with respect to FIG. 21F can be utilized and/or incorporated into any of the other embodiments described herein.

The implantable device 100 is similar to all of the other implantable devices described herein. The implantable device 100 is configured to expand from a radially reduced configuration to a radially expanded configuration. For example, in some embodiments, the implantable device 100 is self expandable. The implantable device 100 includes a plurality of struts that extend from the implant's proximal end 104 to its distal end 102. A window, notch, hole, or port, in the implant's proximal end 104 is configured to releasably engage the release mechanism 200.

The release mechanism 200 includes a drive shaft 363, which is coupled at its distal end to the proximal end of a flexible recapture shaft 365. In one embodiment, the drive shaft 363 is made from 0.025" diameter tubing. In another embodiment, the flexible recapture shaft 365 is made from 0.042" outside diameter by 0.027" inside diameter tubing. The distal end of the flexible recapture shaft 365 is coupled to a threaded adapter 337. In one embodiment, the recapture shaft 365 and adapter 337 are coupled with a cross pin 338. For example, a 0.025" cross pin 338 is sometimes used. The distal end of the threaded adapter 337 is coupled to a second flexible recapture shaft 367. In some embodiments, a single flexible recapture shaft 365 is used, which extends through the threaded adapter 337. The threaded adapter 337 includes a threaded portion 339 with threads along at least a portion of its outside surface.

The driver 363, flexible recapture shafts 365 and 367, and threaded adapter 337 are disposed within an outer shaft assembly 369. The outer shaft assembly 369 includes a braided shaft 371 that is coupled at its distal end to a flexible torque shaft 375. In one embodiment, the braided shaft 371 is the braided sock 392 described above. In another embodiment, the braided shaft 371 has dimensions of 0.084" OD.times.0.055" ID. In one embodiment, the flexible torque shaft 375 is the braided sock 392 described above. In one embodiment, the flexible torque shaft 375 has dimension of 0.083" OD.times.0.072" ID. The distal end of the flexible torque shaft 375 is coupled to a push screw disconnect 377, which in some embodiments is the disconnect mount 236 described in greater detail herein.

The push screw disconnect 377 has distally extending fingers 379 that have a larger diameter at their distal ends. The push screw disconnect 377 also includes a threaded inside surface 381 configured to engage the threaded portion 339 of the threaded adapter 337. The distal ends of the fingers 379 are configured to engage the window 182 in the implant 100 and to hold the implant 100 with respect to the braided shaft 371 and flexible torque shaft 375. However, in one embodiment the fingers 379 are biased to flex inward to release the implant 100. Therefore, an inner core assembly 361, comprising the driver 363, flexible recapture shafts 365 and 367, and threaded adapter 337 are used to interfere with inward movement of the fingers 379, and to hold the fingers 379 outward such that they continue to radially, coaxially engage the implant 100.

To release the implant 100, the inner core assembly 361 is rotated with respect to the push screw disconnect 377. The core assembly 361 is rotated until it no longer engages the push screw disconnect 377, at which point it is retracted proximally with respect to the outer shaft assembly 369. Once the inner core assembly 361 is retracted, the fingers 379 move radially and concentrically inward to their biased position, thereby releasing the implant 100. The implant 100 is released by removing the concentric radial force provided by the outer core assembly 369. Releasing the implant 100 in this manner does not cause the implant 100 to substantially jump, move, or otherwise change its orientation with respect to the delivery system 50.

3. Deployment Catheter and Deployment Handle

Referring again to FIG. 2, there is illustrated a block diagram representing an implant delivery system 50 suitable for use with any and all of the embodiments discussed herein. The implant delivery system 50 includes an implant 100, an implant release and recapture mechanism 200, a catheter system 300 and a deployment handle 400. FIG. 2A illustrates one embodiment of an implant delivery system 50 comprising particular examples of an implant 100, an implant release and recapture mechanism 200, a catheter system 300 and a deployment handle 400.

Referring again to FIG. 11, there is schematically illustrated a further embodiment of the present invention. An adjustable implant delivery system 50 comprises generally a catheter 302 for placing a detachable implant 100 within a body cavity or lumen, as has been discussed. The catheter 302 comprises an elongate flexible tubular body 306, extending between a proximal end 308 and a distal end 310. The catheter is shown in highly schematic form, for the purpose of illustrating the functional aspects thereof. The catheter body will have a sufficient length and diameter to permit percutaneous entry into the vascular system, and transluminal advancement through the vascular system to the desired deployment site. For example, in an embodiment intended for access at the femoral vein and deployment within the left atrial appendage, the catheter 302 will have a length within the range of from about 50 cm to about 150 cm, and a diameter of generally no more than about 15 French. Further dimensions and physical characteristics of catheters for navigation to particular sites within the body are well understood in the art and will not be further described herein.

The tubular body 306 is further provided with a handle 402 generally on the proximal end 308 of the catheter 302. The handle 402 permits manipulation of the various aspects of the implant delivery system 50, as will be discussed below. Handle 402 may be manufactured in any of a variety of ways, typically by injection molding or otherwise forming a handpiece for single-hand operation, using materials and construction techniques well known in the medical device arts.

In the embodiment illustrated in FIG. 14, or any other of the deployment and/or removal catheters described herein, the distal end 310 of the tubular body 306 may be provided with a zone or point of enhanced lateral flexibility (indicated by the sectional lines on the tube 306 at the distal end 310). This may be desirable in order allow the implant to seat in the optimal orientation within the left atrial appendage 10, and not be restrained by a lack of flexibility in the tubular body 306. This may be accomplished in any of a variety of ways, such as providing the distal most one or two or three centimeters or more of the tubular body 306 with a spring coil configuration. In this manner, the distal end of the tubular body 306 will be sufficiently flexible to allow the implant 100 to properly seat within the LAA 10. This distal flex zone on the tubular body 306 may be provided in any of a variety of ways, such as by cutting a spiral slot in the distal end of the tubular body 306 using laser cutting or other cutting techniques. The components within the tubular body 306 such as torque rod 340 may similarly be provided with a zone of enhanced flexibility in the distal region of the tubular body 306.

FIG. 22 (which is similar to FIG. 2A) illustrates one embodiment of an implant delivery system 50 comprising an operably connected implant 100, an implant release and recapture mechanism 200, a catheter system 300 and a deployment handle 400. As shown in FIG. 22, the embodied catheter system 300 comprises a peel-away sheath 314, a recapture sheath 522, a deployment catheter 302, a loading collar 323, a multi-lumen shaft 326, and an axially moveable core 304, each described further below. The system 50 may also include a transseptal sheath 520 (not illustrated here) that is substantially coaxial and external to the other catheters. In some embodiments, the transseptal sheath may be one of the other catheters. The deployment handle 400 comprises a handle 402, a control knob 408, a release knob 410, a proximal injection port 412 and a distal injection port 414. Injection ports 546, 548, as shown in FIG. 22, preferably are provided in the delivery system 50 to allow contrast injection proximally and distally of the implant 100 to facilitate in-vivo assessment of the positioning and seal quality of the implant 100.

Referring again to FIG. 22, illustrated is an embodiment of an implant delivery system 50. When an embodiment of the delivery system 50 is assembled, a recapture sheath 522 is loaded over the deployment catheter 302, distal to the handle 402. The recapture sheath 522 is designed to allow recapture of the implant 100 prior to its detachment or final release, such as described with respect to retrieval catheter 502 above. Recapture petals or flares 510 may be provided on the distal end 506 of the recapture sheath 522 to cover the anchors 118 of the implant 100 during retrieval into the transseptal sheath 520, as described above with respect to FIGS. 15C-15E, and further below. A Touhy-Borst adapter or valve 530 may be attached to the proximal end 524 of the recapture sheath 522. The recapture sheath 522 comprises a radiopaque marker 528 on its distal end 526 near the recapture flares 510. The recapture sheath 522 comprises a recapture sheath injection port 529 for delivering fluid proximal the implant 100.

An embodiment of the peel-away sheath 314 is provided over a portion of the recapture sheath 522, between Touhy-Borst valve 530 and recapture flares 510. The peel-away sheath 314 is used to introduce a catheter 302 into a transseptal sheath 520 (not illustrated). As shown in FIG. 22, an embodiment of the peel-away sheath 314 comprises a locking collar 315, a peel-away section 316, and a reinforced section 317. The locking collar can be unlocked relative to peel-away section 316, and may include a threaded hub 318 that releasably engages tabs 319 of the peel-away section 316.

An embodiment of the loading collar 323 is located over a portion of the peel-away sheath 314 and a portion of the recapture sheath 522 with its proximal end being located over the peel-away sheath 314 at its distal end loaded over recapture sheath 522. The loading collar 323 can accommodate loading a collapsed implant 100 into the peel-away sheath 314 as described below. As shown in FIG. 17, an embodiment of the loading collar 323 comprises a first end portion 324 adapted to receive and extend over a collapsed implant 100, and a second end portion 325 configured to guide the collapsed implant 100 into the peel-away sheath 314. The loading collar 323 may be made of stainless steel.

In order to assemble an embodiment of the delivery system 50, the axially movable core 304 and control line 312 are fed into the multi-lumen shaft 326 of the deployment catheter 302. The multi-lumen shaft 326 is then coupled with components of the deployment handle 400 and the injection port components 412, 414. The peel-away sheath 314 and the loading collar 323 are slid onto the recapture sheath 522, and the recapture sheath 522 is slid onto the deployment catheter 302. The implant 100 is then loaded on an end of the axially movable core 304 and coupled with the control line 312. In one embodiment, the implant 100 is loaded on an end of the axially movable core 304 by screwing the axially movable core 304 into the threaded portion 246 of a disconnect mount 236 (not illustrated here). The control knob 408 and outer casing of the deployment handle 400 are then coupled with the system.

In an embodiment of the deployment catheter system 300, a catheter 302 is used in connection with a transseptal sheath 520 (not illustrated here, but see FIG. 25) to advance the implant 100 for deployment in a patient. The transseptal sheath 520 is a tubular device that in one embodiment can be advanced over a guidewire (not shown) for accessing the LAA 10 of a patient's heart 5. In some embodiments the transseptal sheath 520 may also serve as one of the other disclosed catheters described herein. Transseptal sheath 520 in some embodiments has a permanent bend or a controllable bend. A hemostasis valve (not illustrated) is provided at the proximal end of transseptal sheath. A fluid injection port is also provided at the proximal end to delivery fluid such as contrast media through the transseptal sheath. Systems and methods for implanting the device 100 in the LAA 10 are described further below.

One embodiment of a multi-lumen shaft 326 may comprise a four-lumen shaft as illustrated in FIG. 22A. The multi-lumen shaft 326 comprises a core lumen 328 for holding an axially moveable core 304, a control line lumen 330 and two proximal injection lumens 332 in communication with proximal injection port 412. In some embodiments, the axially moveable core 304 is the implant activation shaft 334, discussed in greater detail above.

An axially moveable core 304 preferably extends from the deployment handle 400 through the core lumen 328 of the catheter 302 and couples the implant 100 of the delivery system 50. A control line 312 (referred to previously as a pull wire 312) preferably extends through the control line lumen 330 and preferably couples a proximal hub 104 of the implant 100 to the deployment handle control knob 408, allowing for implant 100 expansion and collapse. The control line 312 preferably extends around a portion of the axially movable core 304 near the proximal hub 104 of the implant 100, and is coupled to the implant 100 by crosspin 146, as described above.

Referring to FIG. 23, one embodiment of the catheter system 300 preferably comprises a flexible catheter section 362 at its distal end, which in some embodiments is a spiral cut tubular section housed in a polymer sleeve 366. The flexible catheter section 362 may be coupled to a distal end of a multi-lumen shaft 326.

As shown in FIGS. 24 and 24A, one embodiment of the axially moveable core 304 preferably includes a hollow proximal shaft 368 and a hollow distal shaft 370 with a flexible hollow core section 372 therebetween, all co-axially aligned and connected. In one embodiment, the proximal end of the distal shaft 370 is attached to the distal end of the flexible core section 372, and the proximal end of the flexible core section 372 is attached to the distal end of the proximal shaft 368. In some embodiments, the flexible core section 372 has a spring coil section 374 housed in a polymer sleeve 376, the spring coil section 374 preferably coupled with the shafts 368 and 370 on first and second ends 378 and 380, respectively. In another embodiment an injection tube 373 with a lumen is provided, through which contrast fluid may be ejected out of the distal end of the implant actuation shaft 334 and into the implant 100. This is useful in assessing implant seal against the ostium or inside wall of the left atrial appendage. The injection tube 373 has been prototyped in low durometer (flexible) PEBAX and provides a soft segment transition over the distal-most 10 cm of the delivery catheter 302 or within a flexible core section 372. The injection tube 373 may be connected to other tubes such as a lock tube 234 (as discussed relating to FIGS. 17-20) but is not used to torque or apply rotational forces to the tube.

The axially moveable core 304 preferably is disposed within the deployment catheter 302 such that the flexible core section 372 may be linearly co-located with the flexible catheter section 362 at a distal portion 382 of the catheter system 300 during appropriate times during a procedure, as shown in FIG. 23. When the flexible core section 372 is aligned and linearly co-located with the flexible catheter section 362, the sections preferably cooperate to form a delivery system flexible segment 384. As shown in FIGS. 22 and 23, the delivery system flexible segment 384 preferably is located toward a distal portion 382 of the catheter system 300.

In one embodiment, shown in FIG. 24, the distal shaft 370, flexible core section 372, and proximal shaft 368 are attached by welding. Small windows 386 may be provided to allow welding materials to flow between the shafts 564, 576 and 578 and provide stronger bonding therebetween. In another embodiment, solder, glue, or press-fitting is used to attach shafts 564, 576, and 578 to one another, as is well known to those of skill in the art. In another embodiment, the shafts 564, 576 and 578 are formed from a single tube, for example, a laser-cut tube. In other embodiments, more than one tube may be used to form each of the shafts 564, 576 and 578. For example, FIG. 24 illustrates proximal shaft 368 comprising two tubes connected by welding such as described above.

Referring again to FIG. 24A, distal contrast media preferably can be injected through a lumen 388 in the shafts 576 and 578 for determining the placement of the implant 100. This lumen 388 may be in fluid communication with distal injection port 414, shown in FIG. 22. The distal shaft 370 preferably comprises a mating surface 390 and a radiopaque marker 360, such as described above. In one embodiment, the mating surface 390 is a threaded surface. The distal shaft 370 preferably is releasably coupled to the implant 100, such as described above.

Figures 25, 25A:
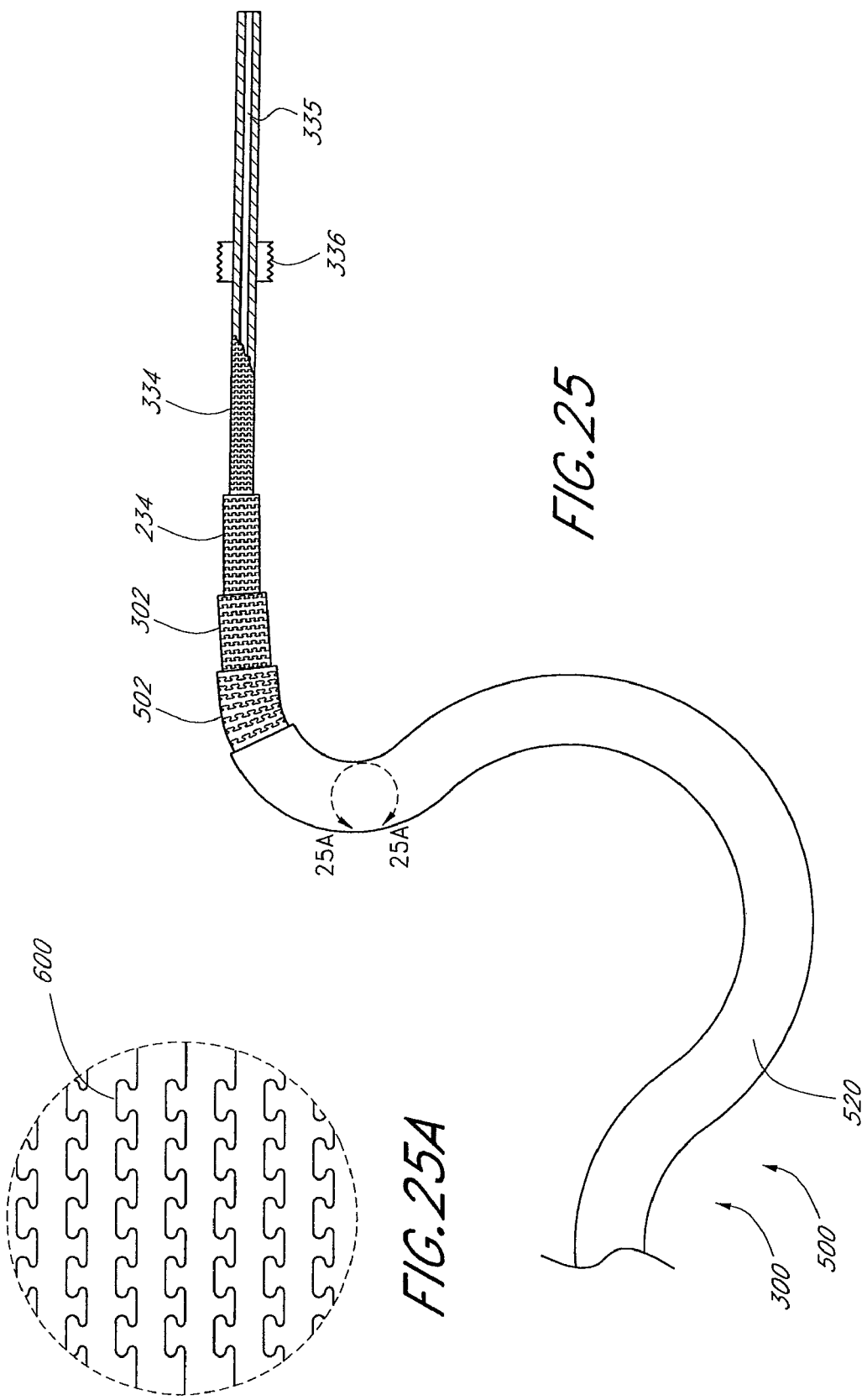
FIG. 25 is a schematic of an embodiment of a flexible catheter system constructed in accordance with one embodiment of the present invention.
FIG. 25A is a close up of an embodiment of a puzzle lock profile constructed in accordance with one embodiment of the present invention.

FIG. 25 illustrates an embodiment of a puzzle lock profile 600 that may be used with any of the embodiments of the implant delivery system 50 described herein in order to increase flexibility. As discussed above, some of the embodiments deliver an implant 100 to the LAA 10 in an orientation and under a loading condition that approximates the final released state of the implant 100. This reduces bias and moment arms that can cause the implant 100 to deform, move, jump, or change orientation when the implant 100 is released from the implant delivery system 50. Component rigidity and off-axis loading can contribute to these undesirable effects. An elongate tube having a strong, flexible, cut wall pattern such as the puzzle lock profile 600 can improve system flexibility and reduce unwanted loading conditions.

FIGS. 25A-25C illustrate a puzzle lock profile 600 in accordance with an embodiment. The puzzle lock profile 600 can be used to create highly flexible materials such as tubing with push, pull, and torque capabilities. The puzzle lock profile 600 can be used to transmit axial loads and rotational torque loads while minimizing bending loads through its flexibility. As illustrated, one embodiment of the puzzle lock profile 600 comprises a cut through a tube or a layer of material using a laser or some other similar manufacturing means known in the art. Referring to FIG. 25B, illustrated is a tube 605 with a longitudinal axis 610, a diametric axis 620, and a puzzle lock profile 600 cut into it. The tube 605 can be any tube or shaft discussed herein. The longitudinal axis 610 runs along the general axis in the lumen of a tube or through the center of a solid tube when that tube is straight. The diametric axis 620 lies in a plane that is perpendicular to the longitudinal axis 610 and runs along a diameter of the tube 605.

In some embodiments, a cut 635 may start at either the proximal or distal end of the tube 605. In other embodiments, a cut 635 may start at an offset length 630 from an end of a tube 605. The offset 630 may provide structural support to the ends of the tube or may represent an uncut tubing length prior to a puzzle cut region in a tube. A corresponding offset 630 may exist at the other end of the tube 605, and in some embodiments there may be a plurality of regions in a tube 605, alternating between puzzle lock profile 600 regions and uncut tubing or offset 630 regions.

Referring to FIG. 25C, a puzzle lock profile 600 is presented in close up of a tube 605. FIG. 25C may also be considered a view of a tube 605 that has been sliced longitudinally and spread into a flat planar surface. In this view, a cut 635 can have a cut axis 640 which runs along the length of the cut 635. As illustrated, the weaving cut 635 follows a repeating pattern that is symmetric around the cut axis 640. In one embodiment a tube 605 has a number of generally parallel cut axes 640, 650, 660, and 670. Additional cut axes may continue along a length of the tube 605 (not illustrated). In one embodiment, cut axes 640, 650, 660, and 670 may be parts of a single continuous cut that traverses external surface of a tube 605, similar to a spiral. In another embodiment, cut axis 640 and cut axis 650 may be two parallel cut axes that are offset from each other, creating two interlaced parallel spiral cuts along the tube 605. In one embodiment, the two spiral cuts start 180 degrees from each other in a plane perpendicular to the longitudinal axis 610 of the tube 605 to create two symmetric spiral cuts and two helical tube surfaces. The two starting points may be located on the diametric axis 620 at intersection points with the external surface of the tube 605. In this embodiment, a first cut 635 moves along a cut axis 640 which is contiguous with cut axis 660, and a second cut 636 is contiguous with cut 670. In other embodiments, there may be two, three, four, or a plurality of cuts, such as cut 635, cut 636, cut 637 and cut 638, that create parallel spiral cuts along the tube 605 with cut axes 640, 650, 660, and 670, respectively, which can create either symmetric or non-symmetric spiral cuts and helical tube surfaces along the tube 605.

Referring to FIG. 25C, illustrated is an embodiment of a puzzle lock profile 600 with a single cut 635 that extends along cut axes 640, 650, 660, and 670 each time the cut 635 wraps around the outer circumference of a tube 605. The cut 635 extends generally around the circumference of the tube 605 and follows a continuous repeating pattern which is inclined at a slight angle .alpha. from a diametric axis 620 to a longitudinal axis 610 of the tube 605. Each of the cut axes 640, 650, 660, and 670 are parallel to each other with a planar cut axis that can be drawn along the general direction of the cut 635. In one embodiment, a cut 635 is oriented to follow a cut axis 640 with an angle .alpha. of zero degrees, the cut axis 640 being parallel to the diametric axis 620 and perpendicular to the longitudinal axis 610 of the tube 605, resulting in a cut that would traverse the circumference of the tube 605 and return to the same location as its starting point, thereby creating a series of interlocked rings with multiple cuts. In another embodiment, angle .alpha. may be anywhere in a range of 0 to 90 degrees, where in some embodiments angle .alpha. may be about 1, 2, 3, 4, 5, 6, 7, 8, 9, 10, 15, 20, 25, 30, 35, 40, 45, 50, 60, 65, 70, 75, 80, 85, or 90 degrees. In the illustrated embodiment in FIG. 25C, angle .alpha. is in the range of about 5-7 degrees.

Along a given cut axis 640, the cut 635 may run along a pattern that alternates on either side of the cut axis 640 and that runs parallel to the cut axis 640 at a distance 642 and a distance 643. In some embodiments, distance 642 equals distance 643. As a cut 635 alternates on either side of the cut axis 640 the pattern cuts a length 646 along a cut axis 640 when the cut 635 is on the distance 643 from the cut axis 640, and a length 647 along a cut axis 640 when the cut 635 is on the distance 642 from the cut axis 640. In some embodiments, length 646 equals length 647. As a cut 635 runs along a pattern at a distance 643, it enters a bend toward the cut axis 640. The bend has a radius 644 which is on the order of half of the distance 643. As the cut 635 approaches the cut axis 640 the bend reaches an inflection point and changes direction, creating a bend with a radius 645 which is on the order of half of the distance 642. In some embodiments, radius 644 equals radius 645. These bends create a set of interlocking projections that keep the tube engaged to transmit axial loads and rotational loads, about the longitudinal axis 610 while providing flexibility in the tube 605 to reduce bending moments.

The dimensions of a cut 635 with respect to a cut axis 640 depends on the desired push, pull, and torque characteristics of a given tube 605, and may further depend on tube 605 thickness, diameter, length, and material. In some embodiments, the tube 605 is made of metal, stainless steel, hypodermic materials, nickel titanium, plastic, polymers, silver, or radiopaque visualization materials. Angles and lengths and various other dimensions depend on the number of parallel cuts that may be desired as well. Embodiments of the puzzle lock profile 600, as illustrated in FIGS. 25 and 25A-25C, may be used in the material of an implant actuation shaft 334, a lock tube 234, a catheter body 302, a retrieval catheter 502, a transeptal sheath 520, a catheter system 300, a retrieval catheter system 500, or any component of an implant delivery system 50, as discussed herein. The puzzle-interlocking features 338 illustrated provide super flexibility of the various tubes while maintaining push, pull and torque transmission capabilities. Any of the puzzle-interlocking profile 600 tubes can be covered with a thin silicone tubing to provide a seal over the interlocking portions of the tube to allow for transport of contrast or other fluids within the lumen of the tubes. In some embodiments, portions of tubes (such as a flexible core section 372 or a flexible segment 384 as illustrated in FIG. 24) which require greater flexibility can use the puzzle lock profile 600 which are attachable to other embodiments of the respective tube. In other embodiments, the entire tube or component can be constructed using a puzzle lock profile 600.

In one embodiment, a puzzle lock profile 600 is incorporated into an implant actuation shaft 334. Previous embodiments of implant actuation shafts 334 have been described in terms of an axial moveable core 304 and a torque rod 340, as discussed above relating to at least FIGS. 17-21. The implant actuation shaft 334 is generally a tubular structure for imparting a distal force on the distal end 102 of the implant 100. In various embodiments, the implant actuation shaft 334 can be a hypodermic or a metallic tube. In addition, the implant actuation shaft 334 can be cut (e.g., laser cut) to have a spiral or puzzle-lock wall profile 600. One embodiment of a puzzle lock profile 600 is shown in FIG. 25. A spiral cut has little resistance to bending, is capable of applying limited compression and can be torqued in one direction. The puzzle-lock profile 600 cut has these same properties but is also capable of applying tension and torque in both directions. The puzzle lock 338 is generally screwed in and out of the catheter system 300 in both clockwise and counter-clockwise directions. Since both cuts generally are not able to apply bending moment, they are both advantageously very flexible. Embodiments of puzzle-lock tubes are disclosed in U.S. Pat. No. 6,273,876, filed Nov. 3, 1998, which is incorporated by reference herein.

Referring back to FIGS. 21A-21C, there is illustrated an embodiment of a flexible sock 392, such as a metallic mesh sock 392 (e.g., made from nickel titanium, or NITINOL), which partially covers at least a portion of an implant actuation shaft 334 and a slide tube 394. The implant actuation shaft 334 works with the sock 392 to collapse the implant. As discussed above, the memory metal properties of the implant 100 cause its natural state to be open, or radially expanded to an expanded-diameter configuration. Distal force is applied to override the natural state and place the implant 100 in tension in order to reduce the implant 100 to its reduced-diameter configuration. A small moment arm associated or combined with the distal force can cause the delivery catheter 302 to bend. This in turn can cause the implant 100 to shift and change its spatial orientation, depending upon the amount of force and/or the amount the implant 100 is collapsed. A concentric, 360.degree. application of tension concentric to the compression force delivering implant actuation shaft 334 helps achieve non-biased expansion of the implant 100. The tension member in the form of a sock 392 avoids applying bending moment, as previously discussed. It also avoids applying compression. In order for the left atrial appendage (not illustrated here) to naturally assert its influence on the implant 100 and for the implant 100 to be properly seated within the left atrial appendage, once the tension has been released, it is advantageous if no additional expansion loads are transmitted from the delivery catheter 302 to the implant 100. If there were, the delivery catheter 302 could falsely bias the implant 100 into an exaggerated or over-expanded expanded state, which would not represent the final release conditions. In such cases the expansion force of the implant 100 could override the compression forces provided by the left atrial appendage.

The sock 392, which can be a braided, multi-stranded nickel titanium tube, is preferably used to help achieve concentric application of tension to the implant 100. Prototypes have shown tensile forces exceeding two times those used to collapse the implant 100; no bending resistance; and no compression load transfer over the first 50% of axial strain (e.g., the sock 392 flexibly collapses to a point, as illustrated in FIG. 21C). The sock 392 can provide tension forces to the proximal end 104 of the implant 100 via the disconnect flex fingers 238 described above. The sock 392 can be attached to the delivery catheter 302 and disconnect mount 236 using any method known to those of skill in the art, including adhesive, welds, bonds, mechanical links, pins, etc. In one embodiment, LOCTITE adhesive is used to bond the proximal end of the sock 392 to the distal end of the delivery catheter 302. In other embodiments, the sock 392 is trapped with a laser weld or swaged ring. The sock 392 can also be re-flowed directly into the delivery catheter 302 outer lumen or it can be an extension of a braid that can be provided in the delivery catheter 302. The ability of the sock 392 to "spring back," or return to its initial state without taking a permanent set helps maintain consistent expansion and collapse properties during the implant 100 deployment and recapture process. The super-elastic properties of NITINOL are well-suited for use as the sock 392. In addition, a stainless steel braid will take a set and create compression bias as well. In one embodiment, the sock 392 may use aspects of a puzzle lock profile 600 as described above.

In some embodiments, a slide tube 394 is provided inside the sock 392 and outside an implant actuation shaft 334. The slide tube 394 may be used to prevent the sock 392 from binding on a implant actuation shaft 334 or act as a stop in limiting axial motion of the implant actuation shaft 334. The slide tube 394 may slide freely with respect to the implant actuation shaft 334 or the collar 394 may be attached to the implant actuation shaft 334 in any number of ways know to the art. In one embodiment, the slide tube 394 may be an integral part of the implant actuation shaft 334. As shown in FIGS. 21A-21C, an embodiment of an implant delivery system 50 includes a slide tube 394. A handle (not illustrated here) provides proximal tension, a sock 392 necks down onto the slide tube 394 and pulls a proximal end 104 of an implant 100 away from its distal end 102. The distal end 102 is held "stationary" by an implant actuation shaft 334. As the sock 392 pulls the proximal end 104 proximally with respect to the distal end 102, the implant 100 is reduced in diameter. As the tension on the proximal end 104 is released the proximal end 104 moves distally towards the distal end 102, and the implant's diameter expands. A control on the handle controls tension on the proximal end 104.

B. Configurations and Methods of Use of an Implant Delivery System

Referring to FIG. 6, illustrated is an embodiment of an implant delivery system 50. The system and method allows for access and assessment of the LAA 10. In one embodiment, a guidewire (not shown) is used to access the superior vena cava through groin access. A transseptal sheath 520 is advanced over the guidewire and into the superior vena cava. The guidewire is removed and replaced with a transseptal needle (not shown). The transseptal sheath 520 preferably is retracted inferiorly so that a bend in the transseptal sheath directs the distal tip of the transseptal sheath toward the fossa ovalis. The needle is advanced to puncture the fossa ovalis. The transseptal sheath 520 is advanced to establish access to the LAA 10 and the needle is retracted. Further details or disclosure are provided above and in copending U.S. patent application Ser. No. 09/435,562 and U.S. Pat. No. 7,044,134, issued May 16, 2006, the entireties of which are hereby incorporated by reference.

After preparing a transseptal sheath 520 for LAA 10 access, the size of the neck diameter and morphology of the LAA 10 preferably is determined by advancing the transseptal sheath 520 to the distal portion of the LAA 10 and injecting contrast media to obtain an initial left atrial appendogram. The neck diameter preferably is measured approximately 5 mm in from the ostium of the LAA 10 at end diastole.

Referring to FIG. 22, illustrated is an embodiment of a system and method that allows for selection and preparation of a deployment system 50. A deployment system 50 preferably comprises an implant 100 of an appropriate size for placement in a patient. Initially, the implant 100 preferably is in an expanded configuration, with an implant release and recapture mechanism 200 engaging the implant 100, as described above. The recapture sheath 522 preferably is positioned so it covers and supports the flexible segment 384 of the delivery system 50, wherein the flexible catheter section 362 of deployment catheter 302 and flexible core section 372 of axially moveable core 304 are aligned. The Touhy-Borst valve 530 preferably is tightened over the deployment catheter 302 to prevent relative movement between recapture sheath 522 and deployment catheter 302. The loading collar 323 and peel-away sheath 314 preferably are positioned so they are at the base of the recapture flares 510, proximal thereto.

In one embodiment, the delivery system 50 is loaded by rotating the control knob 408 counterclockwise until the implant 100 is fully collapsed. Preferably, at least a portion of the control line 312 is coupled with the control knob 408 such that rotation of the control knob 408 retracts at least a portion of the control line 312. In an embodiment, the rotation of the control knob 408 is in the counterclockwise direction to retract at least a portion of the control line 312. Retraction of the control line 312 preferably places tension on the proximal hub 104 of the implant 100, because a portion of the control line 312 preferably is coupled with the proximal hub 104 by a pin 146. While the distal portion of the axially moveable core 304 applies a distal force to distal hub 108 of the implant 100, tension in the control line 312 preferably causes the proximal hub 104 of the implant 100 to move proximally relative the axially moveable core 304, thereby collapsing the implant 100.

In another embodiment, the delivery system 50 is loaded with an implant 100 connected to an implant release and recapture mechanism 200, which is connected to a catheter system 300, which is connected to a deployment handle 400. A disconnect mount interface 180 on the proximal end 104 of the implant 100 is connected to a disconnect mount 236 on a catheter system 300 which can provide releasable concentric loading to the implant 100 as described above. In one embodiment, the concentric loading is concentric tension. In one embodiment the concentric loading is provided by a disconnect mount interface 180 with a finger interface 182 which interacts with a flexible finger 238 on the disconnect mount 236. Embodiments of the finger interface 182 may be in the form of a protruding finger, an interlocking feature, a groove, a slot, a window, or other similar features for releasably holding a disconnect mount 236 flexible finger 238. In one embodiment the flexible finger 238 is engaged with the finger interface 182 and a lock tube 234 is slid into place to secure the engagement between the flexible finger 238 is engaged with the finger interface 182. In some embodiments, the lock tube 234 may be rotated to threadably engage with a catheter 302 to lock in place. In other embodiments no lock tube 234 is necessary.

An implant actuation shaft 334 may be extended distally through the catheter 302 into the implant 100 to radially-reduce the implant 100 by placing the implant 100 in tension. The implant actuation shaft 334 may be advanced distally by axial sliding, rotational engagement with a threaded surface 336, or a combination of both. In one embodiment, the implant actuation shaft 334 has a threaded portion 336 that threadably engages with a hub 236 to lock the implant 100 in a radially reduced configuration, as described above. In this embodiment, the implant 100 may be loaded by sliding the implant actuation shaft 334 distally until its threaded portion 336 comes into contact the hub 236, and then rotating the control knob 408 counterclockwise to threadably engage the threaded portion 336 and the hub 236 until the implant 100 is fully collapsed.

The diameter of the implant 100 preferably is reduced to approximately 1/3.sup.rd or less of its original diameter when collapsed. The loading collar 323 and peel-away sheath 314 are then advanced distally over the flares 510 and implant 100 until the distal tip of the implant 100 is aligned with the distal end of the peel-away sheath 314 and the distal end of the loading collar is about 1.5 cm from the distal tip of the implant 100. At this point, the flares 510 partially cover the implant. The loading collar 323 preferably is removed and discarded.

With the implant 100 partially within the recapture sheath 522 and retracted within the peel-away sheath 314, the entire system preferably is flushed with sterile heparinized saline after attaching stopcocks to the recapture sheath injection port 529, the proximal injection port 412 and distal injection port 414 of the delivery system 50. The recapture sheath 522 and the Touhy-Borst valve 530 are first thoroughly flushed through port 529. Then the distal injection port 414 and the proximal injection port 412 of the deployment handle 400 are preferably flushed through. The distal injection port 414 is in fluid communication with lumen 388 of axially moveable core 304 (as illustrated in FIG. 24A), and proximal injection port 412 is in fluid communication with injection lumens 332 of multilumen shaft 326. The transseptal sheath 520 placement preferably is reconfirmed using fluoroscopy and contrast media injection.

The delivery system 50, as described above, with implant 100 inserted therein, preferably is then inserted into the proximal end of a transseptal sheath 520 (as shown in FIG. 6). To avoid introducing air into the transseptal sheath 520 during insertion of the delivery system 50, a continual, slow flush of sterile heparinized saline preferably is applied through the proximal injection port 412 of the deployment handle 400 to the distal end of the deployment catheter 302 until the tip of the peel-away sheath 314 has been inserted into, and stops in, the hemostatic valve of the transseptal sheath 520. Preferably, the distal tip of the peel-away sheath 314 is inserted approximately 5 mm relative to the proximal end of the transseptal sheath 520.

Under fluoroscopy, the recapture sheath 522 and deployment catheter 302 preferably are advanced, relative to the peel-away sheath 314, approximately 20-30 cm from the proximal end of the transseptal sheath 520, and the system 50 preferably is evaluated for trapped air. The peel-away sheath 314 is preferably not advanced into the transseptal sheath 520 due to a hemostasis valve (not illustrated) on the transseptal sheath 520 blocking its passage. If air is present in the system 50, it may be removed by aspirating through the distal injection port 414, recapture sheath injection port 529, or proximal injection port 412. If air cannot be aspirated, the deployment catheter 302 and recapture sheath 522 preferably are moved proximally and the delivery system 50 preferably is removed from the transseptal sheath 520. All air preferably is aspirated and the flushing/introduction procedure preferably is repeated.

The peel-away sheath 314 preferably is manually slid proximally to the proximal end 524 of the recapture sheath 522. The Touhy-Borst valve 530 preferably is loosened and the deployment catheter 302 preferably is advanced distally relative to the recapture sheath 522 until the deployment handle 400 is within about 2 cm of the Touhy-Borst valve 530 of the recapture sheath 522. This causes the implant 100 to be advanced distally within the transseptal sheath 520 such that the recapture sheath 522 no longer covers the implant 100 or the flexible section 558. The Touhy-Borst valve 530 preferably is tightened to secure the deployment catheter 302 to fix relative movement between the deployment catheter 302 and recapture sheath 522.

Under fluoroscopy, the implant 100 preferably is advanced to the tip of the transseptal sheath 520 by distal movement of the delivery catheter 302. The distal hub 108 of implant 100 preferably is aligned with a transseptal sheath tip radiopaque marker 521 (see FIG. 6). Under fluoroscopy, the sheath 520 positioning within the LAA 10 preferably is confirmed with a distal contrast media injection.

The position of the implant 100 preferably is maintained by holding the deployment handle 400 stable. The transseptal sheath 520 preferably is withdrawn proximally until its tip radiopaque marker 521 is aligned with the distal end of the deployment catheter flexible segment 384. In some embodiments, the transseptal sheath 520 is withdrawn proximally until its tip radiopaque marker 521 is aligned with the distal end of the mesh sock 392. In other embodiments, the transseptal sheath 520 is withdrawn proximally until its tip radiopaque marker 521 is aligned with the proximal end of the mesh sock 392, or at a location between the proximal and distal ends of the mesh sock 392. This preferably exposes the implant 100.

In one embodiment, under fluoroscopy, the implant 100 preferably is expanded by rotating the control knob 408 clockwise until it stops. Rotating the control knob 408 preferably releases tension on the control line 312, preferably allowing the implant 100 to expand. The implant 100 preferably is self-expanding. After expansion, any tension on the LAA 10 preferably is removed by carefully retracting the deployment handle 400 under fluoroscopy until the radiopaque marker 360 (see FIG. 24) on the axially movable core 304 moves proximally approximately 1-2 mm in the guide tube 130 (see FIG. 11). In an embodiment, the position of the implant 100 relative the LAA 10 preferably is not altered because the axially movable core 304 preferably is coupled with an axially decoupled implant release and recapture mechanism 200, as is shown in an embodiment illustrated in FIGS. 16A and 16B, which allows for relative movement between the implant 100 and the axially movable core 304. The implant release and recapture mechanism 200 preferably allows for the distal portion of the axially movable core 304 to be slightly retracted proximally from the distal end 102 of the implant 100, thereby removing any axial tension that may be acting on the implant 100 through the axially movable core 304. The axial moveable core 304 radiopaque marker 360 preferably is about 1-2 mm proximal from the implant 100 distal end 102, and the transseptal sheath 520 tip preferably is about 2-3 mm proximal from the implant proximal end 104, thereby indicating a neutral position.

In another embodiment, the delivery system 50 comprises an implant 100 connected to an implant release and recapture mechanism 200, which is connected to a catheter system 300, which is connected to a deployment handle 400. A disconnect mount interface 180 on the proximal end 104 of the implant 100 is connected to a disconnect mount 236 on a catheter system 300 which provides releasable concentric loading to the implant 100 as described above. In one embodiment, the concentric loading is concentric tension. In one embodiment the concentric loading is provided by a disconnect mount interface 180 with a finger interface 182 which interacts with a flexible finger 238 on the disconnect mount 236.

As discussed above, in some embodiments the order of the following steps may be accomplished in the following sequence, or in reverse sequence, or in a combination of repeated steps in order to have the implant 100 expand and release an implant 100 in a distal, proximal, or relatively axially-stationary direction.

In one embodiment, the implant actuation shaft 334 may be retracted proximally through the catheter 302 through the implant 100 to radially-expand the implant 100 by removing the tensile load from distal end 102 of the implant 100. The implant actuation shaft 334 may be retracted proximally by axial sliding, rotational engagement with a threaded surface 336, or a combination of both. In one embodiment, the implant actuation shaft 334 has a threaded portion 336 that threadably engages with a hub 236 to lock the implant 100 in a radially reduced configuration, as described above. In this embodiment, the implant 100 may be unloaded rotating the control knob 408 until the hub 236 and implant actuation shaft 334 threaded portion 336 detach, and by sliding the implant actuation shaft 334 proximally. If the implant actuation shaft 334 is moved proximally and the proximal end 104 of the implant 100 remains relatively stationary with respect to the catheter body 302, the implant 100 will expand within the LAA 10 in a generally proximal direction, as described above.

In one embodiment a disconnect mount interface 180 on the proximal end 104 of the implant 100 is connected to a disconnect mount 236 on a catheter system 300 which can provide releasable concentric loading to the implant 100 as described above. In one embodiment, the concentric loading is concentric tension. In one embodiment the concentric loading is provided by a disconnect mount interface 180 with a finger interface 182 which interacts with a flexible finger 238 on the disconnect mount 236. The flexible finger 238 is engaged with the finger interface 182 and a lock tube 234 secures the engagement between the flexible finger 238 and the finger interface 182. In one embodiment, the implant 100 may be expanded by allowing the catheter 302 to advance distally while the implant actuation shaft 334 remains stationary at the distal end 102 of the implant 100 as is illustrated in FIGS. 18A and 18B. In another embodiment, a mesh sock 392 in a compressed state may be released to allow the proximal end 104 of the implant 100 to move distally while the implant actuation shaft 334 remains stationary at the distal end 102 of the implant 100. In another embodiment, the implant 100 may be expanded by removing the lock tube 234 from the flexible finger 238 and finger interface 182. In some embodiments, the lock tube 234 may be rotated to threadably disengage from a catheter 302 to unlock the lock tube 234. In other embodiments no lock tube 234 is necessary. When the implant actuation shaft 334 remains extended and attached to the proximal end 104 of the implant 100 and the fingers 238 are released from the finger interfaces 182, the implant 100 will expand within the LAA 10 in a generally distal direction, as described above.

The implant 100 preferably is self-expanding. After expansion, any tension on the LAA 10 preferably is removed by carefully retracting the deployment handle 400 under fluoroscopy until the radiopaque marker 360 (see FIG. 24) on the axially movable core 304 moves proximally approximately 1-2 mm in the guide tube 130 (see FIG. 11). In an embodiment, the position of the implant 100 relative the LAA 10 preferably is not altered because the implant actuation shaft 334 preferably is coupled with an axially decoupled implant release and recapture mechanism 200, as is shown in an embodiment illustrated in FIGS. 16A and 16B, which allows for relative movement between the implant 100 and the implant actuation shaft 334. The implant release and recapture mechanism 200 preferably allows for the distal portion of the axially movable core 304 to be slightly retracted proximally from the distal end 102 of the implant 100, thereby removing any axial tension that may be acting on the implant 100 through the axially movable core 304. The axial moveable core 304 radiopaque marker 360 preferably is about 1-2 mm proximal from the implant 100 distal end 102, and the transseptal sheath 520 tip preferably is about 2-3 mm proximal from the implant proximal end 104, thereby indicating a neutral position.

Under fluoroscopy, the expanded diameter (O in FIG. 6) of the implant 100 preferably is measured in at least two views to assess the position of the implant within the LAA 10. The measured implant diameter O preferably is compared to the maximum expanded diameter.

Preferably, the labeled proximal 412 and distal injection ports 414, of the deployment handle 400 shown in FIG. 22, correlate with the proximal and distal contrast media injections. The proximal contrast media injections are delivered through the delivery catheter lumen 332 to a location proximal to the implant 100. The distal contrast media injections are delivered through the axially movable core 304 to a location distal to the implant 100. Proximal contrast media injections preferably are completed in two views. If the injection rate is insufficient, the recapture sheath injection port 529 may be used independently or in conjunction with the proximal injection port 412 to deliver fluid to a location proximal to the implant 100.

If satisfactory results are seen, any transverse tension on the LAA 10 preferably is released by exposing the flexible segment 384 of the delivery system 50. The flexible catheter section 362 and the flexible core section 372 preferably are linearly co-located to cooperate as the flexible segment 384 of the delivery system 50. This preferably is accomplished by retracting the transseptal sheath 520 proximally approximately 2 cm to expose the flexible segment. By exposing the flexible segment 384, the flexible segment 384 preferably will flex to allow the implant 100 to sit within the LAA 10 free from transverse forces that may be created, for example, by contractions of the heart acting against the transseptal sheath 520 or deployment catheter 302. Once the flexible segment 384 is exposed, distal contrast media injections preferably are completed in at least two views to verify proper positioning of the implant 100. A flush of saline preferably is used as needed between injections to clear the contrast media from the LAA 10. Following the contrast media injections, the transseptal sheath 520 preferably is advanced distally to cover the flexible segment 384.

In another embodiment, any transverse tension on the LAA 10 preferably is released by a mesh sock 392 and a proximal retraction of an implant actuation shaft 334.

If implant 100 position or results are sub-optimal, the implant 100 preferably may be collapsed and repositioned in the LAA 10. In some embodiments, the implant 100 is still attached to an implant release and recapture mechanism 200 and the radial-reduction of the implant 100 is accomplished by the actuation of the implant actuation shaft 334. In other embodiments, the implant 100 must be reattached to the implant release and recapture mechanism 200 before the radial-reduction of the implant 100 can be accomplished by the actuation of the implant actuation shaft 334. To collapse and reposition an implant 100 in one embodiment under fluoroscopy, the deployment handle 400 preferably is advanced distally to place the radiopaque marker 360 of the axially moveable core 304 at the distal hub 108 of the implant 100. The distal end of the transseptal sheath 520 preferably is aligned with the distal end of the flexible segment 384. The control knob 408 preferably is rotated until the implant 100 has been collapsed to approximately 1/3.sup.rd or less of its expanded diameter. The control knob 408 preferably acts on the control line 312 to place tension on the proximal hub 104 of the implant 100, pulling the proximal hub 104 of the implant 100 proximally relative the distal hub 108 of the implant 100 to collapse the implant 100. The implant 100 preferably can be repositioned and re-expanded. In another embodiment, an implant actuation shaft 334 is reintroduced or advanced distally within a radially-enlarged implant 100 and advanced to the distal end 102 of the implant 100.

The stability of the implant 100 preferably is verified in several views. Stability tests preferably are preformed in the following manner. A contrast media filled syringe preferably is connected to the distal injection port 414 of the deployment handle 400. Under fluoroscopy, at least about a 10 mm gap between the tip of the transseptal sheath 520 and the proximal hub 110 of the implant 100 is preferably confirmed. The stability of the implant 100 in the LAA 10 preferably is evaluated using fluoroscopy and echocardiography. The recapture sheath Touhy-Borst valve 530 preferably is loosened. Then the deployment handle 400 preferably is alternately retracted and advanced about 5-10 mm while maintaining the position of the transseptal sheath 520 and simultaneously injecting contrast media through the distal injection port 414. This tests how well the implant is held within the LAA 10. If the implant stability tests are unacceptable, the implant 100 preferably may be collapsed and repositioned as described above. If repositioning the implant 100 does not achieve an acceptable result, the implant 100 preferably may be collapsed and recaptured as described further below.

The implant 100 preferably meets the following acceptance criteria, associated with the assessment techniques listed below, prior to being released. The assessment techniques to be evaluated preferably include 1) residual compression; 2) implant location; 3) anchor engagement; 4) seal quality; and 5) stability. For residual compression, the implant diameter O, as measured by fluoroscopic imaging, preferably is less than the maximum expanded diameter of the implant 100. For implant location, the proximal sealing surface of the implant 100 preferably is positioned between the LAA 10 ostium and sources of thrombus formation (pectinates, secondary lobes, etc.) (preferably imaged in at least two views). For anchor engagement, the implant frame 101 preferably is positioned within the LAA 10 so as to completely engage a middle row of anchors 118 in an LAA 10 wall (preferably imaged in at least two views). For seal quality, the contrast injections preferably show leakage rated no worse than mild (preferably defined as a flow of contrast media, well defined, and filling one-third of the LAA 10 during a proximal injection over a period of up to about five ventricular beats, preferably imaged in at least two views). For stability, there preferably is no migration or movement of the implant 100 relative to the LAA 10 wall as a result of the Stability Test.

If implant 100 recapture is necessary, because a different size implant 100 is necessary or desired, or if acceptable positioning or sealing cannot be achieved, the implant 100 preferably is fully collapsed as described above. In one embodiment, once the implant 100 is collapsed, the locking collar 315 of the peel away sheath 314 preferably is unlocked. The peel-away portion 524 of the peel-away sheath 314 preferably is split up to the reinforced section 317 and removed. The reinforced section 317 of the peel-away sheath 314 preferably is slid proximally to the hub of the recapture sheath 522. The Touhy-Borst valve 530 on the proximal end of the recapture sheath 522 preferably is slightly loosened to allow smooth movement of the sheath 522 over deployment catheter 302 without allowing air to enter past the Touhy-Borst valve 530 seal. By removing the peel-away portion 524 of peel-away sheath 314, the recapture sheath 522 can now be advanced further distally relative to the transseptal sheath 520.

While holding the deployment catheter 302 and transseptal sheath 520 in place, the recapture sheath 522 preferably is advanced distally into the transseptal sheath 520 until a half marker band 536 on the recapture sheath 522 is aligned with a full marker band 521 on the transseptal sheath 520. This preferably exposes the recapture flares 510 outside the transseptal sheath.

The collapsed implant 100 preferably is retracted into the recapture sheath 522 by simultaneously pulling the deployment handle 400 and maintaining the position of the recapture sheath 522 until approximately half the implant 100 is seated in the recapture sheath 522. The Touhy-Borst valve 530 on the recapture sheath 522 preferably is tightened over the deployment catheter 302. The recapture sheath 522 and implant 100 preferably are retracted into the transseptal sheath 520 by pulling on the recapture sheath 522 while maintaining the position of the transseptal sheath 520, preferably maintaining left atrial access. The recapture flares 510 of the recapture sheath 522 preferably cover at least some of the anchor elements 195 on the implant 100 as the implant is retracted proximally into the transseptal sheath 520. Further details are described above with respect to FIGS. 15C-15E.

If the implant's position and function are acceptable, and implant recapture is not necessary, the implant 100 preferably is released from the delivery system 50. In one embodiment, under fluoroscopy, the transseptal sheath 520 is advanced to the proximal hub 104 of the implant 100 for support. The release knob 410 on the proximal end of the deployment handle 400 preferably is rotated to release the implant 100. Rotating the release knob 410 preferably causes a threaded portion of the distal shaft 344 of the axially movable core 304 to rotate with respect to the threaded aperture 346 such that the threaded portion of the distal shaft 344 preferably is decoupled from the implant 100. Under fluoroscopy, after the axially movable core 304 is decoupled from the implant 100, the release knob 410 preferably is retracted until the distal end 310 of the axially movable core 304 is at least about 2 cm within the transseptal sheath 520.

In one embodiment a disconnect mount interface 180 on the proximal end 104 of the implant 100 is connected to a disconnect mount 236 on a catheter system 300 which can provide releasable concentric loading to the implant 100 as described above. In one embodiment, the concentric loading is concentric tension. In one embodiment the concentric loading is provided by a disconnect mount interface 180 with a finger interface 182 which interacts with a flexible finger 238 on the disconnect mount 236. The flexible finger 238 is engaged with a finger interface 182 and a lock tube 234 secures the engagement between the flexible finger 238 and the finger interface 182. Under fluoroscopy, the implant 100 may be detached by removing the lock tube 234 from the flexible finger 238 and finger interface 182. In some embodiments, the lock tube 234 may be rotated to threadably disengage from a catheter 302 to unlock the lock tube 234. In other embodiments no lock tube 234 is necessary. In other embodiments sufficient proximal retraction of the implant actuation shaft 334 is required in order to release the disconnect mount interface 180 from the disconnect mount 236, as described above.

Under fluoroscopy, while assuring that transseptal access is maintained, the delivery system 50 preferably is retracted and removed through the transseptal sheath 520. Under fluoroscopy, the transseptal sheath 520 position preferably is verified to be approximately 1 cm away from the face of the implant 100. Contrast injections, fluoroscopy and/or echocardiography preferably may be used to confirm proper positioning and delivery of the implant 100 and containment of the LAA 10. The transseptal sheath 520 preferably is withdrawn.

Throughout this application the terms implant and occlusion device have been used. One of ordinary skill in the art will appreciate that all of the disclosures herein are applicable to a wide variety of structures that include both implants that may or may not also be occlusion devices. Routine experimentation will demonstrate those limited circumstances under which certain disclosures and combinations thereof are not beneficial.

Further details regarding left atrial appendages devices and related methods are disclosed in U.S. Pat. No. 6,152,144, titled "Method and Device for Left Atrial Appendage Occlusion," filed Nov. 6, 1998, U.S. patent application Ser. No. 09/435,562, filed Nov. 8, 1999, U.S. patent application Ser. No. 10/033,371, titled "Method and Device for Left Atrial Appendage Occlusion," filed Oct. 19, 2001, and U.S. application Ser. No. 10/642,384, filed Aug. 15, 2003, titled "System and Method for Delivering a Left Atrial Appendage Containment Device," published as U.S. Publication No. 2005/0038470. The entirety of each of these is hereby incorporated by reference.

While particular forms of the invention have been described, it will be apparent that various modifications can be made without departing from the spirit and scope of the invention. Accordingly, it is not intended that the invention be limited, except as by the appended claims.

What is claimed is:

1. An implant delivery system comprising:
a catheter system including a catheter having a lumen within a distal end thereof sized and adapted to receive at least a portion of an implantable device;
an activation element slideable within the lumen of the catheter; and
an implantable device having a collapsed delivery configuration and an expanded deployed configuration, the implantable device comprising a plurality of supports initially extending distally and radially outward from a proximal hub, the implantable device comprising an occlusive portion and an anchoring portion,
wherein the occlusive portion of the implantable device comprises an occlusive material deployed over the proximal hub and at least a portion of a longitudinal extent of the plurality of supports,
wherein the anchoring portion comprises a distal hub connected to distal ends of at least some supports of the plurality of supports and the anchoring portion comprises anchoring hooks adapted to engage tissue, the anchoring hooks extending radially outward by a predetermined distance from at least some supports of the plurality of supports when the implantable device is in the expanded deployed configuration,
wherein the activation element includes a distal mating surface adapted to engage a corresponding feature of the catheter proximate the distal end of the catheter to secure the implantable device to the catheter in the collapsed delivery configuration and adapted to disengage from the corresponding feature of the catheter to allow the implantable device to transition to the expanded deployed configuration,
wherein the catheter further comprises a plurality of flexible protruding fingers configured and adapted to engage corresponding interlocking features of the implantable device in the collapsed delivery configuration and to be released therefrom upon removal of the activation element from between plurality of flexible protruding fingers.

2. The implant delivery system of claim 1, wherein the lumen of the catheter extends from the distal end of the catheter to a proximal end of the catheter.

3. The implant delivery system of claim 1, wherein the distal mating surface of the activation element and the corresponding feature of the catheter are threaded regions.

4. The implant delivery system of claim 1, wherein the occlusive material is a membrane, mesh, or fabric which facilitates cellular in-growth.

5. The implant delivery system of claim 1, wherein the corresponding interlocking features of the implantable device are features of the proximal hub.

6. The implant delivery system of claim 1, wherein the activation element, when activated, allows the plurality of flexible protruding fingers to return to a biased position.

7. The implant delivery system of claim 1, wherein the proximal hub includes an axial through bore.

8. The implant delivery system of claim 7, wherein the catheter includes a proximal injection port and a distal injection port in fluid communication, the distal injection port being located and adapted to deliver contrast media to an interior of the implantable device.

9. The implant delivery system of claim 1, wherein the activation element is slideable between a first state in which it is extended distally beyond the catheter and a second state in which it is retracted within the catheter.

10. The implant delivery system of claim 1, wherein the distal hub further comprises a distal tube having a lumen therein and extending in a proximal direction from the distal hub.

11. The implant delivery system of claim 10, wherein the distal tube receives at least a portion of the activation element when the implantable device is in the collapsed delivery configuration.

12. An implant delivery system, comprising:
an implantable device having a collapsed delivery configuration and an expanded deployed configuration, the implantable device comprising a plurality of supports initially extending distally and radially outward from a proximal hub, the implantable device comprising an occlusive portion and an anchoring portion;
a catheter including a lumen extending therethrough, the catheter being releasably attached to the proximal hub of the implantable device; and
an activation shaft movable within the lumen of the catheter to shift the implantable device between the collapsed delivery configuration and the expanded deployed configuration;
wherein the occlusive portion of the implantable device comprises an occlusive material deployed over at least a portion of a longitudinal extent of the plurality of supports;
wherein the anchoring portion comprises anchoring hooks adapted to engage tissue, the anchoring hooks extending radially outward from at least some supports of the plurality of supports when the implantable device is in the expanded deployed configuration;
wherein the implantable device includes an inner tubular member and an outer tubular member disposed within an interior of the implantable device, the inner tubular member being axially movable within and relative to the outer tubular member as the implantable device shifts from the collapsed delivery configuration to the expanded deployed configuration;

wherein the catheter further comprises a plurality of flexible protruding fingers configured and adapted to engage corresponding interlocking features of the proximal hub when a distal end of the activation shaft extends distally of distal ends of the plurality of flexible protruding fingers.

13. The implant delivery system of claim 12, wherein the plurality of flexible protruding fingers is configured to be released from the proximal hub when the distal end of the activation shaft is disposed proximal of the distal ends of the plurality of flexible protruding fingers.

14. The implant delivery system of claim 12, wherein the occlusive material is deployed over the proximal hub.

15. The implant delivery system of claim 12, wherein the inner tubular member moves distally within the outer tubular member as the implantable device shifts from the collapsed delivery configuration to the expanded deployed configuration.

16. The implant delivery system of claim 12, wherein in the collapsed delivery configuration, the inner tubular member is a proximal tubular member attached to the plurality of supports and the outer tubular member is a distal tubular member attached to the plurality of supports.

17. An implant delivery system, comprising:
an implantable device having a collapsed delivery configuration and an expanded deployed configuration, the implantable device comprising a plurality of supports initially extending distally and radially outward from a proximal hub, the implantable device comprising an anchoring portion and an occlusive portion, the occlusive portion comprising an occlusive material deployed over at least a portion of a longitudinal extent of the plurality of supports;
a catheter including a lumen extending therethrough, the catheter being releasably attached to the proximal hub of the implantable device; and
an activation shaft movable within the lumen of the catheter to shift the implantable device between the collapsed delivery configuration and the expanded deployed configuration;
wherein the implantable device includes an inner tubular member and an outer tubular member disposed within an interior of the implantable device, the inner tubular member being axially movable within and relative to the outer tubular member as the implantable device shifts from the collapsed delivery configuration to the expanded deployed configuration;
wherein the catheter further comprises a plurality of flexible protruding fingers configured and adapted to engage corresponding interlocking features of the proximal hub when a distal end of the activation shaft extends distally of distal ends of the plurality of flexible protruding fingers.

18. The implant delivery system of claim 17, wherein the plurality of flexible protruding fingers is configured to be released from the proximal hub when the distal end of the activation shaft is disposed proximal of the distal ends of the plurality of flexible protruding fingers.

19. The implant delivery system of claim 17, wherein the activation shaft extends into the inner tubular member in the collapsed delivery configuration.

20. The implant delivery system of claim 17, wherein the inner tubular member moves distally relative to the outer tubular member as the implantable device shifts from the collapsed delivery configuration to the expanded deployed configuration.

* * * * *